US011168307B2

(12) United States Patent
Paoletti et al.

(10) Patent No.: US 11,168,307 B2
(45) Date of Patent: Nov. 9, 2021

(54) **POXVIRUS-*PLASMODIUM* RECOMBINANTS, COMPOSITIONS CONTAINING SUCH RECOMBINANTS, USES THEREOF, AND METHODS OF MAKING AND USING THE SAME**

(71) Applicant: V-Core Technologies, Inc., Rensselaer, NY (US)

(72) Inventors: Enzo Paoletti, Tupper Lake, NY (US); Randall L. Weinberg, Castleton, NY (US); Scott J. Goebel, Ballston Spa, NY (US)

(73) Assignee: V-CORE TECHNOLOGIES, INC., Rensselaer, NY (US)

( * ) Notice: Subject to any disclaimer, the term of this patent is extended or adjusted under 35 U.S.C. 154(b) by 5 days.

(21) Appl. No.: 16/567,531

(22) Filed: Sep. 11, 2019

(65) Prior Publication Data

US 2020/0102544 A1    Apr. 2, 2020

Related U.S. Application Data

(63) Continuation of application No. 14/576,578, filed on Dec. 19, 2014, now abandoned.

(60) Provisional application No. 61/921,748, filed on Dec. 30, 2013.

(51) Int. Cl.
| | |
|---|---|
| *C12N 7/00* | (2006.01) |
| *A61K 39/015* | (2006.01) |
| *C12N 15/86* | (2006.01) |
| *A61K 39/275* | (2006.01) |
| *A61K 39/00* | (2006.01) |

(52) U.S. Cl.
CPC ............. *C12N 7/00* (2013.01); *A61K 39/015* (2013.01); *A61K 39/275* (2013.01); *C12N 15/86* (2013.01); *A61K 2039/5256* (2013.01); *C12N 2710/24021* (2013.01); *C12N 2710/24034* (2013.01); *C12N 2710/24122* (2013.01); *C12N 2710/24134* (2013.01); *C12N 2710/24143* (2013.01); *Y02A 50/30* (2018.01)

(58) Field of Classification Search
None
See application file for complete search history.

(56) References Cited

U.S. PATENT DOCUMENTS 5,766,597 A * 6/1998 Paoletti ................ C07K 14/445
424/199.1
2004/0019195 A1    1/2004 Scholm et al.

FOREIGN PATENT DOCUMENTS

| | | |
|---|---|---|
| WO | 1992/16616 | 10/1992 |
| WO | 2009/079564 | 6/2009 |
| WO | 2010/050913 A1 | 5/2010 |

OTHER PUBLICATIONS

Kibler et al. Improved NYVAC-Based Vaccine Vectors. PLoS ONE, 2011, 6(11): e25674.*
Bargieri et al. Malaria Vaccine Development: Are Bacterial Flagellin Fusion Proteins the Bridge betweenMouse and Humans? Journal of Parasitology Research, vol. 2011, Article ID 965369, 10 pages. Date of publication: 2011.*
International Preliminary Report on Patentability dated Jul. 5, 2016, issued in PCT/US2014/071386.
International Search Report and Written Opinion of the ISR dated Apr. 16, 2015 issued in PCT/US14/71386.
Supplemental EP Search Report dated Jul. 18, 2017 issued in EP Application No. 14877230.
Delaney, et al., A Recombinant Flagellin-Poxvirus Fusion Protein Vaccine Elicits Complement-Dependent Protection Against Respitory Challenge with Vaccinia Virus in Mice, Viral Immunology (Apr. 2010) 23(2):201-210.
Shisler, et al., The Vaccinia Virus K1 L Gene Product Inhibits Host NF-kB Activation by Preventing IkBα Degradation, Journal of Virology (Apr. 2004) 78(7):3553-3560.

* cited by examiner

*Primary Examiner* — Nianxiang Zou
(74) *Attorney, Agent, or Firm* — Duane Morris LLP; Thomas J. Kowalski; Deborah L. Lu

(57) ABSTRACT

The invention provides a recombinant or synthetic or engineered or non-naturally occurring poxvirus that contains and expresses DNA encoding a heterologous or exogenous antigen, epitope or immunogen and Flagellin or an operable binding portion thereof. The poxvirus can contain or be engineered to contain and express vaccinia host range gene K1L. The poxvirus can be attenuated as to mammals, e.g., NYVAC, NYVAC.1, NYVAC.2, avipox, canarypox, fowlpox, ALVAC, TROVAC, MVA, or MVA-BN. The invention also provides methods for inducing an immunological response involving the poxvirus, and compositions containing the poxvirus. The antigen, epitope or immunogen that the poxvirus expresses can be at least one *Plasmodium* antigen. The *Plasmodium* antigen(s), epitope(s) or immunogen(s) can be SERA, ABRA, Pfhsp70, AMA-1, Pfs25, Pfs16, CSP, PfSSP2, LSA-1 repeatless, MSA-1, AMA-1 or combination(s) thereof. Advantageously the poxvirus contains DNA coding for and expresses *Plasmodium* antigen(s) CSP, PfSSP2, LSA-1-repeatless, MSA-1, SERA, AMA-1 and Pfs25. Also, advantageously, the poxvirus is a NYVAC poxvirus. The invention thus also provides an anti-malarial immunogenic or immunological compositions comprising the poxvirus, and methods for inducing an immunogenic or immunological response against malaria or *Plasmodium* in a mammal comprising administering to the mammal the poxvirus or an immunological or immunogenic composition containing the poxvirus. The mammal can be a human.

19 Claims, 7 Drawing Sheets
Specification includes a Sequence Listing.

SEQ ID NO: 20

FIG. 2A

SEQUENCE LISTING

```
<160> NUMBER OF SEQ ID NOS: 20

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tattcaagct tgaattcgtg tcggtgaatc aatcg                              35

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aactctagag gatccaataa catcaagttg taattg                             36

<210> SEQ ID NO 3
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
actgtaaaaa tagaaactat aatcatataa tagtgtaggt tggtagtagg gtactcgtga     60
ttaattttat tgttaaactt gtcttaactc ttaagtctta ttaatatg                108

<210> SEQ ID NO 4
<211> LENGTH: 500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
agatctactg taaaaataga aactataatc atataatagt gtaggttggt agtagggtac     60
tcgtgattaa ttttattgtt aaacttgtct taactcttaa gtcttattaa tatggcacaa    120
gtcattaata caaacagcct gtcgctgttg acccagaata acctgaacaa atcccagtcc    180
gctctgggca ccgctatcga gcgtctgtct tccggtctgg tacctccgtt ctggcgcagg    240
cgaaccaggt tccgcaaaac gtcctctctt tactgcgtta attttatct cgaggccaat    300 taggcctatt atatttttta tctaaaaaac taaaaataaa cattgattaa attttaatat    360
aatacttaaa aatggatgtt gtgtcgttag ataaaccgtt tatgtatttt gaggaaattg    420
```

```
ataatgagtt agattacgaa ccagaaagtg caaatgaggt cgcaaaaaaa ctgccgtatc    480
aaggacagtt aaaagaattc                                                500
```

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

```
Arg Arg Ile Lys Ser
1               5
```

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Ile Lys Ser Arg Arg
1               5
```

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
aatagacctg cttcgttggc ctc                                             23
```

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
agcactttttg atcatactag cgttcttatt tttg                                34
```

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
cctacaggtc gaccattaca ccaggaacat acatacc                              37
```

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
cctacaggtc gaccatatcc gttttttgcca atatcac                                37

<210> SEQ ID NO 11
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gaacgctagt atgatcaaaa gtgcttttct tcccactggt gct                          43

<210> SEQ ID NO 12
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tagtctcctc gagctgacag atctataaaa attaatagta tggttttcc atcag              55

<210> SEQ ID NO 13
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gatctgtcag ctcgaggaga ctagtcgtag ggcccggccg tggcaatatt ctgta             55

<210> SEQ ID NO 14
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gatggaaaaa ccatactatt aattttata gatctactgt aaaaatagaa actat              55

<210> SEQ ID NO 15
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atattgccac ggccgggccc tacgactagt ctcctcgaga taaaaattaa cgcag             55

<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 16
agctccaaga atattcattt cagatgataa agacagttta aaatg          45

<210> SEQ ID NO 17
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
catctgaaat gaatattctt ggagctataa ttttttttatt cccttcatca tc     52

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tgactaaata tttaacattc ccaagatgat tc                     32

<210> SEQ ID NO 19
<211> LENGTH: 4655
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
catccactat attgttttgc acatctctac cattaactag aaacaaatca agaaaatca       60 aaaacacaat gactaaatat ttaacattcc aagatgatt cattttatat tgtaattata     120
tattttcaat tttgaggatc agcttacatc atgcagtggt aaacaaaaa cattttttatt    180 ctcaaatgag ataaagtgaa aatatatatc attatattac aaagtacaat tatttaggtt    240
taatcatgag aaaattatac tgcgtattat tattgagcgc ctttgagttt acatatatga    300
taaactttgg aagaggacag aattattggg aacatcccata tcaaaatagt gatgtgtatc    360
gtccaatcaa cgaacatagg gaacatccaa aagaatacga atatccatta caccaggaac    420
atacatacca acaagaagat tcaggagaag acgaaaatac attcaacac gcatatccaa    480 tagaccacga aggtgccgaa cccgcaccac aagaacaaaa tttattttca agcattgaaa    540
tagtagaaag aagtaattat atgggtaatc catggacgga atatatgca aaatatgata    600 ttgaagaagt tcatggttca ggtataagag tagatttagg agaagatgct gaagtagctg    660
gaactcaata tagacttcca tcagggaaat gtccagtatt tggtaaaggt ataattattg    720
agaattcaaa tactactttt ttaacaccgg tagctacggg aaatcaatat ttaaaagatg    780
gaggttttgc ttttcctcca acagaacctc ttatgtcacc aatgacatta gatgaaatga    840
gacatttcta taagataat aaaatatgtaa aaaatttaga tgaattgact ttatgttcaa    900
gacatgcagg aaaatatgatt ccagataatg ataaaaattc aaattataaa tatccagctg    960
tttatgatga caaagataaa aagtgtcata tattatatat tgcagctcaa gaaaataatg   1020
gtcctagata ttgtaataaa gacgaaagta aaagaaacag catgttttgt tttagaccag   1080
caaaagatat atcatttcaa aactatacat atttaagtaa gaatgtagtt gataactggg   1140
```

```
aaaaagtttg ccctagaaag aatttacaga atgcaaaatt cggattatgg gtcgatggaa    1200
attgtgaaga tataccacat gtaaatgaat ttccagcaat tgatctttt gaatgtaata     1260 aattagtttt tgaattgagt gcttcggatc aacctaaaca atatgaacaa catttaacag    1320
attatgaaaa aattaaagaa ggtttcaaaa ataagaacgc tagtatgatc aaaagtgctt    1380
ttcttcccac tggtgctttt aaagcagata gatataaaag tcatggtaag ggttataatt    1440
ggggaaatta taacacagaa acacaaaaat gtgaattttt taatgtcaaa ccaacatgtt    1500
taattaacaa ttcatcatac attgctacta ctgctttgtc ccatcccatc gaagttgaaa    1560
acaattttcc atgttcatta tataaagatg aaataatgaa agaaatcgaa agagaatcaa    1620
aacgaattaa attaaatgat aatgatgatg aagggaataa aaaaattata gctccaagaa    1680
tattcatttc agatgataaa gacagtttaa aatgcccatg tgaccctgaa atggtaagta    1740
atagtacatg tcgtttcttt gtatgtaaat gtgtagaaag aagggcagaa gtaacatcaa    1800
ataatgaagt tgtagttaaa gaagaatata agatgaataa tgcagatatt cctgaacata    1860
aaccaactta tgataaaatg aaaattataa ttgcatcatc agctgctgtc gctgtattag    1920
caactatttt aatggtttat ctttataaaa gaaaaggaaa tgctgaaaaa tatgataaaa    1980
tggatgaacc acaagattat gggaaatcaa attcaagaaa tgatgaaatg ttagatcctg    2040
aggcatcttt ttgggggggaa gaaaaaagag catcacatac aacaccagtt ctgatggaaa    2100
aaccatacta ttaattttta tagatctact gtaaaaatag aaactataat catataatag    2160
tgtaggttgg tagtagggta ctcgtgatta attttattgt taaacttgtc ttaactctta    2220
agtcttatta atatggcaca agtcattaat acaaacagcc tgtcgctgtt gacccagaat    2280
aacctgaaca aatcccagtc cgctctgggc accgctatcg agcgtctgtc ttccggtctg    2340
cgtatcaaca gcgcgaaaga cgatgcggca ggtcaggcga ttgctaaccg ttttaccgcg    2400
aacatcaaag gtctgactca ggcttcccgt aacgctaacg acggtatctc cattgcgcag    2460
accactgaag gcgcgctgaa cgaaatcaac aacaacctgc agcgtgtgcg tgaactggcg    2520
gttcagtctg ctaacagcac caactcccag tctgacctcg actccatcca ggctgaaatc    2580
acccagcgcc tgaacgaaat cgaccgtgta tccggccaga ctcagttcaa cggcgtgaaa    2640
gtcctggcgc aggacaacac cctgaccatc caggttggtg ccaacgacgg tgaaactatc    2700
gatatcgatc tgaagcagat caactctcag accctgggtc tggatacgct gaatgtgcaa    2760
caaaaatata aggtcagcga tacggctgca actgttacag atatgccga tactacgatt     2820 gctttagaca ataagtacttt taaagcctcg gctactggtc ttggtggtac tgaccagaaa    2880
attgatggcg atttaaaatt tgatgatacg actggaaaat attacgccaa agttaccgtt    2940
acggggggaa ctggtaaaga tggctattat gaagtttccg ttgataagac gaacggtgag    3000
gtgactcttg ctggcggtgc gacttccccg cttacaggtg gactacctgc gacagcaact    3060
gaggatgtga aaaatgtaca agttgcaaat gctgatttga cagaggctaa gccgcattg     3120 acagcagcag gtgttaccgg cacagcatct gttgttaaga tgtcttatac tgataataac    3180
ggtaaaacta ttgatggtgg tttagcagtt aaggtaggcg atgattacta ttctgcaact    3240
caaaataaag atggttccat aagtattaat actacgaaat acactgcaga tgacggtaca    3300
tccaaaactg cactaaacaa actgggtggc gcagacggca aaaccgaagt tgtttctatt    3360
ggtggtaaaa cttacgctgc aagtaaagcc gaaggtcaca actttaaagc acagcctgat    3420
ctggcggaag cggctgctac aaccaccgaa aaccgcttgc agaaaattga tgctgctttg    3480
```

-continued

```
gcacaggttg acacgttacg ttctgacctg ggtgcggtac agaaccgttt caactccgct     3540
attaccaacc tgggcaacac cgtaaacaac ctgacttctg cccgtagccg tatcgaagat     3600
tccgactacg cgaccgaagt ttccaacatg tctcgcgcgc agattctgca gcaggccggt     3660
acctccgttc tggcgcaggc gaaccaggtt ccgcaaaacg tcctctcttt actgcgttaa     3720
tttttatctc gaggagacta gtcgtagggc ccggccgtgg caatattctg tattacgtat     3780
tatatatgta ataaacgttc acgtaaatac aaaacagaga acaaagtcta gattttgac      3840 ttacataaat gtctgggata gtaaaatcta tcatattgag cggaccatct ggttcaggaa     3900
agacagccat agccaaaaga ctatgggaat atatttggat ttgtggtgtc ccataccact     3960
agatttcctc gtcctatgga acgagaaggt gtcgattacc attacgttaa cagagaggcc     4020
atctggaagg gaatagccgc cggaaacttt ctagaacata ctgagttttt aggaaatatt     4080
tacggaactt ctaaaactgc tgtgaataca gcggctatta ataatcgtat ttgtgtgatg     4140
gatttaaaca tcgacggtgt tagaagtttt aaaaatactt acctaatgcc ttactcggtg     4200
tatataagac ctacctctct taaaatggtt gagaccaagc ttcgttgtag aaacactgaa     4260
gctaacgatg agattcatcg tcgcgtgata ttggcaaaaa cggatatgga tgaggccaac     4320
gaagcaggtc tattcgacac tattattatt gaagatgatg tgaatttagc atatagtaag     4380
ttaattcaga tactacagga ccgtattaga atgtatttta acactaatta aagacttaag     4440
acttaaaact tgataattaa taatataact cgttttata tgtggctatt tcaacgtcta      4500
atgtattagt taaatattaa aacttaccac gtaaaactta aatttaaaa tgatatttca      4560 ttgacagata gatcacacat tatgaacttt caaggacttg tgttaactga caattgcaaa     4620
aatcaatggg tcgttggacc attaatagga aaagg                                4655
```

<210> SEQ ID NO 20
<211> LENGTH: 990
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 20

```
ctcgagtaat taattagatc tattagagat attattaatt ctggtgcaat atgacaaaat      60
tataaaaaat gaaaaatat acactaatta gcgtctcgtt tcagacatgg atctgtcacg      120
aattaatact tggaagtcta agcagctgaa aagctttctc tctagtaaag atacatttaa     180
ggcggatgtc catggacata gtgccttgta ttatgcaata gctgataata acgtgcgtct     240
agtatgtacg ttgttgaacg ctggagcatt gaaaaatctt ctagagaatg aatttccatt     300
acatcaggca gccacattag aagataccaa aatagtaaag atttttgctat tcagtggaat     360 ggatgattca caatttgatg acaaaggaaa caccgcattg tattatgcgg ttgatagtgg     420
taacatgcaa acggtgaaac tgtttgttaa gaaaaattgg agactgatgt tctatgggaa     480
aactggatgg aaaacttcat tttatcatgc cgtcatgctt aatgatgtaa gtattgtatc     540
atactttctt tcagaaatac catctacttt tgatctggct attctcctta gttgtattca     600
caccactata aaaaatggac acgtggatat gatgattctc ttgctcgact atatgacgtc     660
gacaaacacc aataattccc ttctcttcat tccggacatt aaattggcta tagataataa     720
agacattgag atgttacagg ctctgttcaa atacgacatt aatatctact ctgttaatct     780
ggaaaatgta ctattggatg atgccgaaat aactaagatg attatagaaa agcatgttga     840
```

-continued

| | | | | |
|---|---|---|---|---|
| atacaagtct | gactcctata | caaaagatct | cgatatcgtc | aagaataata aattggatga | 900 |
| aataattagc | aaaaacaagg | aactcagact | catgtacgtc | aattgtgtaa agaaaaacta | 960 |
| attagattct | cccacatttt | tgttaacact | | | 990 |

POXVIRUS-*PLASMODIUM* RECOMBINANTS, COMPOSITIONS CONTAINING SUCH RECOMBINANTS, USES THEREOF, AND METHODS OF MAKING AND USING THE SAME

RELATED APPLICATIONS AND/OR INCORPORATION BY REFERENCE

This application is a continuation of U.S. application Ser. No. 14/576,578 filed Dec. 19, 2014, which claims priority from US provisional application Ser. No. 61/921,748, filed Dec. 30, 2013.

The foregoing application(s), and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Feb. 17, 2015, is named 45952.99.2001_SL.txt and is 12,815 bytes in size.

FIELD OF INVENTION

The present invention relates to modified poxvirus and to the methods of making and using the same. In certain embodiments, the invention relates to recombinant poxvirus, which virus expresses exogenous or heterologous gene product(s), e.g., from *Plasmodium*, a specific poxvirus replication regulator and an adjuvant for immune-response enhancement, and immunogenic compositions or vaccines containing such poxvirus, and methods for providing immunity, e.g., protective immunity, against *Plasmodium* infections.

BACKGROUND OF INVENTION

Information concerning poxviruses, such as Chordopoxvirinae subfamily poxviruses (poxviruses of vertebrates), for instance, orthopoxviruses and avipoxviruses, e.g., vaccinia virus (e.g., Wyeth Strain, WR Strain (e.g., ATCC® VR-1354), Copenhagen Strain, NYVAC, NYVAC.1, NYVAC.2, MVA, MVA-BN), canarypox virus (e.g., Wheatley C93 Strain, ALVAC), fowlpox virus (e.g., FP9 Strain, Webster Strain, TROVAC), dovepox, pigeonpox, quailpox, and raccoon pox, inter alia, synthetic or non-naturally occurring recombinants thereof, uses thereof, and methods for making and using such recombinants may be found in scientific and patent literature, such as:

U.S. Pat. Nos. 4,603,112, 4,769,330, 5,110,587, 5,174,993, 5,364,773, 5,762,938, 5,494,807, 5,766,597, 7,767,449, 6,780,407, 6,537,594, 6,265,189, 6,214,353, 6,130,066, 6,004,777, 5,990,091, 5,942,235, 5,833,975, 5,766,597, 5,756,101, 7,045,313, 6,780,417, 8,470,598, 8,372,622, 8,268,329, 8,268,325, 8,236,560, 8,163,293, 7,964,398, 7,964,396, 7,964,395, 7,939,086, 7,923,017, 7,897,156, 7,892,533, 7,628,980, 7,459,270, 7,445,924, 7,384,644, 7,335,364, 7,189,536, 7,097,842, 6,913,752, 6,761,893, 6,682,743, 5,770,212, 5,766,882, and 5,989,562, and Panicali, D. Proc. Natl. Acad. Sci. 1982; 79; 4927-493, Panicali D. Proc. Natl. Acad. Sci. 1983; 80(17): 5364-8, Mackett, M. Proc. Natl. Acad. Sci. 1982; 79: 7415-7419, Smith G L. Proc. Natl. Acad. Sci. 1983; 80(23): 7155-9, Smith G L. Nature 1983; 302: 490-5, Sullivan V J. Gen. Vir. 1987; 68: 2587-98, Perkus M Journal of Leukocyte Biology 1995; 58:1-13, Yilma T D. Vaccine 1989; 7: 484-485, Brochier B. Nature 1991; 354: 520-22, Wiktor, T J. Proc. Natl Acd. Sci. 1984; 81: 7194-8, Rupprecht, C E. Proc. Natl Acd. Sci. 1986; 83: 7947-50, Poulet, H Vaccine 2007; 25(July): 5606-12, Weyer J. Vaccine 2009; 27(November): 7198-201, Buller, R M Nature 1985; 317(6040): 813-5, Buller R M. J. Virol. 1988; 62(3):866-74, Flexner, C. Nature 1987; 330(6145): 259-62, Shida, H. J. Virol. 1988; 62(12): 4474-80, Kotwal, G J. J. Virol. 1989; 63(2): 600-6, Child, S J. Virology 1990; 174(2): 625-9, Mayr A. Zentralbl Bakteriol 1978; 167(5,6): 375-9, Antoine G. Virology. 1998; 244(2): 365-96, Wyatt, L S. Virology 1998; 251(2): 334-42, Sancho, M C. J. Virol. 2002; 76(16); 8313-34, Gallego-Gomez, J C. J. Virol. 2003; 77(19); 10606-22), Goebel S J. Virology 1990; (a,b) 179: 247-66, Tartaglia, J. Virol. 1992; 188(1): 217-32, Najera J L. J. Virol. 2006; 80(12): 6033-47, Najera, J L. J. Virol. 2006; 80: 6033-6047, Gomez, C E. J. Gen. Virol. 2007; 88: 2473-78, Mooij, P. Jour. Of Virol. 2008; 82: 2975-2988, Gomez, C E. Curr. Gene Ther. 2011; 11: 189-217, Cox, W. Virology 1993; 195: 845-50, Perkus, M. Jour. Of Leukocyte Biology 1995; 58: 1-13, Blanchard T J. J Gen Virology 1998; 79(5): 1159-67, Amara R. Science 2001; 292: 69-74, Hel, Z., J. Immunol. 2001; 167: 7180-9, Gherardi M M. J. Virol. 2003; 77: 7048-57, Didierlaurent, A. Vaccine 2004; 22: 3395-3403, Bissht H. Proc. Nat. Aca. Sci. 2004; 101: 6641-46, McCurdy L H. Clin. Inf. Dis 2004; 38: 1749-53, Earl P L. Nature 2004; 428: 182-85, Chen Z. J. Virol. 2005; 79: 2678-2688, Najera J L. J. Virol. 2006; 80(12): 6033-47, Nam J H. Acta. Virol. 2007; 51: 125-30, Antonis A F. Vaccine 2007; 25: 4818-4827, B Weyer J. Vaccine 2007; 25: 4213-22, Ferrier-Rembert A. Vaccine 2008; 26(14): 1794-804, Corbett M. Proc. Natl. Acad. Sci. 2008; 105(6): 2046-51, Kaufman H L., J. Clin. Oncol. 2004; 22: 2122-32, Amato, R J. Clin. Cancer Res. 2008; 14(22): 7504-10, Dreicer R. Invest New Drugs 2009; 27(4): 379-86, Kantoff P W. J. Clin. Oncol. 2010, 28, 1099-1105, Amato R J. J. Clin. Can. Res. 2010; 16(22): 5539-47, Kim, D W. Hum. Vaccine. 2010; 6: 784-791, Oudard, S. Cancer Immunol. Immunother. 2011; 60: 261-71, Wyatt, L S. Aids Res. Hum. Retroviruses. 2004; 20: 645-53, Gomez, C E. Virus Research 2004; 105: 11-22, Webster, D P. Proc. Natl. Acad. Sci. 2005; 102: 4836-4, Huang, X. Vaccine 2007; 25: 8874-84, Gomez, C E. Vaccine 2007a; 25: 2863-85, Esteban M. Hum. Vaccine 2009; 5: 867-871, Gomez, C E. Curr. Gene therapy 2008; 8(2): 97-120, Whelan, K T. Plos one 2009; 4(6): 5934, Scriba, T J. Eur. Jour. Immuno. 2010; 40(1): 279-90, Corbett, M. Proc. Natl. Acad. Sci. 2008; 105: 2046-2051, Midgley, C M. J. Gen. Virol. 2008; 89: 2992-97, Von Krempelhuber, A.

Vaccine 2010; 28: 1209-16, Perreau, M. J. Of Virol. 2011; October: 9854-62, Pantaleo, G. Curr Opin HIV-AIDS. 2010; 5: 391-396,
each of which is incorporated herein by reference.

Information on a particular NYVAC-*Plasmodium* recombinant known as VP 1209 or NYVAC-Pf7 is discussed in Tine et al, "NYVAC-Pf7: a poxvirus-vectored, multiantigen, falciparum malaria multistage vaccine candidate for Plasmodium," Infect. Immun. 1996, 64(9):3833, and Ockenhouse et al, "Phase I/IIa Safety, Immunogenicity, and Efficacy Trial of NYVAC-Pf7, a Pox-Vectored, Multiantigen, Multistage Vaccine Candidate for *Plasmodium falciparum* Malaria," 1998; 177:1664-73, each of which is incorporated herein by reference.

Despite such information, to date, there are no licensed recombinant poxvirus vaccines for use in humans; see Rollier C S. Curr. Opin. Immun. 2011; 23(June): 377-82.

In addition, malaria is considered the most important parasitic disease in the world. It is estimated that malaria caused over 200 million clinical episodes worldwide resulting in 655,000 deaths, mostly African children; see WHO Global Malaria Program 2011. Furthermore the economic losses are magnified as most of the endemic countries are impoverished, costing some 3 billion dollars in Africa alone; see Teklehaimanot A. J. Trop. Med. Hyg. 2007; 77(6): 138-44. There have been substantial efforts and resources directed to methods and approaches for control-intervention such as indoor spraying, insecticidal nets, rapid diagnostics for testing, especially pregnant woman and children; see Aponte J J. Lancet 2009; 374(9700): 1533-44., Menendez C. Lancet Infect. Dis. 2007; 7(2): 126-35. However, as these control interventions programs had a measured degree of success, it is with the realization that to substantially reduce disease costs and burden to society vaccines against malaria are crucial to reduce the morbidity and mortality of this disease; see Malaria Eradication: Vaccines PloS Med. 2011; 8(1): e1000398. A focused effort and strategic goal was put forth by the international organization PATH, Malaria Vaccine Initiative (MVI), that by 2020 malaria vaccines provide 80% protective efficacy against *P. falciparum*.

Citation or identification of any document in this application is not an admission that such document is available as prior art to the present invention.

OBJECTS AND/OR SUMMARY OF THE INVENTION

The present invention recognizes and endeavors to address poxvirus (e.g., recombinant poxvirus) immunological or immunogenic composition or vaccine induction of only weak or suboptimal immune correlatives; see, e.g., Smith, J M. AIDS Res. Hum. Retroviruses 2004; 20: 1335-1347, Hanke, T. J. Gen. Virol. 2007; 88: 1-12, Sandstrom, E. J. Inf. Dis. 2008; 198: 1482-90, Walker, B D. Science 2008; 320: 760-4, Sekaly, R P. J. Exp. Med. 2008; 205: 7-12. Rerks-Ngarm S. 2009; N Engl J Med 361: 2209-2220.

The term "poxvirus" includes members of the Chordopoxvirinae subfamily, such as orthopoxviruses and avipoxviruses, e.g., vaccinia virus (e.g., Wyeth Strain, W R Strain (e.g., ATCC® VR-1354), Copenhagen Strain, NYVAC, MVA, MVA-BN), canarypox virus (e.g., Wheatley C93 Strain, ALVAC), fowlpox virus (e.g., FP9 Strain, Webster Strain, TROVAC), dovepox, pigeonpox, quailpox, and raccoon pox, inter alia; and it especially includes poxviruses of documents cited herein, including poxviruses that also express transcription and/or translation factor(s) of U.S. Pat. Nos. 5,990,091, 6,130,066 and 6,004,777.

In this regard, in one aspect the invention provides a poxvirus that is a synthetic or non-naturally occurring, i.e., an engineered, synthetic or a non-naturally-occurring poxvirus, e.g., through recombination, advantageously an attenuated poxvirus as to a mammal, such as NYVAC, NYVAC.1, NYVAC.2, avipox, canarypox, fowlpox, ALVAC, TROVAC, MVA, MVA-BN, that through such engineering contains DNA encoding Flagellin (or an operable binding portion thereof) and/or vaccinia host range gene K1L, and expresses such DNA. Advantageously, the poxvirus contains and expresses DNA encoding Flagellin (or an operable binding portion thereof) and vaccinia host range gene K1L.

Thus, as to attenuated poxviruses as to a mammals, such as NYVAC, NYVAC.1, NYVAC.2, avipox, canarypox, fowlpox, ALVAC, TROVAC, MVA, MVA-BN, the invention comprehends such a poxvirus that is synthetic or non-naturally occurring, i.e., that has been engineered or manipulated, e.g., through recombination, to contain, advantageously in a non-essential region, DNA encoding Flagellin (or an operable binding portion thereof) and/or vaccinia host range gene K1L, and express such DNA. The synthetic or non-naturally occurring or engineered or recombinant poxvirus that contains and expresses DNA encoding Flagellin (or an operable binding portion thereof) and/or vaccinia host range gene K1L can also be manipulated, engineered to contain and express DNA coding for one or more antigen(s), immunogen(s) or protein(s) that is/are foreign or exogenous or heterologous to the poxvirus.

The invention also comprehends compositions containing such an engineered or synthetic or non-naturally-occurring or recombinant poxvirus, e.g., immunogenic or immunological or vaccine compositions, uses of such a poxvirus or composition, e.g., to stimulate an immune response, such as a protective immune response, for example for generation of antibodies for use either in vivo, in vitro or ex vivo, and methods of making such poxviruses and compositions, and methods of using such poxviruses and compositions. Such compositions can contain an amount of poxvirus akin to the amount of recombinant poxvirus found in prior art recombinant poxvirus immunogenic or immunological or vaccine compositions. Similarly, in methods for inducing an immune or protective immune response, the amount of composition and/or poxvirus to be administered can be akin to the amount administered in prior art methods for inducing an immune or protective immune response by recombinant poxvirus compositions or recombinant poxviruses. NYVAC expressing Flagellin (FliC) can be a novel vaccine directed to poxvirus infections, including smallpox.

In another aspect the invention provides a poxvirus that is a synthetic or non-naturally occurring, i.e., an engineered, synthetic or a non-naturally-occurring poxvirus, e.g., through recombination, advantageously an attenuated poxvirus as to a mammal, such as NYVAC, NYVAC.1, NYVAC.2, avipox, canarypox, fowlpox, ALVAC, TROVAC, MVA, MVA-BN, that through such engineering contains, advantageously in a non-essential region, DNA encoding Flagellin (or an operable binding portion thereof) and/or vaccinia host range gene K1L, and expresses such DNA, and DNA encoding gene product(s) of *Plasmodium* and expresses such DNA encoding gene product(s) of Plasmodium. Thus, as to attenuated poxviruses as to mammals, such as NYVAC, NYVAC.1, NYVAC.2, avipox, canarypox, fowlpox, ALVAC, TROVAC, MVA, MVA-BN, the invention comprehends such a poxvirus that is synthetic or non-naturally occurring, i.e., that has been engineered or manipulated, e.g., through recombination, to contain DNA encoding Flagellin (or an operable binding portion thereof) and/or vaccinia host range gene K1L and express such DNA, and DNA encoding gene product(s) of *Plasmodium* and express such DNA encoding gene product(s) of Plasmodium. The engineered, synthetic, non-naturally occurring and/or recombinant poxvirus of the invention thus co-expresses gene product(s) of Plasmodium, and Flagellin (or an operable binding portion thereof) (and optionally also K1L). The invention also comprehends compositions containing such an engineered or synthetic or non-naturally-occurring or recombinant poxvirus, e.g., immunogenic or immunological or vaccine compositions, uses of such a poxvirus or composition, e.g., to stimulate an immune response, such as a protective immune response, for example for generation of antibodies for use either in vivo, in vitro or ex vivo, and methods of making such poxviruses and compositions, and methods of using such poxviruses and compositions. Such compositions can contain an amount of poxvirus akin to the amount of recombinant poxvirus found in prior art recombinant poxvirus immunogenic or immunological or vaccine compositions. Similarly, in methods for inducing an immune or protective immune response, the amount of composition and/or poxvirus to be administered can be akin the amount administered in prior art methods for inducing an immune or protective immune response by recombinant poxvirus compositions or recombinant poxviruses.

Immunogenic or immunological compositions stimulate an immune response that may, but need not be, protective. A vaccine stimulates a protective immune response. Advantageously, a vaccine against *Plasmodium* or malaria provides at least 80% protective efficacy against *P. falciparum* (protection in at least 80% of subjects receiving the vaccine). When other than a non-essential region is used as the locus or loci for DNA encoding Flagellin and/or DNA coding for an antigen or immunogen such as *Plasmodium* antigen(s) or immunogen(s), the skilled person may employ a complementing host cell or helper virus, see, e.g., U.S. Pat. No. 5,766,882.

The DNA encoding gene product(s) of *Plasmodium* advantageously codes for *Plasmodium* antigen(s) or immunogen(s), e.g., SERA, ABRA, Pfhsp70, AMA-1, Pfs25, Pfs16, CSP, PfSSP2, LSA-1 repeatless, MSA-1, AMA-1 or combination(s) thereof. The DNA encoding gene product(s) of *Plasmodium* advantageously codes for sequences for CSP, PfSSP2, LSA-1-repeatless, MSA-1, SERA, AMA-1 and Pfs25, akin to NYVAC-Pf7. The vector is advantageously NYVAC. The vector can also express a translation and/or transcription factor, such as in U.S. Pat. Nos. 5,990,091, 6,130,066 and 6,004,777. Without wishing to be bound by any one particular theory, the Flagellin (or an operable binding portion thereof) when expressed in an attenuated vector, such as a NYVAC vector, may have an adjuvant or immunostimulatory effect. When the vector expressing Flagellin (or an operable binding portion thereof) is advantageously a NYVAC vector, this is advantageously an "enhanced" NYVAC vector (i.e., it also contains and expresses vaccinia K1L). Advantageously, an "enhanced" replication competent NYVAC vector that contains and expresses Flagellin (or an operable binding portion thereof) also contains and expresses *Plasmodium falciparum* CSP, PfSSP2, LSA-1-repeatless, MSA-1, SERA, AMA-1 and Pfs25. Such a vector has the capacity for a level of limited replication in humans while retaining the established vector safety profile of NYVAC with open reading frames for virulence factors deleted or disrupted, and can obtain an immunological or immunogenic response that is desired for a malaria vaccine.

(Najera, J L. 2010; Plos one (5): e1406, Kibler, K V. Plos one 2011; 6: e25674)

Compositions of the invention can contain an amount of engineered, synthetic, non-naturally occurring or recombinant Flagellin-Plasmodium-poxvirus (that advantageously also contains and expresses vaccinia K1L) as in NYVAC-Pf7 compositions; and, in methods for inducing an immune or protective immune response of the invention, the amount of composition and/or poxvirus to be administered can be akin the amount administered in prior art methods involving NYVAC-Pf7.

Without wishing to be bound by any one particular theory, the invention provides self-adjuvanting immunogenic, immunological or vaccine compositions (by expression of Flagellin or an operable binding portion thereof by the poxvirus, especially with expression of vaccinia K1L). These vectors (poxviruses that express Flagellin or an operable binding portion thereof) are capable of triggering innate immunity and important pro-inflammatory cascade(s) critical for the development of robust adaptive immune responses that can provide protective immunity, e.g. against *Plasmodium* infection. The invention thus provides a replication competent, engineered, synthetic, non-naturally occurring or recombinant poxvirus useful for the production of *Plasmodium* immunogen(s) or antigen(s), in vivo or in vitro; and, the resulting immunogen(s) or antigen(s).

Accordingly, in an aspect, the invention relates to a recombinant poxvirus containing therein DNA encoding at least one *Plasmodium* antigen or immunogen and at least one DNA sequence encoding Flagellin or an operable binding portion thereof and/or the vaccinia host range gene K1L—and advantageously both the DNA sequence encoding Flagellin or an operable binding portion thereof and the vaccinia host range gene K1L—advantageously in a nonessential region of the poxvirus genome. The poxvirus is advantageously NYVAC. In an advantageous aspect, the recombinant poxvirus expresses *Plasmodium* SERA, ABRA, Pfhsp70, AMA-1, Pfs25, Pfs16, PfSSP2, LSA-1, LSA-1-repeatless, MSA-1, CSP, MSA-1 N-terminal p83 or MSA-1 C-terminal gp42 gene. Advantageously, a plurality of *Plasmodium* genes are co-expressed in the host by the recombinant inventive poxvirus, NYVAC e.g., CSP, PfSSP2, LSA-1-repeatless, MSA-1, SERA, AMA-1 and Pfs25; in combination with at least one or both of the vaccinia host range gene K1L and DNA encoding Flagellin, or at least an operable binding portion of Flagellin. Advantageously, the recombinant poxvirus NYVAC contains the K1L gene providing the capacity for limited replication in humans, yet retaining attenuated virulence; and, this NYVAC contains DNA coding for and expresses the CSP, PfSSP2, LSA1-repeatless, MSA-1, SERA, AMA-1, Pfs25, ABRA, Pfhsp70, or Pfs16, *P. falciparum* antigens, and advantageously this NYVAC that contains K1L and the foregoing DNA encoding *P. falciparum* antigens also contains DNA encoding Flagellin, or an operable binding portion of Flagellin. While such is an advantageous embodiment, the invention comprehends recombinant poxviruses, e.g., NYVAC, expressing one or more or only some of these *P. falciparum* antigens, as well as Flagellin or an operable binding portion thereof and/or K1L. The foregoing *P. falciparum* antigens individually or in combinations can be expressed by single poxvirus vectors (e.g., NYVACs) that also contain and express Flagellin, or an operable binding portion of Flagellin and also advantageously K1L, and these single poxvirus vectors can be used in combination with each other in an immunogenic, immunological or vaccine composition.

The invention also comprehends poxvirus, e.g., NYVAC single recombinants expressing the CSP, PfSSP2, LSA1-repeatless, SERA, or MSA-1 N-terminal p83 and C-terminal gp42 processing fragments in combination with at least one of the genes K1L and flagellin or an operable binding portion of Flagellin.

The invention is also directed to the methods of making and using the replication competent poxvirus expressing malaria or *Plasmodium* genes for the production of *Plasmodium* gene products, either in vivo or in vitro as well as to the recombinant gene products.

In a further aspect, the invention relates to a composition for inducing an immunological response in a host animal inoculated with the composition. The composition can include an adjuvant for the induction of innate immunity. The composition can contain a synthetic or engineered or non-naturally occurring or recombinant poxvirus, e.g. NYVAC, that contains, advantageously in a nonessential region thereof, DNA encoding one or more antigens or immunogens, e.g., one or more *Plasmodium* antigens or immunogens, and Flagellin or an operable binding portion thereof, and optionally also K1L, as well as to methods for inducing such an immunological response in an animal by inoculating or administering to the animal the composition or a poxvirus of the composition. The immunological response can be a protective immunological response and hence the composition can be a vaccine; but, it need not elicit a protective immune response and can be an immunogenic or immunological composition. Advantageously, DNA in the poxvirus codes for and the poxvirus expresses one or more and advantageously all of SERA, ABRA, Pfhsp70, AMA-1, Pfs25, Pfs16, PfSSP2, LSA-1, LSA-1-repeatless, MSA-1, CSP, MSA-1 N-terminal p83 and MSA-1 C-terminal gp42 of Plasmodium, in combination with the Flagellin or at least an operable binding portion of Flagellin, and K1L. A portion of Flagellin that is essential to trigger the TLR5 PAMP is an operable binding portion of Flagellin. With such a poxvirus, a plurality of *Plasmodium* genes is advantageously co-expressed in the host or animal, e.g., CSP, PfSSP2, LSA-1-repeatless, MSA-1, SERA, AMA-1, and Pfs25; and preferably the poxvirus contains the host range gene K1L and also expresses Flagellin or an operable binding portion thereof; and, preferably the poxvirus is a NYVAC poxvirus. Such a poxvirus has the capacity for limited replication in mammals, e.g., humans while retaining the attenuated virulence profile. Accordingly, animals or hosts in this description are advantageously mammals, such as humans.

Furthermore, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following Detailed Description, given by way of example, but not intended to limit the invention solely to the specific embodiments described, may best be understood in conjunction with the accompanying drawings, incorporated herein by reference, wherein:

FIG. 1 discloses "IKSRR" as SEQ ID NO: 6.

FIG. 2A shows the K1L expression cassette nucleotide sequence (SEQ ID NO: 20).

DETAILED DESCRIPTION

Poxvirus Vectors

Figure 1:
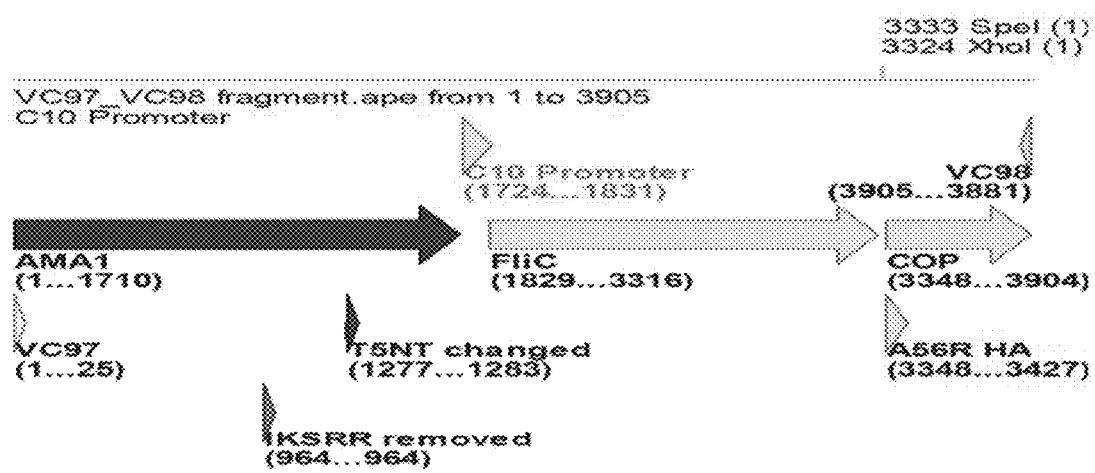
FIG. 1 shows primer locations with regard to Example 1.

The success of the smallpox eradication campaign is an unprecedented medical achievement. (Henderson D A. Sci. Am 1976:235; 25-33) However, there were serious adverse effects that posed substantial risks to subpopulations of vaccine recipients. These risks were associated with the use of virulent replication competent vaccine strains of poxvirus for immunization. These vaccine strains posed especially significant risks for those recipients, and close contacts, with abnormalities in cutaneous immunity and often caused life-threatening post vaccination adverse events. The nature and frequency of these events have been well documented. (Bray, M Antiviral research 2003; 58: 101-14, Engler, R J M J. Allergy Clinical Immunology 2002; 110: 357-65, Halsell J S JAMA 2003; 289: 3283-9, Kretzschmar, M. Plos Medicine 2006; 3(8): 1341-51, Casey, C G. JAMA 2005; 294: 2734-43). Although significant risks were associated with vaccination against smallpox, these risks were acceptable in the light of the horrific pandemic smallpox posed to public health.

Concomitant with the announcement from the World Health Organization that smallpox had been eradicated, and the advent of recombinant molecular technologies, there was renewed interest in vaccinia as a recombinant eukaryotic expression vector, with the capacity to carry and deliver heterologus target genes of interest. (Panicali, D. Proc. Natl. Acad. Sci. 1982; 79; 4927-493, Panicali D. Proc. Natl. Acad. Sci. 1983; 80(17): 5364-8, Mackett, M. Proc. Natl. Acad. Sci. 1982; 79: 7415-7419, Smith G L. Proc. Natl. Acad. Sci. 1983; 80(23): 7155-9, Smith G L. Nature 1983; 302: 490-5, Sullivan V J. Gen. Vir. 1987; 68: 2587-98). Importantly, these pivotal studies provided the foundation highlighting the potential of recombinant vaccinia as a novel vaccine vector having the attributes of genomic stability, ease of genomic manipulation and amplification and importantly, robust storage stability, critical to address the significant unmet needs for improved tropical disease vaccines such as malaria in underdeveloped, third world countries.

In addition to its long-standing history of use in humans, the ability to generate synthetic recombinants expressing of any number of antigens or combinations thereof, vaccinia provides an exciting new avenue for the generation of recombinant vaccines, perhaps with the potential to be the "universal immunization vehicle". (Perkus M Journal of Leukocyte Biology 1995; 58:1-13). Recombinant vaccinia vectors were rapidly embraced by the veterinary industry for the development of new vaccine technologies. (Yilma T D. Vaccine 1989; 7: 484-485, Brochier B. Nature 1991; 354: 520-22, Wiktor, T J. Proc. Natl Acd. Sci. 1984; 81: 7194-8, Rupprecht, C E. Proc. Natl Acd. Sci. 1986; 83: 7947-50, Poulet, H Vaccine 2007; 25(July): 5606-12, Weyer J. Vaccine 2009; 27(November): 7198-201). However, the well documented safety issues as a vaccine in humans would remain a major hurdle that had to be addressed if recombinant vaccinia vectors were to gain regulatory approval for use in the general human population. It is with these safety concerns that rigorous ongoing clinical safety testing continues today. Further compounding safety concerns for live viral vaccines, is the fact that a significant proportion of our population is highly immuno-compromised though a variety of medical conditions such as cancer and HIV infection. (Parrino J. J. Allergy Clin. Immunol. 2006; 118(6): 1320-26, Jacobs B L. Antiviral Therapy 2009; 84(1): 1-13.) To date, there are no licensed recombinant poxvirus vaccines for use in humans. (Rollier C S. Curr. Opin. Immun. 2011; 23(June): 377-82.)

Poxvirus Attenuation for Improved Viral Vaccine Vectors

A great deal of work has focused on the development of attenuated vaccinia virus strains. Laboratory studies have demonstrated that the deletion of certain vaccinia genes reduces the virulence of resulting recombinants in animal models (Buller, R M Nature 1985; 317(6040): 813-5, Buller R M. J. Virol. 1988; 62(3):866-74, Flexner, C. Nature 1987; 330(6145): 259-62, Shida, H. J. Virol. 1988; 62(12): 4474-80, Kotwal, G J. J. Virol. 1989; 63(2): 600-6, Child, S J. Virology 1990; 174(2): 625-9.). Two highly attenuated strains of vaccinia, Modified Vaccinia Ankara (MVA) and NYVAC have emerged as two of the most predominately studied, non-replicating vectors in human tissues. Recombinants of both MVA and NYVAC have been extensively studied pre-clinically and many have made their way through late phase II/III clinical trials. Both viruses have been extensively studied and characterized at the genomic level.

MVA was developed during the 1970s, by high serial passage of vaccinia Ankara on primary chicken embryo fibroblasts (CEF). The high serial passage resulted in many large genomic deletions totaling some 30 kb and importantly, the loss of the ability of the virus to replicate in humans and other mammals. (Mayr A. Zentralbl Bakteriol 1978; 167(5,6): 375-9, Antoine G. Virology. 1998; 244(2): 365-96, Wyatt, L S. Virology 1998; 251(2): 334-42, Sancho, M C. J. Virol. 2002; 76(16): 8313-34, Gallego-Gomez, J C. J. Virol. 2003; 77(19); 10606-22). The NYVAC strain was derived from a plaque isolate of the Copenhagen strain of vaccinia by the precise deletion of 18 open reading frames (ORFs) that were implicated in pathogenesis, virulence and host range regulatory functions. (Goebel S J. Virology 1990; (a,b) 179: 247-66, Tartaglia, J. Virol. 1992; 188(1): 217-32, U.S. Pat. No. 5,762,938, Najera J L. J. Virol. 2006; 80(12): 6033-47).

MVA and NYVAC strains have been directly compared in preclinical studies as to the capacity to replicate in animal models and in the clinical settings assessing the safety profile in extensive human trials. (Najera, J L. J. Virol. 2006; 80: 6033-6047, Gomez, C E. J. Gen. Virol. 2007; 88: 2473-78, Mooij, P. Jour. Of Virol. 2008; 82: 2975-2988, Gomez, C E. Curr. Gene Ther. 2011; 11: 189-217.) While avirulent and non-replicating, these vaccine vectors have repeatedly demonstrated their safety attributes but importantly, they are still competent in stimulating both cellular and humoral immune responses against a variety of expressed target antigens. (Cox, W. Virology 1993; 195: 845-50, Perkus, M. Jour. Of Leukocyte Biology 1995; 58: 1-13, Blanchard T J. J Gen Virology 1998; 79(5): 1159-67, Ockenhouse C F. J. Infec. Dis. 1998; 177: 1664-73, Amara R. Science 2001; 292: 69-74, Hel, Z., J. Immunol. 2001; 167: 7180-9, Gherardi M M. J. Virol. 2003; 77: 7048-57, Didierlaurent, A. Vaccine 2004; 22: 3395-3403, Bissht H. Proc. Nat. Aca. Sci. 2004; 101: 6641-46, McCurdy L H. Clin. Inf. Dis 2004; 38: 1749-53, Earl P L. Nature 2004; 428: 182-85, Chen Z. J. Virol. 2005; 79: 2678-2688, Najera J L. J. Virol. 2006; 80(12): 6033-47, Nam J H. Acta. Virol. 2007; 51: 125-30, Antonis A F. Vaccine 2007; 25: 4818-4827, B Weyer J. Vaccine 2007; 25: 4213-22, Ferrier-Rembert A. Vaccine 2008; 26(14): 1794-804, Corbett M. Proc. Natl. Acad. Sci. 2008; 105(6): 2046-51.)

The body of clinical data from late stage human trials for recombinant MVA, NYVAC and other non-replicating poxvirus vectors is growing significantly. Many of these studies have focused on two of the most challenging areas for vaccine development, cancer immunotherapeutics (Kaufman H L., J. Clin. Oncol. 2004; 22: 2122-32, Amato, R J. Clin. Cancer Res. 2008; 14(22): 7504-10, Dreicer R. Invest New Drugs 2009; 27(4): 379-86, Kantoff P W. J. Clin. Oncol. 2010, 28, 1099-1105, Amato R J. J. Clin. Can. Res. 2010; 16(22): 5539-47, Kim, D W. Hum. Vaccine. 2010; 6: 784-791, Oudard, S. Cancer Immunol. Immunother. 2011; 60: 261-71.) and HIV. (Wyatt, L S. Aids Res. Hum. Retroviruses. 2004; 20: 645-53, Gomez, C E. Virus Research 2004; 105: 11-22, Webster, D P. Proc. Natl. Acad. Sci. 2005; 102: 4836-4, Huang, X. Vaccine 2007; 25: 8874-84, Gomez, C E. Vaccine 2007a; 25: 2863-85, Esteban M. Hum. Vaccine 2009; 5: 867-871, Gomez, C E. Curr. Gene therapy 2008; 8(2): 97-120, Whelan, K T. Plos one 2009; 4(6): 5934, Scriba, T J. Eur. Jour. Immuno. 2010; 40(1): 279-90, Corbett, M. Proc. Natl. Acad. Sci. 2008; 105: 2046-2051, Midgley, C M. J. Gen. Virol. 2008; 89: 2992-97, Von Krempelhuber, A. Vaccine 2010; 28: 1209-16, Perreau, M. J. Of Virol. 2011; October: 9854-62, Pantaleo, G. Curr Opin HIV-AIDS. 2010; 5: 391-396).

Overall the safety data is excellent with minimal vector associated side effects, this being of great significance considering the inherent risk associated with a large portion of the target population for cancer and HIV vaccines that are potentially immunocompromised. Importantly, when scoring vaccine efficacy, the overwhelming body of clinical data suggests NYVAC and MVA and other attenuated poxvirus vectors are capable of eliciting important correlative immune responses, to a degree that is both encouraging and supportive for continued development and testing of these vectors. However, studies surrounding both cancer and HIV vaccine initiatives indicate that while immune responses from vaccine recipients are indeed encouraging, many late phase trials have failed to achieve the primary objectives necessary to go forward with further clinical development. To this point, the data surrounding vaccine induction of only weak or suboptimal immune correlatives remain the focus in assessing these failures. (Smith, J M. AIDS Res. Hum. Retroviruses 2004; 20: 1335-1347, Hanke, T. J. Gen. Virol. 2007; 88: 1-12, Sandstrom, E. J. Inf. Dis. 2008; 198: 1482-90, Walker, B D. Science 2008; 320: 760-4, Sekaly, R P. J. Exp. Med. 2008; 205: 7-12. Rerks-Ngarm S. 2009; N Engl J Med 361: 2209-2220.).

If recombinant vaccines targeting weakly immunogenic antigens eg., cancer Tumor Associated Antigens (TAAs) and HIV are to be effective there has to be a renewed effort focused on improving and developing second generation MVA and NYVAC viral vectors. Clearly improvements need to be focused at enhancing viral expression, possibly through more robust vaccine amplification profiles in humans, while retaining an attenuated phenotype essential for the safety of vaccine recipients. Developmental work has focused on a variety strategies including: further genomic modifications to non-replicating viral vectors such as NYVAC and MVA, routes of vaccine administration, immunization priming protocols, co-expression of immuno-stimulatory signaling molecules and novel adjuvant strategies for enhanced immunogenicity.

Further Modifications to NYVAC to Elicit Stronger Immunogenic Responses

One method of enhancing expression of target antigens from NYVAC is to re-engineer NYVAC to allow the virus to proceed later into the infectious cycle, potentially providing some limited level of avirulent replication. Importantly, replication competence does not have to exclude attenuation. (Parker S D. 2007: Vaccine 25; 6764-73) Ideally, this level of replication would be enhanced compared to NYVAC but less than that obtained from the parent Copenhagen strain. More robust replication and expression may provide more antigen load for processing and importantly, better mimicking of the naturally occurring viral infectious cycle, potentially triggering stronger innate immune responses. There are several examples of attenuated recombinant vaccinia vectors that have been engineered as avirulent but importantly, replication competent, while exhibiting nearly the same margin of vaccine safety of the replication deficient NYVAC strain. (Verardi, P H. J. Virol. 2001; 75(1): 11-8, Langland, J O. Virology 2002; 299(1): 133-41, Langland, J O. Virology 2004; 324(2): 419-29, Langland, J O. J. Virology 2006; 80(20): 10083-95, Legrand, F A. Proc. Natl. Acd. Sci. 2005; 102(8): 2940-5, Denes, B. J. Gene Med. 2006; 8 (7): 814-23, Day, S L. J. Immunol. 2008; 180(11): 7158-66, Jacobs, B L, Antiviral Res. 2009; 84: 1-13, Vijaysri, S. Vaccine 2008; 26: 664-676, Dai, K. Vaccine 2008; 26: 5062-71, Huang, X. Plos One 2009; 4: e4180.)

Virally encoded genes that were specifically deleted from Copenhagen to generate NYVAC or lost upon serial passage in primary chick cells in generating MVA, were predominately viral gene functions that had evolved particularly for the modulation and or inhibition of antiviral host immune responses. Such factors are referred to as pathogenicity factors. These factors can determine viral host range, pathology and virulence in a given host. (McFadden G. Nat. Rev. 2005; 3: 201-13.) The focus of a large body of research has been devoted to study these virulence factors and their importance in determining host range. The understanding of how these host range genes interact with specific host targets has elucidated functionality with respect to viral pathogenesis and the abrogation of specific host immune responses. There are approximately 12 different host range gene families that have been identified in poxviruses. (Werden, S J. Adv. Vir. Res. 2008; 71: 135-171, Bratke, K A. Inf. Gen. and Evol. 2013; 14: 406-25). Many attempts to enhance immunogenicity profiles of NYVAC or MVA based vaccines have looked to restore different host range gene iterations that were originally deleted from these highly attenuated vectors. In light of the comparative studies using traditional replication competent and replication deficient NYVAC and MVA vectors, it was evident that long lasting immune responses were more robust upon immunization using the tradition first generation replication competent vaccinia vector. (Ferrier-Rembert, A. Vaccine 2008; 26: 1794-1804) Furthermore, coupled with suboptimal clinical trials in humans (Rerks-Ngarm, 2009) with non-replicating vaccinia based vectors, it has been proposed by several in the field that replication deficient vectors while providing an excellent safety profile, may not provide enough antigen load to stimulate robust, long lasting, adaptive immune responses in some cases and that some level of viral replication would provide a more potent vaccine immunogen.

Host range genes C7L and K1L previously identified have been the obvious targets of choice to reinsert back into the attenuated genome of NYVAC to enable the virus to proceed further into its replicative cycle. (Perkus, M E. Virology 1990; 170: 276-86, Tartaglia, J. Virology 1992;188: 217-232, Shisler, J L. J. Virol. 2004; 78: 3553-60, Bradley, R R. Virus Res. 2005; 114: 104-12). C7L is known to inhibit host antiviral action induced by type I interferons. (Meng, X J. Virol. 2009; 83: 10627-636, Backes, S. J. Gen. Virol. 2010; 91: 470-482). Additionally, C7L and K1L inhibits the phosphorylation of eIF2 alpha and the induction of apoptosis, through the inhibition of PKR activity in infected cells. (Najera, J L. J. Virol 2006; 80: 6033-47, Willis, K L. Virology 2009; 394: 73-81). Specifically, when C7L was engineered back into NYVAC the resulting modified NYVAC-C7L virus was found to be replication-competent in both human and murine cells. In vivo, mouse models have been used to demonstrate enhanced viral expression, while maintaining an attenuated profile, with clearly superior immune responses against expressed HIV antigens in comparison with the host restricted NYVAC vector (Najera, J L. J. Virol. 2006; 80: 6033-47, Najera, J L. 2010;). In another example, genomic modification of NYVAC was taken one step further with the re-insertion of both C7L and K1L, furthermore with an additional modification of removing B19R, a type I INF inhibitor (Kibler, K V. 2011; Gomez, C E. Jour. Of Virol. 2012; 5026-38). The NYVAC vector containing both C7L and K1L (NYVAC+C7L, K1L), as expected, was found to be replication competent in a variety of different cultured human cells. Importantly, (NYVAC+C7L, K1L) was found to still retain the highly attenuated phenotype in comparison to wild type replication competent strains, such as Copenhagen and NYCBH. Bio-distribution analysis indicated that other genomic modifications such as the deletion of B19R allowed for further attenuation compared to (NYVAC+C7L, K1L), potentially through the activation of PKR through INF I activation, resulting in the induction of the pathogen-associated molecular pattern (PAMP) sensors. (Kibler, K V. 2011)

A specific inventive embodiment of the invention is NYVAC or another attenuated (as to mammals) poxvirus containing the Host Range gene K1L, e.g., NYVAC vectors modified to contain the host range gene K1L (NYVAC+K1L) so that these vectors are further developed to specifically replicate in human tissues to a level intermediate of that of the more virulent parental replication competent strain Copenhagen and the replication deficient stain NYVAC or MVA or MVA-BN or canarypox or fowlpox or ALVAC or TROVAC, and to co-express at least one vaccine target antigen(s). Advantageously such a vector also contains DNA coding for and expresses Flagellin or an operable binding portion thereof.

Methods to Enhance Immune Responses to Vaccines

Routes of Vaccine Delivery

Considering the suboptimal results obtained with the attenuated vectors NYVAC and MVA in the HIV trials, alternatives are sought to address these limitations with hopes of enhancing efficacy. Extensive studies have been done directly comparing MVA and NYVAC in tissue culture, (Najera et al., 2006) genome profiling studies, (Guerra et al., 2004, 2006,) and immunogenicity in human clinical trials (Gomez et al., 2007a, b). Importantly, studies comparing inoculation route and ability of the virus to disseminate in vivo have been done. (Gomez, C E. 2007; 88: 2473-2478, Gomez, C E. Vaccine 2007b: 25; 1969-92). Although NYVAC and MVA are highly attenuated they both exhibit differences in vitro and in vivo, potentially with immunological relevance (Mooij, P. J. Virol. 2008; 82(6): 2975-88.)

The normal mode of viral transmission for many viruses, including HIV and Sars CoV, is through mucosal surfaces. It is believed that cell-mediated responses at mucosal sites are critical for protection. Clinical data from some of the initial studies was unclear as to whether or not immunization with cutanous or intramuscular routes can result in important cellular responses at distal surface mucosal sites. (Benson, J. 1998; J. Virol. 72: 4170-82, Belyakov, I M. J. Clin. Invest 1998; 102: 2072-2081, Cromwell, M A. J. Virol. 2000; 74: 8762-66, Stevceva, L. Genes Immun. 2000; 1: 308-15, Hel, Z. J. Immunol. 2001; 167: 7180-91, Stittelaar, K J. Vaccine 2001; 19: 3700-09, Stevceva, L. Jour. Of Virol. 2002; 76(22): 11659-76.). Several recent studies indicate mucosal routes of vaccination may be advantageous. (Huang, X. Vaccine 2007; 25: 8874-84, Gherardi, M M. J. Gen. Virol. 2005; 86: 2925-36, Neutra, M R. Nat. Rev. Immunol. 2006; 6:148-158, Karkhanis, Curr. Pharm. Des 2007; 13: 2015-23, Corbett, M. Proc. Natl. Acad. Sci. 2008; 105(6): 2046-51, Belyakov, I M. J. Immunol. 2009; 183: 6883-6892.) Furthermore, mucosal routes of inoculation seem to be effective at overcoming preexisting immunity. Strong anti-vector responses can result in diminished antigen load of expressed antigenic targets, therefore potentially limiting adaptive immune responses. (Naito, T. J. Gen. Virol. 2007; 88: 61-70.)

Immunization Priming

Prime boost is routinely used in vaccination protocols to increase the immune response. Classical immune studies have shown that the immune system once activated and allowed to rest then reactivated will result in a significant boost to both B-cell and T-cell responses. (Murphy, K. Janesway C. Immunology $7^{th}$ ed. 2008; New York, N.Y.) When using the same live recombinant virus vector repeatedly to direct antigen expression by host cells, strong anti-vector immune response (induced by the priming vaccine) can block efficacy of the following boost. Essentially, the boost vaccine is quelled before viral expression from host cells can express foreign protein, along with immune signals and therefore provides little advantage to the original vaccination. To overcome the vector-specific immunity, it is critical to use a different vector for the boost. Prime boost protocols are well known in the art. (Hu, S L. Science 1992; 255: 456-459, Richmond, J F L. Virology 1997; 230: 265-274, Brown, S. Viruses 2010; 2: 435-467) Prime boost regimens expressing the antigens of interest from another vector system, such as DNA, then boosting with the recombinant virus vector have enhanced vaccine efficacy (Ramsay, A J. Immunol. Cell Biol. 1997; 75: 382-388, Ramshaw, I A. Immunol. Today 2000; 21: 163-165, Estcourt, M J. Int. Immunol. 2002; 14: 31-37, Hodge, J W. Can. Res. 2003; 63(22):7942-9, Woodland, D L. Trends Immunol. 2004; 25(2): 98-104, Webster, D P. Proc. Nat Acad. Sci. USA 2005; 102(13): 4836-41, Harari, A J. Exp. Med. 2008; 205: 63-77, Melief, C J M. 2008; Immunity 29: 372-83, Brave, A. Mol. Ther. 2007; 15: 1724-1733, Robinson, H L. Hum. Vaccine 2009; 5: 436-438, Gudmundsdotter, L. Vaccine 2009; 27: 4468-4474. Ishizaki, H J. Immunother. 2010; 33(6): 609-17, Krupa, M. Vaccine 2011; 29(7): 1504-13).

Significantly, for recombinant NYVAC and MV A vectors, much of the late stage clinical data focuses on HIV vaccines. Clearly, for an ideal HIV vaccine it is important to stimulate both arms of the adaptive immune system eliciting strong cellular immunity, memory cells and antibodies at mucosal surfaces and throughout the body. (Demberb, T. Int. Rev. Immunol. 2009; 28(1): 20-48, Neutra, M R. Nat. Rev. Immunol. 2006; 6:148-158.). Additionally clinical studies have shown that the ability to contain HIV virus load correlates strongly with robust cellular CD8+ T-cell responses. (Dorrell, L. Vaccines 2005; 4(4): 513-20, Kuroda, M J. 1999; 162: 5127-33, Shen, X. J. Immunol. 2002; 169: 4222-29, Carrington, M. Ann. Rev. Med. 2003; 54: 535-51, Frahm, N. J. Virol. 2005; 79: 10218-25, Dorrell, L. J. Virol. 2006; 80(10): 4705-16, Dorrell, L. Vaccine 2007; 25: 3277-83, Frahm N. Nat. Immunol. 2006; 7: 173-8, Wilson N A. J. Virol. 2006; 80: 5875-85, Harari, A J. Exp. Med. 2008; 205: 63-77, McCormack, S. Vaccine 2008; 26: 3162-74, Mooij, P J. Virol. 2008; 82: 2975-88, Van Montfoort, N. Proc. Natl. Acad. Sci. 2009; 106; 6730-35, Quakkelaar E D. Plosone 6; 2011: e16819) Clearly immunization regimens and modes of antigen delivery that stimulate both arms of the adaptive immune system, would provide a clear advantage in recombinant vaccine design. (Dorrell, L. 2005 and 2007, Sekaly, R P. J. Exp. Med. 2008; 205: 7-12)

Immuno-Stimulatory Gene Expression as An Adjuvant

Co-Stimulation Molecules

Another approach to optimizing immunization is through T-cell co-stimulation. T-cell activation depends on the interaction of MHC peptide complexes with T-cell receptors, along with the interaction of co-stimulatory molecules with antigen presenting cells (APC) and the corresponding receptors on T-cells. Co-stimulation is particularly important when expressed antigens are only poorly immunogenic such as TAAs. The use of co-stimulatory molecules such as B7.1, the ligand for T-cell surface antigens CD28 and CTLA-4 and a triad of human co-stimulatory molecules (TRICOM) have been studied extensively. (Damle, N K. J. Immunol, 1992; 148: 1985-92, Hodge, J W. Can. Res. 1999; 59: 5800-7, Von Mehren, M. Clin. Cancer Res. 2000; 6: 2219-28, Lu, M. Proc. Natl. Acad. Sci. 2004; 101(supp12): 14567-71, Gulley, J L. Clin. Can. Res. 2005; 11: 3353-62, Arlen, P M. J. Urol. 2005; 174: 539-46, Nam, J H. Acta. Virl. 2007; 51: 125-30, Madan, R A. Exp. Opin. Invest. Drugs 2009; 18: 1001-11). The data suggests enhanced immune responses through co-stimulatory molecules leads to sustained activation and signaling in T-cells. Furthermore, it has been suggested that co-stimulation increases CTL avidity resulting in more effective targeted cell lysis (Oh, S. J. Immunol. 2003; 170: 2523-30, Hodge, J W. J. Immunol. 2005; 174: 5994-6004,). Innate immune activation can drive co-stimulatory molecule expression.

Cytokines

The rational for using an immune adjuvant is to enhance the immune response to a vaccine by interaction with Antigen Presenting Cells (APCs) and T-cells. The co-expression of a variety of cytokines such as GM-CSF, IL-2, and FLT-3 ligand, has been studied extensively. The co-expression of cytokines in the vicinity with targeted expressed antigens was found to enhance the recruitment of dendritic cells (DCs) to the site of immunization resulting in enhanced presentation to APCs. The co-expression of cytokines has been highly utilized in oncology based vaccines, to boost responses, again to poorly immunogenic TAAs. (Kass, E. Cancer Res. 2001; 61: 206-14, Davis, I D. J. Immunothere. 2006; 29: 499-511, Arlen, P M. J. Urol. 2007; 178: 1515-20, Lechleider, R J. Clin. Can. Res. 2008; 14: 5284-91, Gulley, J L. Can. Immunol. Immunother. 2010; 59: 663-74. Kantoff, P W. N. Eng. Jour. Med. 2010; 363-411-22, Lutz, E. Ann. Sur. 2011; 253: 328-35). Innate immune activation can drive cytokine expression.

Innate Immunity Activation

Role of Toll-Like Receptors in Innate Immunity

Immune responses have been classically categorized into innate and adaptive immunity. Adaptive responses are further subdivided into cellular and humoral. In comparative analysis of innate and adaptive responses, adaptive immunity is driven by the specificity of the T-cell and B-cell antigen specific receptors resulting in further induction of immune cell, cytokine and antibody trafficking to converge on the invading pathogen. Additionally, memory T and B-cell responses are generated so that any subsequent adaptive response to the same pathogen can be more rapidly regenerated (Janeway 2002). Innate immunity is found in all vertebrates. Originally, innate responses were viewed as a vestige of ancient host defenses and were simply used as an immediate host defense, a temporary and highly non-specific reaction until more important adaptive responses could take over. However, recent studies have shown that the innate immune system has a high degree of specificity with the ability to identify important signatures of foreign pathogens. The ability to identify signatures of foreign pathogens is associated with a highly conserved family of receptors designated, Toll-Like Receptors (TLRs) for their homology to the Toll protein identified in Drosophila (Lemaitre, B. Cell 86; 973-83).

TLRs are type one integral membrane glycoproteins, with an excellular domain having a leucine rich repeat region (LRR) and a cytoplasmic signaling domain. The LRR domain is important for ligand binding. (Akira, S. Phil. Trans R. Soc. B 2011; 366: 2748-55). Initial studies indicated that specific TLRs (TLR-4) were involved with the recognition of lipopolysaccharide (LPS), the cell wall component of gram-negative bacteria. The connection of mammalian TLRs with LPS recognition provided the important link necessary between TLRs and Pathogen-Associated Molecular Pattern (PAMP) recognition. (Poltorak, A. Science 1998; 282(5396): 2085-88, Qureshi, S T. J. Exp. Med. 1999; 189(4): 615-25. Hoshino, K. J. Immunol. 1999; 162 (7): 3749-52).

To date, 12 members of the TLR family have been identified in mammals. (Akira, S. Cell 2006; 124: 783-01, Beutler, B. Nature 2004; 430: 257-63, Medzhitov, R. Nature 2007; 449: 819-826). TLRs can recognize a variety of components derived from bacteria and viral pathogens. In addition to LPS a cell wall component, bacterial and viral DNA are recognized through (CpG) by TLR-9 (Hemmi, H. Nature 2000; 408: 740-5.), ssRNA by TLRs 7 and 8 (Hemmi, H. Nat. Immunol. 2002; 3: 196-200, Diebold, S. Science 2004; 505: 1529-31.) dsRNA by TLR-3 (Alexopoulou, L. Nature 2001; 413: 732-38.) and bacterial proteins such as Flagellin, a component of bacterial Flagella. Flagella are responsible for bacterial motility, and are detected by TLR-5 (Hayashi, F. Nature 2001; 410: 1099-1103, Uematsu, S. Nat. Immunol. 2006; 7: 868-874.) TLRs can be divided as to cellular localization, TLR 1,2,4-6 are on the cell surface, TLR 3,7-9 are within endosomes. (Kumar H. Biochem. Biophy. Res. Commun. 2009; 388: 621-5).

Once triggered by the TLR specific ligand, the signaling process occurs through adapter molecules called TIR-Domain containing inducing interferon-B (TRIF) or Myeloid Differentiation Primary Response Gene (MyD88). This results in cytosolic signaling complexes through TRIF and MyD88 activating NF-KB and IRF transcription factors resulting in the production of inflammatory cytokines and type I interferon (IFN). (Yamamoto M. Science 2003; 301 (5633): 640-3, Kawai T. Semin. Immunol. 2007; 19(1): 24-32. O'Neill L A. Nat. Rev. Immunol. 2007; 7: 353-64.) Furthermore, activation of these transcription factors results in the activation of the complement and coagulation cascades and induction of phagocytosis and apoptosis. (Adams, S. Immunotherapy 2009; (6): 949-64) All these processes play a critical role in initiating innate and adaptive arms of immune protection. (Hoebe K. Nat. Immunol. 2004; 5(10): 971-4. Akira S. Nat. Immunol. 2001; 2(8): 675-80, Medzhitov, R. Nature 1997; 388(6640): 394-7.)

Toll-Like Receptors and Viral Infection

Initial evidence that TLRs were involved in controlling viral infection came from the finding that some viruses expressed genes specifically targeting and blocking TLR signaling responses. TLRs have been shown to be involved in antiviral responses to a wide variety of virus families, in context with many different viral macromolecules; the list is long and reviewed extensively (Carty, M. Clinical and Exp. Immunol. 2010; 161: 397-406). Plasmacytoid dendritic cells (pDC) are specialized immune cells that produce type I IFN and are critical for antiviral responses. (Gilliet M. Nat. Rev. Immunolo. 2008; 8: 594-606, Theofilopoulos A N. Ann. Rev. Immunol. 2005; 23: 307-36). It has been shown that TLRs 7 and 9 signaling by viral nucleic acids in the endosome promotes activation of pDCs. TLR9 detects CpG in DNA, while TLRs 7 and 8 detect G/U rich ssRNA. (Diebold S S. Science 2004; 303: 1529-31, Krieg A M. Ann. Rev. Immunol. 2002; 20: 709-60, Heil F. Science 2004; 303: 1526-29). TLR 7-9 signaling is mediated through adaptor MyD88. (Akira S. Nat. Rev. Immunol. 2004; 4: 499-511.)

Vaccinia has been shown to activate pDCs upon infection. In human cells such as monocytes, macrophages and keratinocytes, activation of NF-KB is mediated through TLR 2, 3 and 4. (Bauernfeind, F. Nat. Immunol. 2009; 10: 1139-41, Howell, M D. Immunity 2006; 24: 341-8, Carty, M. Clinical and Exp. Immunol. 2010; 161: 397-406). In comparison, in mice, A/T rich viral DNA was detected by TLR 8, resulting in INF responses from activated pDCs. (Martinez, J. Proc. Nat. Acad. Sci. 2010; 107: 6442-7.) Importantly, this response in mice was shown to be independent of TLR-9. Interestingly, human pDCs do not express TLR8, only TLR-7 and 9. However, human conventional DCs do express TLR8 and these may play a role in IFN responses. (Iwasaki A. Nat. Immunol 2004; 5: 987-95.) It is important to note that vaccinia encodes several genes targeting modes of TLR signaling. A46R has been shown to inhibit the activity of MyD88, while A52R and C4L inhibits TLR mediated NF-KB activation. (Stack, J. J. Exp. Med. 2005; 201: 1007-18, Maloney, G. J. Biol. Chem 2005; 280: 30838-44, Stuart W. Jour. Gen. Virol. 2012; 93: 2098-108.) Other viruses have developed methods to block TLR activity. HCV has been shown to inhibit TLR signaling though the activity of its protease NS3/4a that cleaves the TRIF complex while NS5a directly inhibits MyD88. (Li, K. Proc. Nat. Acad. Sci. 2005; 102: 2992-7, Abe T. J. Virol. 2007; 81: 8953-66.)

TLRs Expression Profile

TLRs lie at the forefront of the host defense system, and provide a system wide network for the detection of pathogens. In humans, the network of 10 different expressed TLRs have been determined for a variety of different cell types. Importantly, TLRs are found not only on cells of the immune system but are also expressed on epithelial cells of the intestine, urogenital and respiratory tracts, areas potentially important to the site of invading pathogens. (Guillot, L. J. Bio. Chem. 2004; 280: 5571-80, Vora, P. J. Immunol. 2004; 173(9): 5398-405.) The TLR expression profile by cell type has been well established; mDCs express TLRs (1-6, 8), pDCs express TLR (7, 9), neutrophils express TLR (1, 2, 4-10), NK cells express TLR1, monocytes express all except TLR3, B-lymphocytes express TLR (9,10), activated T-cells express TLR 2, regulatory T-cells express TLR (8, 10). (Kadowaki, N. J. Exp. Med 2001; 194(6): 863-869, Bemasconi, N L. Blood 2003; 101(11): 4500-04, Hayashi, F. Blood 2003; 102(7): 2660-69, Muzio M. J. Immunol. 2000; 164 (11): 5998-6004, Hasan, U. J. Immunol. 2005; 174(5): 2942-50, Peng, G. Science 2005; 309(5739): 1380-84.)

TLR Agonists Important for Designer Vaccine Adjuvants

Having the information as to the TLR specific activating ligand and the complement of TLRs expressed on different cell types, it is now possible to specifically target TLRs by using activating ligands in vaccine formulations as adjuvants to enhance vaccine immunogenicity. In such a designer vaccine, it is possible to incorporate TLR activating components for vaccine optimization; as to site or route of vaccine inoculation (dermal, mucosol intranasal), type of desired immune response (cellular, humoral or both, TH1 or 2), type of vaccine (subunit, viral or bacterial, live, killed). In the present example, using live recombinant vaccinia vectors that naturally activate virus specific TLRs it would be of significant advantage to co-express one or more additional TLR ligand(s) (or at least the operable binding portion of that ligand) to recruit additional TLR activation providing an adjuvanting effect to further stimulate immune responses to the vaccine. It is critically important to recognize the tight regulation dictated by activation of the innate immune system to control a specific class of infection and limit immune response induced damage to the host. For example, viral innate immune activation can induce interferon and programmed cell death while bacterial innate immune activation can induce reactive oxygen species and promote cell survival; adaptive immune responses follow this pattern. Innate immune activation is optimized for each class of infection that directs appropriate acquired immune responses to similar infections. Most immune responses to antigens expressed by a viral vector, such as NYVAC, would be expected to be anti-viral. However, novel inclusion of a bacterial PAMP, such as flagellin, to a viral vector would induce the expected antiviral responses plus an additional array of anti bacterial responses this vaccine induction of two classes of innate responses should enhance the vigor and breadth of immune responses when encountering *Plasmodium* infection with induction of both antiviral and antibacterial responses (an unnatural response dictated by the nature of the novel vaccine). In the future, innate *Plasmodium* immune activators may be used to further enhance vaccine efficacy.

Flagellin, TLR5 Ligand as a Vaccine Adjuvant

Flagellin is the integral component of Flagella, structures that certain bacteria have that are responsible for motility. In isolates of *Salmonella* there are two genes that encode the flagellar antigens. FliC encodes phase I flagellin and FljB encodes phase II flagellin. (Zieg J. Science 1977; 196: 170-2.) Both the FliC and FljB encode N and C domains that form part of the flagellar structure. (McQuiston J R. J. Clin. Microbio. 2004; 42: 1923-32.) Importantly, both contain motifs that are recognized by TLR5.

In addition to flagellin detection by TLR5, there is a second flagellin detection system based on the NLRC4 inflammasome complex. (Zhao Y. Nature 2011; 477: 596-600.) The mechanism of NLRC4 inflammasome complex activation has been extensively studied. (Franchi, L. Nat. Immunol. 2006; 7: 576-682., Franchi, L. Eur. J. Immunol. 2007; 37: 3030-39, Miao, E A. Nat. Immunol. 2006; 7: 569-75., Miao E A., Proc. Nat. Acad. Sci. 2008; 105: 2562-67, Miao E A. Proc. Nat. Acad. Sci. 2010; 107: 3076-80). Activation of the inflammasome leads to release of mature IL-IM, IL-18, and pro-inflammatory cytokines. (Jordan, J A. J. Immunol. 2001; 167: 7060-68, Birrell M A. Pharmacol. Ther. 2011; 130: 364-70, Suttwala, F S. J. Exp. Med. 2007; 204: 3235-45). The components of the inflammasome are found in the cytosol, thus the signaling flagellin is detected in the cytosol. (Franchi L. Nat. Immunol. 2012; 13: 325-32.)

Interestingly, Flagellin the ligand for TLR5, has shown utility in vaccine formulations as an adjuvant. (Wang, B Z. J. Virol. 2008; 82: 11813-23, Huleatt, J W. Vaccine 2008; 26: 201-14, Le Moigne, V. Mol. Immunolo. 2008; 45: 2499-2507, Wang, B Z. Clin, and Vaccine Immunol. 2012; 19(8): 1119-25). Furthermore, Flagellin has been shown to be an effective adjuvant in physical association (formulation mixtures) within vaccine antigen preparations, or expressed as a fusion with targeted antigens or lastly, co-incorporated into viral particles with target antigens such as in virus-like particles, (VLPs). (Huleatt, J W. Vaccine 2008; 26: 201-14, Mizel, S B. Clin. Vaccine. Immunol. 2009; 16: 21-28, Wang, B Z. J. Virol. 2008; 82: 11813-23). The recognition of flagellin and TLR5 is not associated with the central variable region (Anderson-Nissen E. Proc. Nat. Acd. Sci. 2005; 102: 9247-52.). However, there are conflicting reports as to the importance of removing the hyperimmune central variable region. (Ben-Yedidia T. Immuno Lett. 1998; 64: 9-15, Nempont C. J. Immunolo. 2008; 181: 2036-43.) Interestingly, there are reports that suggest the adjuvant effects of Flagellin may drive specific mucosal immune responses, and furthermore suggestions are that these would be more effective via specific routes of immunization, e.g., mucosal surfaces such as intranasal. (De Filette M. Virology 2008; 337: 149-61, Liang B. J. Virol. 2001; 75: 5416-20).

Specific inventive embodiments of the invention accordingly include: Coexpression by a recombinant or synthetic or engineered or non-naturally occurring poxvirus of one or more exogenous or heterologous antigens or immunogens and one or more PAMP modulators as an adjuvant. Accordingly, the invention comprehends a poxvirus vector developed to specifically express the Flagellin PAMP responsible for activation of TLR5 for enhanced adaptive immune responses to co-expressed antigen(s) or immunogen(s). In certain embodiments the poxvirus is an attenuated (as to mammals) poxvirus, such as NYVAC, MVA, MVA-BN, canarypox, fowlpox, ALVAC, TROVAC. In such embodiments, to specifically target and trigger the Flagellin PAMP responsible for activation of TLR5 for enhanced adaptive immune responses to co-expressed antigen(s) or immunogen(s), the poxvirus contains DNA coding for and expresses the entire or operable binding portion of the bacterial protein Flagellin. The operable binding portion of the Flagellin, is the portion responsible for binding to and activating the TLR5 receptor, resulting in a cascade of immune stimulatory pro-inflammatory responses to the targeted vaccine antigen. The Flagellin or operable binding portion is expressed either as peptide or fusion with antigen(s) or immunigen(s) provides for a multiplicity of options; the key to Flagellin or operable binding portion thereof expression is that the Flagellin operably and specifically agonize TLR5 to further stimulate "adjuvant" adaptive immune responses to expressed antigen(s) or immunogen(s).

The invention thus comprehends a synthetic, engineered, recombinant or non-naturally occurring poxvirus, e.g., vaccinia, vector developed to specifically replicate in human tissues to a level intermediate of that of the parental replication competent strain, e.g., Copenhagen, and the replication deficient stain e.g., NYVAC, MVA, MVA-BN (e.g., via K1L being present in the vector) and further developed to co-express Flagellin or an operable binding portion thereof (e.g., to deliver the Flagellin PAMP responsible for activation of TLR5) and at least one antigen or immunogen for which an adaptive immune response is desired whereby the poxvirus provides agonist(s) for one or several TLRs, e.g., TLR5 and a resulting cascade of immune stimulatory pro-inflammatory responses to the antigen(s) or immunogen(s). In such embodiments NYVAC vectors are preferred.

Malaria

Malaria is considered one of the most important parasitic diseases in the world. It is estimated that malaria caused over 200 million clinical episodes worldwide resulting in 655,000 deaths, mostly African children (WHO Global Malaria Program 2011). Furthermore the economic losses are magnified as most of the endemic countries are impoverished, costing some 3 billion dollars in Africa alone. (Teklehaimanot A. J. Trop. Med. Hyg. 2007; 77(6): 138-44. There have been substantial efforts and resources directed to methods and approaches for control-intervention such as indoor spraying, insecticidal nets, rapid diagnostics for testing, especially pregnant woman and children (Aponte J J. Lancet 2009; 374(9700): 1533-44., Menendez C. Lancet Infect. Dis. 2007; 7(2): 126-35). However, as these control interventions programs have had a measured degree of success, it is with the realization that to substantially reduce disease costs and burden to society vaccines against malaria are crucial to reduce the morbidity and mortality of this disease. (Malaria Eradication: Vaccines PloS Med. 2011; 8(1): e1000398.) A focused effort and strategic goal was put forth by the international organization PATH, Malaria Vaccine Initiative (MVI), that by 2020 malaria vaccines provide 80% protective efficacy against *P. falciparum*. Importantly, if vaccines are to contribute to malaria eradication, they need to have an impact on preventing malaria transmission, these are known as transmission blocking vaccines.

Intensive malaria vaccine research has encompassed several decades and has yet to overcome substantial hurdles associated with complexities of the parasite life cycle, specifically, antigen expression during different parasite life stages and variability of antigens or important epitopes from different parasite isolates. Although many develop anti-parasitic immunity by repeated natural exposure, reproducing this by vaccination has been difficult. (Langhorne, J. Nat. Immunity 2008; 9: 725-32., Goodman A L. Ann. Trop. Med. Parasitol. 2010; 104: 189-211). Vaccine candidates have targeted the pre-erythrocytic liver stage, blood stage or transmission blocking stage. (Dubovsky F. In: Plotkin S A Vaccines 2004; p1283-9., Plos Med 2011; 8(1): e1000400., Aide P. Arch Dis. Child. 2007; 92(6): 476-9.)

In pre-erythrocytic vaccines, the immune response would direct antibodies to invading *Plasmodium* sporozoites delivered by mosquitoes and target infected liver cells with humoral and cellular immunity with the hope to prevent or limit parasites from entering red blood cells, thus avoiding clinical symptomology and any risk of further infection and transmission. Pre-erythrocytic vaccines were the first attempted modern vaccines against malaria, and currently the basis of the GlaxoSmithKline (GSK) RTS,S vaccine, the furthest along the clinical pipeline currently in phase III trials. (Nussenzweig R S. Nature 1967; 216(5111): 160-2., Rieckmann K H. Bull. WHO 1979; 57(Suppl. 1: 261-5.) The GSK vaccine uses the central repeat region of the circumsporozoite protein (CSP) and hepatitis B surface antigen (HBsAg) as an immunogenic carrier. Efficacy results of the RTS,S in adults and children are reviewed. (Bojang K A. Vaccine 2005; 23(32): 4148-57., Macete E. Trop. Int. Med. Health 2007; 12(1): 37-46., Alonso P L. Lancet 2004; 364(9443): 1411-20., Alonso P L. Lancet 2005; 366 (9502): 2012-8.) Several vaccines have focused on delivering attenuated sporozoites, or sporozoite antigens, through a variety of methods including viral vectors such as MVA. (Hoffman S L. J. Infectious Dis. 2002; 185(8): 1155-64., Bejon P. N. Jour. Med. 2008; 359:2521-32., Roestenberg M. Lancet 2011; 377(9779): 1770-6., Hoffman S L. Hum. Vacc. 2010; 6(1): 97-106., Hill A V. Philos. Trans. Soc. Lond. B. Biol. Sci. 2011; 366(1579): 2806-14., Liu M A. Immunity 2010; 33(4): 504-15., Draper S J. Cell Host Microb 2009; 5(1): 95-105). NYVAC-Pf7 directs immune responses to sporozoites, and all other life cycle stages, including induction of antibodies that have been shown to block *Plasmodium* transmission by mosquitoes—NYVAC-Pf7.1 and NYVAC-Pf7.2 are expected to enhance immunogenicity.

The asexual blood stage vaccines attempt to block parasite infection of red blood cells. It is this stage of rapid parasite replication that leads to the onset of clinical symptoms of the disease. Vaccines directed to this stage would only hope to limit or reduce the level of infection and therefore the severity of the symptoms, therefore blood stage vaccines should only be considered as part of a multi-component malaria vaccine. (Thera MAN. Jour. Med. 2011; 365(11): 1004-13). Targeted blood stage antigens that have been evaluated are the apical membrane protein (AMA1), merozoite surface protein (MSP)1, 2 and 3, (SERAS) erythrocyte binding antigen 175(EBA 175), glutamine-rich protein long synthetic peptide (GRURP) and ring-infected erythrocyte surface antigen (RESA). (WHO, "The Rainbow Tables" Initiative for Vaccine Research 2010). The results of 40 phase I/II trials directed to blood-stage candidate vaccines have been very disappointing, showing at best "reduced parasite density". (Goodman, A L. Ann. Trop. Med. Parasitol. 2010; 104(3): 189-211, Genton B. J. Inf. Dis. 2002; 185(6):820-7., Ogutu, B R. Plos ONE 2009; 4(3) e4708, Thera M A. N. Eng. J. Med. 2011; 365(11): 1004-13. Sheehy, S H. Mol. Ther. 2012; 20(12): 2355-68.) Antigenic variation of the blood stage antigens represents one of the biggest hurdles for vaccines directed to these antigens. (Ellis R D. Human Vaccines 2010; 6(8): 627-34). However, naturally acquired immunity (or the bites of one thousand irradiated mosquitoes) induces resistance to *Plasmodium* infection—this encourages development of novel vaccines such as NYVAC-Pf7.1.

A great deal of malaria vaccine research (pre-erythrocytic) has been devoted to studies using rodent malaria species for the development of chimeric rodent/human models with hopes of better assessing a variety of vaccine candidates and vaccine delivery platforms applicable to human *P. falciparum* before entering clinical trials. (Mlambo, G. Eukaryot. Cell 2008;7(11); 1875-1879, Langhorne J. Chem. Immunol. 2002; 80: 204-228) *P. yoelii* and *P. chabaudi* rodent malaria species have been utilized to demonstrate protection against blood stage parasitemia by vaccines expressing MSP1 and AMA1. (Draper S J. Nat. Med. 2008; 14: 819-821, Biswas, S. J. Immunol. 2012; 188(10): 5041-53.) A third rodent model, *P. berghei* has been widely used to study pre-erythrocytic and transmission blocking vaccines. (Kaba S A. J. Immunol. 2009; 183(11): 7268-77, Sridhar, S. J. Virol. 2008; 82(8): 3822-33, Blagborough A M. Vaccine 2009; 27(38): 5187-94) *P. berghei* has proven to be much more difficult to generate protective responses against than either *P. yoelii* or *P. chabaudi*. (Yoshida S. Plos ONE 2010; 5(10) e13727, Weiss R. Vaccine 2010; 28(28): 4515-22) It is this difficulty that makes the *P. berghei* system of great interest as a model, possibly leading to better preclinical analysis for potential pre-erythocytic vaccines for *P. falciparum*. (Goodman, A L. Sci Rep. 2013; 3: 1706.) The complexity of immune responses induced by different poxvirus vaccine vector strains is not fully understood. In the case of immunization with different poxvirus vectors expressing CSP, NYVAC stands out by inducing high levels of protection of mice. A full understanding of poor results from vaccinia virus strains WR and Wyeth expressing CSP has not been achieved. High levels of protection induced by NYVAC-K1L expressing *P. berghei* CSP has furthered the notion that NYVAC based vectors have potential as human malaria vaccine candidates (Lanar D E, Infect Immun. 1996; May; 64(5):1666-71).

Sexual Stage vaccines, or transmission blocking vaccines are vaccines that target the sexual stage of Plasmodia by blocking the fertilization of gametes in the mosquito midgut, thus preventing further development in the vector and subsequent rounds of new infections. Although not fully understood, it is believed that ingested sexual stage antibodies, complement and cytokines inhibit oocyst development in the vector. There are four main sexual stage antigens that have been targeted in early preclinical studies, antigens from the gametocyte P230, P48/45 and antigens from zygote P28 and P25. (Arevalo-Herrera M. Mem. Inst. Oswaldo Cruz. 2011; 106 suppl. 1:202-11). P25 is the only sexual stage antigen to reach later stage vaccine clinical trials. Additional transmission blocking vaccine targets would include antigens of the ookinete. (Dinglasan R R. Trends Parasitol. 2008;24(8) :364-70). Interestingly, it has been shown that antibodies generated against the mosquito mid-gut antigen aminopeptidase-N (AgAPN1) are effective in blocking ookinete invasion. (Dinglasan R R. Proc. Nat. Acd. Sci. 2007; 104(33): 13461-6.)

Great hopes have been placed in the GSK RTS,S malaria vaccine, currently in late phase III trials. Data from the most recent RTS,S trial (2011) have included a target population of children from 5-17 months old. Using a 14-month follow up, the vaccine was found to have an efficacy of 50.4% as scored by the first clinical episode. (N. Eng. Jour. Med 2011 First Results of Phase 3 trial of RTS,S/AS01). Currently an additional large Phase III RTS,S trial is underway looking at establishing efficacy in a target population of children just 6-12 weeks old. However, as the results are encouraging from the RTS,S trials, it is understood that this vaccine will not be fully efficacious. It is already apparent even before licensure, that second generation vaccines are desperately needed to provide greater protection. As discussed above, there is a focused effort and strategic goal put forth by the international organization PATH, and the Malaria Vaccine Initiative (MVI), that by 2020 malaria vaccines provide efficacy approaching 80%. It is clear that non-vaccine approaches and measures such as vector control and drug treatments have failed in controlling malaria and several other infectious diseases (Henderson D A. Vaccine 1999; 17(sup3): 53-55). Many investigators believe a successful malaria vaccine will only be achieved with multistage, multi-component vaccines targeting several stages of this complex parasitic organism. (Richie T L. Nature 2002; (415):694-701., Heppner D G. Vaccine 2005; 23: 2243-50., Malaria Eradication: Vaccines PloS Med. 2011; 8(1): e1000398.) Interestingly, natural protection in endemic areas seems to be achieved by the slow acquisition of immune responses acquired over years of uncomplicated exposure to a variety of diverse malaria antigens. Semi-immune adults remain susceptible to asymptomatic parasitemia, but importantly, are protected against clinical disease. However, this protective immunity is short-lived and lost after only a few years without repeated malaria exposures. (Thera M A. Annu. Rev. Med. 2012; 63: 345-357)

Specific embodiments of the invention include: Coexpression of Flagellin or an operable binding portion thereof and *Plasmodium* antigen(s) or immunogen(s), advantageously by a poxvirus vector, and more advantageously by a poxvirus vector that has reproductive capability via K1L. The invention comprehends poxvirus, e.g., vaccinia, vectors developed to specifically deliver the Flagellin PAMP responsible for activation of TLR5 for enhanced adaptive immune responses to co-expressed Malaria antigen(s). The invention thus comprehends a non-naturally occurring or synthetic or engineered or recombinant poxvirus, e.g., vaccinia vector that contains DNA for and expression of multiple *P. falciparum* antigens for which adaptive immune responses are desired and the entire or a binding portion of the bacterial protein Flagellin, and advantageously the poxvirus vector has reproductive capability via K1L. The binding portion of Flagellin, is the portion responsible for binding to and activating the TLR5 receptor, resulting in a cascade of immune stimulating pro-inflammatory responses to the co-expressed *P. falciparum* antigen(s). The mode in which Flagellin or the operable binding portion thereof is expressed (either as peptide or fusion) with *P. falciparum* antigen(s) provides for a multiplicity of options; the key is that the expressed Flagellin or portion thereof is operable to specifically agonize TLR5 to further stimulate adjuvant adaptive immune responses to co-expressed Malaria antigens. A particularly preferred embodiment is a non-naturally occurring or recombinant or synthetic or engineered poxvirus, e.g., vaccinia, that co-expresses K1L, Flagellin or an operable binding portion thereof and one or more Malaria antigen(s) or immunogen(s). An enhanced NYVAC or MVA or MVA-BN vector (e.g., one that expresses K1L) replicates in human tissues to a level intermediate of that of the more virulent parental replication competent strain Copenhagen and the replication deficient stain NYVAC or MVA or MVA-BN. When such an enhanced vector further co-express at least one *P. falciparum* antigen(s) or immunogen(s) for which adaptive immune responses are desired and the entire or a binding portion of the bacterial protein Flagellin (wherein the binding portion of the Flagellin is the portion responsible for binding to and activating the TLR5 receptor), a cascade of immune stimulating pro-inflammatory responses to the co-expressed *P. falciparum* antigen(s) or immunogen(s) results. The Flagellin sequence and species and mode in which Flagellin is expressed (either as peptide or fusion) is selected to specifically agonize TLR5 to further stimulate adaptive immune responses to *P. falciparum*.

The invention also comprehends *P. falciparum* antigen(s) or immunogen(s) co-expressed with Flagellin or an operable binding portion thereof in vitro. After infecting cells in vitro with an inventive recombinant, the expression products are collected and the collected malarial expression products can then be employed in a vaccine, antigenic or immunological composition which also contains a suitable carrier.

Alternatively, the viral vector system, especially the preferred poxvirus vector system, of the invention can itself be employed in a vaccine, immunological or immunogenic composition which also contains a suitable carrier. The recombinant poxvirus in the composition expresses the malarial products and Flagellin or a binding operable portion thereof in vivo after administration or inoculation. Advantageously, the poxvirus has some reproductive capacity, e.g., from K1L being present in an attenuated (as to mammals) poxvirus such as a NYVAC, ALVAC, TROVAC, MVA, MVA-BN, avipox, canarypox, or fowlpox.

The antigenic, immunological or vaccine composition of the invention either containing products expressed or containing a recombinant poxvirus is administered in the same fashion as typical malarial antigenic immunological or vaccine compositions (e.g., NYVAC-Pf7). One skilled in the medical arts can determine dosage from this disclosure without undue experimentation, taking into consideration such factors as the age, weight, and general health of the particular individual.

Additionally, the inventive recombinant poxvirus and the expression products therefrom stimulate an immune or antibody response in animals. From those antibodies, by techniques well-known in the art, monoclonal antibodies can be prepared and, those monoclonal antibodies, can be employed in well known antibody binding assays, diagnostic kits or tests to determine the presence or absence of particular malarial antigen(s) and therefrom the presence or absence of malaria or, to determine whether an immune response to malaria or malarial antigen(s) has simply been stimulated. Monoclonal antibodies are immunoglobulins produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies can be easily standardized. Methods for producing monoclonal antibodies are well known to those of ordinary skill in the art, e.g., Koprowski, H. et al., U.S. Pat. No. 4,196,265, issued Apr. 1, 1989, incorporated herein by reference. Uses of monoclonal antibodies are known. One such use is in diagnostic methods, e.g., David, G. and Greene, H., U.S. Pat. No. 4,376,110, issued Mar. 8, 1983, incorporated herein by reference. Monoclonal antibodies have also been used to recover materials by immunoadsorption chromatography, e.g. Milstein, C., 1980, Scientific American 243:66, 70, incorporated herein by reference.

The present invention will be further illustrated in the following Examples which are given for illustration purposes only and are not intended to limit the invention in any way.

EXAMPLES

Embodiments of this invention include: NYVAC-PF7.1 (AMA1 repair+FliC) and NYVAC-PF7.2 (AMA1 repair+FliC+K1L).

EXAMPLE 1: The development of the Improved NYVAC vaccine vectors for Malaria NYVAC-PF7.1 (AMA1 repair+FliC) and NYVAC-PF7.2 (AMA1 repair+FliC+K1L) are based on NYVAC-PF7 that is described in U.S. Pat. No. 5,766,597, incorporated herein by reference. Modification to these genetic sequences, description of the donor plasmids and methods used for the construction of recombinant virus, are detailed and set forth as follows.

Donor Plasmid Constructions and Primer Sequences for NYVAC-PF7.1

FliC

Dry pellets of *Salmonella enterica* are readily available and were obtained from the University of New Hampshire (e.g., Robert Mooney). The *S. enterica* coding sequence and flanking sequences were amplified using primers RW3 and RW4 then digested with BamHI and EcoRI generating a 1.5 kb fragment.

```
                                                  (SEQ ID NO: 1)
   RW3: TATTCAAGCTTGAATTCGTGTCGGTGAATCAATCG (SEQ ID NO: 2)
   RW4: AACTCTAGAGGATCCAATAACATCAAGTTGTAATTG
```

The 1.5 kb BamHI-EcoRI fragment containing the FliC coding sequence was inserted into the 2.7 kbp BamHI-EcoRI fragment of plasmid pSV-β3Gal (Promega, Madison, Wis.), yielding plasmid pRW2.

The Pi promoter, previously described in U.S. Pat. No. 5,766,597, incorporated herein by reference, was used to drive the expression of FliC.

The Pi promoter sequence:

```
                                                  (SEQ ID NO: 3)
ACTGTAAAAATAGAAACTATAATCATATAATAGTGTAGGTTGGTAGTAGG

GTACTCGTGATTAATTTTATTGTTAAACTTGTCTTAACTCTTAAGTCTTA

TTAATATG
```

A Pi promoted fragment was synthesized by IDT (Coralville, Iowa). The Pi promoted synthetic fragment contained the 5' and 3'FliC coding sequences. This fragment was inserted between the HindIII-Xba1 of pZErO-2 (Invitrogen, Carlsbad, Calif.) yielding plasmid pRW8.

The sequence of the pRW8 insertion:

(SEQ ID NO: 4)
AGATCTACTGTAAAAATAGAAACTATAATCATATAATAGTGTAGGTTGGT

AGTAGGGTACTCGTGATTAATTTTATTGTTAAACTTGTCTTAACTCTTAA

GTCTTATTAATATGGCACAAGTCATTAATACAAACAGCCTGTCGCTGTTG

ACCCAGAATAACCTGAACAAATCCCAGTCCGCTCTGGGCACCGCTATCGA

GCGTCTGTCTTCCGGTCTGGTACCTCCGTTCTGGCGCAGGCGAACCAGGT

TCCGCAAAACGTCCTCTCTTTACTGCGTTAATTTTTATCTCGAGGCCAAT

TAGGCCTATTATATTTTTTATCTAAAAAACTAAAAATAAACATTGATTAA

ATTTTAATATAATACTTAAAAATGGATGTTGTGTCGTTAGATAAACCGTT

TATGTATTTTGAGGAAATTGATAATGAGTTAGATTACGAACCAGAAAGTG

CAAATGAGGTCGCAAAAAAACTGCCGTATCAAGGACAGTTAAAAGAATTC

AMA1 Repairs

AMA coding sequences from in the original NYVAC-PF7 had several regions that needed to be modified for complete authentic AMA1 expression. Firstly, the constructed repairs removed a 5-amino acid (RRIKS (SEQ ID NO: 5) also called IKSRR (SEQ ID NO: 6), both the same insert with reading from different ends) accidental insertion between amino acids 377 and 378 of AMA1, secondly, it was necessary to modify sequences encoding an early transcription termination signal (T5NT) found between nucleotide positions (1436-1442) in the AMA1 coding sequences and lastly to remove unnecessary DNA sequences 3' of the original NYVAC-Pf7, AMA1 coding sequences. Preliminary experiments repairing IKSRR (SEQ ID NO: 6) demonstrated a change of small Pf7 plaques on CEF cells to an increase of plaque size approaching the size of NYVAC plaques.

pRW55 Construction

Plasmid pRW55, containing AMA1 repairs and Pi promoted FliC, was constructed in the following manner. Full length Pi promoted FliC was constructed by insertion of a 1.3 kb pRW2 BbsI-KpnI fragment, containing the central coding portion of FliC, between the BbsI and KpnI sites of pRW8 followed by PCR with the primers VC106/VC107. The product of PCR from NYVAC with the primers VC68/VC105 was combined with the VC106/107 fragment for PCR with the primers VC98/VC106. Three PCR fragments derived from Pf7 with the primer pairs VC110/VC91, VC103/VC109 and VC108/104 were combined for PCR with the primers VC110/VC104. Fragments derived with the primers VC98/VC106 and VC110/VC104 were combined for PCR with the primers VC97/VC98, followed by digestion with SalI for insertion into the SalI site of pUC19 (Yanisch-Perron, C. Gene 1985; 33(1): 103-19.), yielding plasmid pRW55.

Primer Sequences
VC68:
(SEQ ID NO: 7)
AATAGACCTGCTTCGTTGGCCTC

VC91:
(SEQ ID NO: 8)
AGCACTTTTGATCATACTAGCGTTCTTATTTTTG

VC97:
(SEQ ID NO: 9)
CCTACAGGTCGACCATTACACCAGGAACATACATACC

VC98:
(SEQ ID NO: 10)
CCTACAGGTCGACCATATCCGTTTTTGCCAATATCAC

VC103:
(SEQ ID NO: 11)
GAACGCTAGTATGATCAAAAGTGCTTTTCTTCCCACTGGTGCT

VC104:
(SEQ ID NO: 12)
TAGTCTCCTCGAGCTGACAGATCTATAAAAATTAATAGTATGGTTTTTCC
ATCAG

VC105:
(SEQ ID NO: 13)
GATCTGTCAGCTCGAGGAGACTAGTCGTAGGGCCCGGCCGTGGCAATATT
CTGTA

VC106:
(SEQ ID NO: 14)
GATGGAAAAACCATACTATTAATTTTTATAGATCTACTGTAAAAATAGAA
ACTAT

VC107:
(SEQ ID NO: 15)
ATATTGCCACGGCCGGGCCCTACGACTAGTCTCCTCGAGATAAAAATTAA
CGCAG

VC108:
(SEQ ID NO: 16)
AGCTCCAAGAATATTCATTTCAGATGATAAAGACAGTTTAAAATG

VC109:
(SEQ ID NO: 17)
CATCTGAAATGAATATTCTTGGAGCTATAATTTTTTATTCCCTTCATCA
TC

VC110:
(SEQ ID NO: 18)
TGACTAAATATTTAACATTCCCAAGATGATTC

Sequence of 3.9 kb pRW55 insertion:

(SEQ ID NO: 19)
CATCCACTATATTGTTTTGCACATCTCTACCATTAACTAGAAACAAATCAAAGAAAA

TCAAAAACACAATGACTAAATATTTAACATTCCCAAGATGATTCATTTTATATTGTA

ATTATATATTTTCAATTTTGAGGATCAGCTTACATCATGCAGTGGTTAAACAAAAAC

ATTTTTATTCTCAAATGAGATAAAGTGAAAATATATATCATTATATTACAAAGTACA

ATTATTTAGGTTTAATCATGAGAAAATTATACTGCGTATTATTATTGAGCGCCTTTGA

GTTTACATATATGATAAACTTTGGAAGAGGACAGAATTATTGGGAACATCCATATCA

-continued

```
AAATAGTGATGTGTATCGTCCAATCAACGAACATAGGGAACATCCAAAAGAATACG

AATATCCATTACACCAGGAACATACATACCAACAAGAAGATTCAGGAGAAGACGAA

AATACATTACAACACGCATATCCAATAGACCACGAAGGTGCCGAACCCGCACCACA

AGAACAAAATTTATTTTCAAGCATTGAAATAGTAGAAAGAAGTAATTATATGGTA

ATCCATGGACGGAATATATGGCAAAATATGATATTGAAGAAGTTCATGGTTCAGGT

ATAAGAGTAGATTTAGGAGAAGATGCTGAAGTAGCTGGAACTCAATATAGACTTCC

ATCAGGGAAATGTCCAGTATTTGGTAAAGGTATAATTATTGAGAATTCAAATACTAC

TTTTTTAACACCGGTAGCTACGGGAAATCAATATTTAAAAGATGGAGGTTTTGCTTT

TCCTCCAACAGAACCTCTTATGTCACCAATGACATTAGATGAAATGAGACATTTCTA

TAAAGATAATAAATATGTAAAAAATTTAGATGAATTGACTTTATGTTCAAGACATGC

AGGAAATATGATTCCAGATAATGATAAAAATTCAAATTATAAATATCCAGCTGTTTA

TGATGACAAAGATAAAAAGTGTCATATATTATATATTGCAGCTCAAGAAAATAATG

GTCCTAGATATTGTAATAAAGACGAAAGTAAAAGAAACAGCATGTTTTGTTTTAGAC

CAGCAAAAGATATATCATTTCAAAACTATACATATTTAAGTAAGAATGTAGTTGATA

ACTGGGAAAAAGTTTGCCCTAGAAAGAATTTACAGAATGCAAAATTCGGATTATGG

GTCGATGGAAATTGTGAAGATATACCACATGTAAATGAATTTCCAGCAATTGATCTT

TTTGAATGTAATAAATTAGTTTTTGAATTGAGTGCTTCGGATCAACCTAAACAATAT

GAACAACATTTAACAGATTATGAAAAAATTAAAGAAGGTTTCAAAAATAAGAACGC

TAGTATGATCAAAAGTGCTTTTCTTCCCACTGGTGCTTTTAAAGCAGATAGATATAA

AAGTCATGGTAAGGGTTATAATTGGGGAAATTATAACACAGAAACACAAAAATGTG

AAATTTTTAATGTCAAACCAACATGTTTAATTAACAATTCATCATACATTGCTACTAC

TGCTTTGTCCCATCCCATCGAAGTTGAAAACAATTTTCCATGTTCATTATATAAAGAT

GAAATAATGAAAGAAATCGAAAGAGAATCAAAACGAATTAAATTAAATGATAATG

ATGATGAAGGGAATAAAAAAATTATAGCTCCAAGAATATTCATTTCAGATGATAAA

GACAGTTTAAAATGCCCATGTGACCCTGAAATGGTAAGTAATAGTACATGTCGTTTC

TTTGTATGTAAATGTGTAGAAAGAAGGGCAGAAGTAACATCAAATAATGAAGTTGT

AGTTAAAGAAGAATATAAAGATGAATATGCAGATATTCCTGAACATAAACCAACTT

ATGATAAAATGAAAATTATAATTGCATCATCAGCTGCTGTCGCTGTATTAGCAACTA

TTTTAATGGTTTATCTTTATAAAAGAAAAGGAAATGCTGAAAAATATGATAAAATGG

ATGAACCACAAGATTATGGGAAATCAAATTCAAGAAATGATGAAATGTTAGATCCT

GAGGCATCTTTTTGGGGGGAAGAAAAAAGAGCATCACATACAACACCAGTTCTGAT

GGAAAAACCATACTATTAATTTTTATAGATCTACTGTAAAAATAGAAACTATAATCA

TATAATAGTGTAGGTTGGTAGTAGGGTACTCGTGATTAATTTTATTGTTAAACTTGTC

TTAACTCTTAAGTCTTATTAATATGGCACAAGTCATTAATACAAACAGCCTGTCGCT

GTTGACCCAGAATAACCTGAACAAATCCCAGTCCGCTCTGGGCACCGCTATCGAGC

GTCTGTCTTCCGGTCTGCGTATCAACAGCGCGAAAGACGATGCGGCAGGTCAGGCG

ATTGCTAACCGTTTTACCGCGAACATCAAAGGTCTGACTCAGGCTTCCCGTAACGCT

AACGACGGTATCTCCATTGCGCAGACCACTGAAGGCGCGCTGAACGAAATCAACAA

CAACCTGCAGCGTGTGCGTGAACTGGCGGTTCAGTCTGCTAACAGCACCAACTCCCA

GTCTGACCTCGACTCCATCCAGGCTGAAATCACCCAGCGCCTGAACGAAATCGACC
```

-continued
```
GTGTATCCGGCCAGACTCAGTTCAACGGCGTGAAAGTCCTGGCGCAGGACAACACC

CTGACCATCCAGGTTGGTGCCAACGACGGTGAAACTATCGATATCGATCTGAAGCA

GATCAACTCTCAGACCCTGGGTCTGGATACGCTGAATGTGCAACAAAAATATAAGG

TCAGCGATACGGCTGCAACTGTTACAGGATATGCCGATACTACGATTGCTTTAGACA

ATAGTACTTTTAAAGCCTCGGCTACTGGTCTTGGTGGTACTGACCAGAAAATTGATG

GCGATTTAAAATTTGATGATACGACTGGAAAATATTACGCCAAAGTTACCGTTACGG

GGGGAACTGGTAAAGATGGCTATTATGAAGTTTCCGTTGATAAGACGAACGGTGAG

GTGACTCTTGCTGGCGGTGCGACTTCCCCGCTTACAGGTGGACTACCTGCGACAGCA

ACTGAGGATGTGAAAAATGTACAAGTTGCAAATGCTGATTTGACAGAGGCTAAAGC

CGCATTGACAGCAGCAGGTGTTACCGGCACAGCATCTGTTGTTAAGATGTCTTATAC

TGATAATAACGGTAAAACTATTGATGGTGGTTTAGCAGTTAAGGTAGGCGATGATTA

CTATTCTGCAACTCAAAATAAAGATGGTTCCATAAGTATTAATACTACGAAATACAC

TGCAGATGACGGTACATCCAAAACTGCACTAAACAAACTGGGTGGCGCAGACGGCA

AAACCGAAGTTGTTTCTATTGGTGGTAAAACTTACGCTGCAAGTAAAGCCGAAGGTC

ACAACTTTAAAGCACAGCCTGATCTGGCGGAAGCGGCTGCTACAACCACCGAAAAC

CCGCTGCAGAAAATTGATGCTGCTTTGGCACAGGTTGACACGTTACGTTCTGACCTG

GGTGCGGTACAGAACCGTTTCAACTCCGCTATTACCAACCTGGGCAACACCGTAAAC

AACCTGACTTCTGCCCGTAGCCGTATCGAAGATTCCGACTACGCGACCGAAGTTTCC

AACATGTCTCGCGCGCAGATTCTGCAGCAGGCCGGTACCTCCGTTCTGGCGCAGGCG

AACCAGGTTCCGCAAAACGTCCTCTCTTTACTGCGTTAATTTTTATCTCGAGGAGACT

AGTCGTAGGGCCCGGCCGTGGCAATATTCTGTATTACGTATTATATATGTAATAAAC

GTTCACGTAAATACAAAACAGAGAACAAAGTCTAGATTTTTGACTTACATAAATGTC

TGGGATAGTAAAATCTATCATATTGAGCGGACCATCTGGTTCAGGAAAGACAGCCA

TAGCCAAAAGACTATGGGAATATATTTGGATTTGTGGTGTCCCATACCACTAGATTT

CCTCGTCCTATGGAACGAGAAGGTGTCGATTACCATTACGTTAACAGAGAGGCCATC

TGGAAGGGAATAGCCGCCGGAAACTTTCTAGAACATACTGAGTTTTTAGGAAATATT

TACGGAACTTCTAAAACTGCTGTGAATACAGCGGCTATTAATAATCGTATTTGTGTG

ATGGATTTAAACATCGACGGTGTTAGAAGTTTTAAAAATACTTACCTAATGCCTTAC

TCGGTGTATATAAGACCTACCTCTCTTAAAATGGTTGAGACCAAGCTTCGTTGTAGA

AACACTGAAGCTAACGATGAGATTCATCGTCGCGTGATATTGGCAAAAACGGATAT

GGATGAGGCCAACGAAGCAGGTCTATTCGACACTATTATTATTGAAGATGATGTGA

ATTTAGCATATAGTAAGTTAATTCAGATACTACAGGACCGTATTAGAATGTATTTTA

ACACTAATTAAAGACTTAAGACTTAAAACTTGATAATTAATAATATAACTCGTTTTT

ATATGTGGCTATTTCAACGTCTAATGTATTAGTTAAATATTAAAACTTACCACGTAA

AACTTAAAATTTAAAATGATATTTCATTGACAGATAGATCACACATTATGAACTTTC

AAGGACTTGTGTTAACTGACAATTGCAAAAATCAATGGGTCGTTGGACCATTAATAG

GAAAAGG
```

FIG. 1 illustrates primer locations.

Additional Donor Plasmid Construction and Primer Sequences Specific for NYVAC-PF7.2 (AMA1 repair+ FliC+K1L)

The vaccinia virus Copenhagen strain K1L promoted K1L coding sequence (Gillard et al., 1986) was synthesized at TOP Gene Technologies (Montreal, Canada) as a fragment similar to the BgIII (partial)-HpaI fragment described in Perkus et al., 1989; XhoI was added to the 5' end and SpeI was added 3' of HpaI. The synthetic DNA was inserted between the AscI and PacI sites of an intermediate cloning shuttle pAPG10, yielding plasmid pK1L.

Figure 2A:
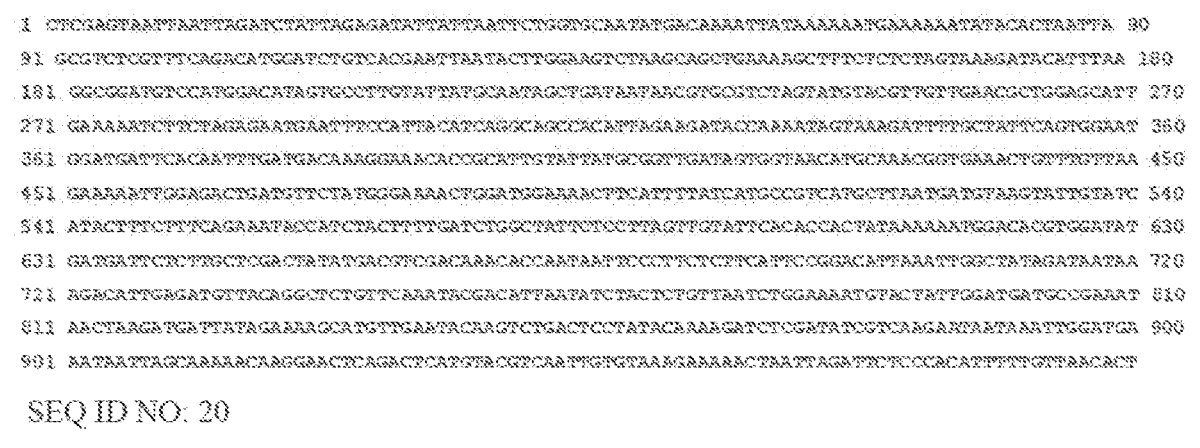
Figure 2B:
FIG. 2B is a diagram of the K1L expression cassette for insertion between the XhoI and SpeI sites in FIG. 1 for generation of Pf7.2
Figure 3A:
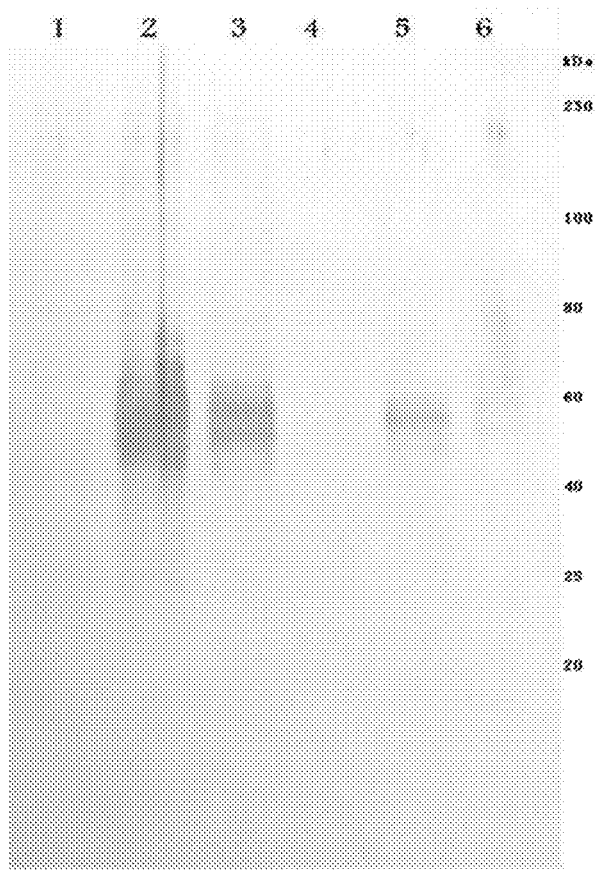
FIGS. 3A, 3B, 3C, 3D contain the results of expression by inventive recombinants.
Figure 3B:
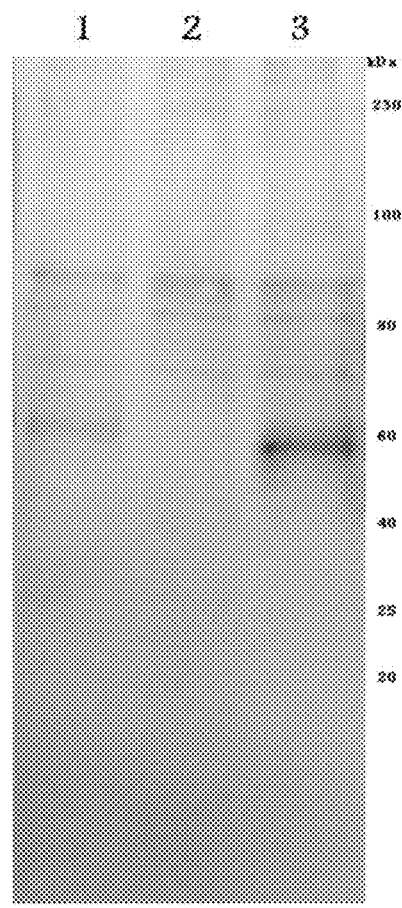
Figure 3C:
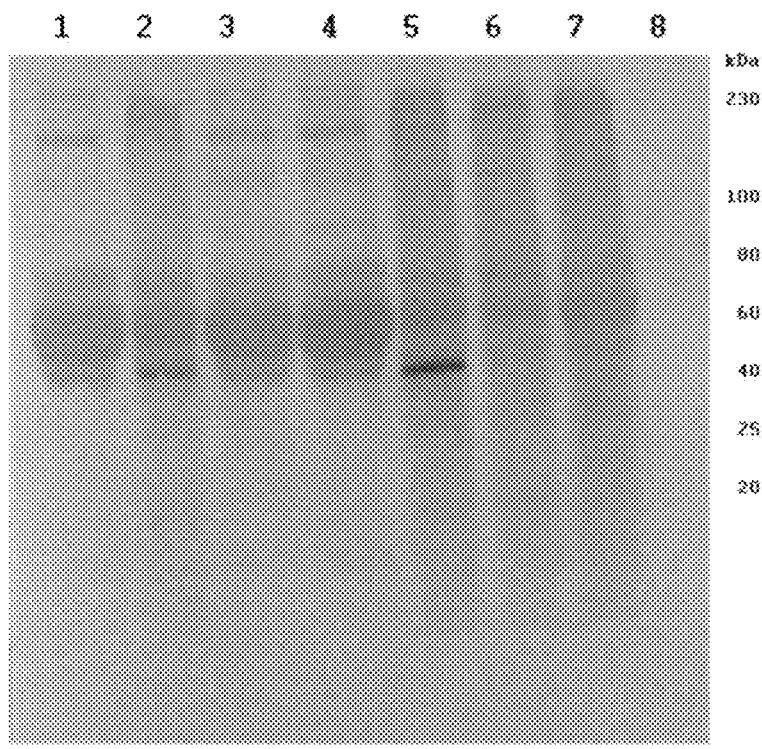
Figure 3D:
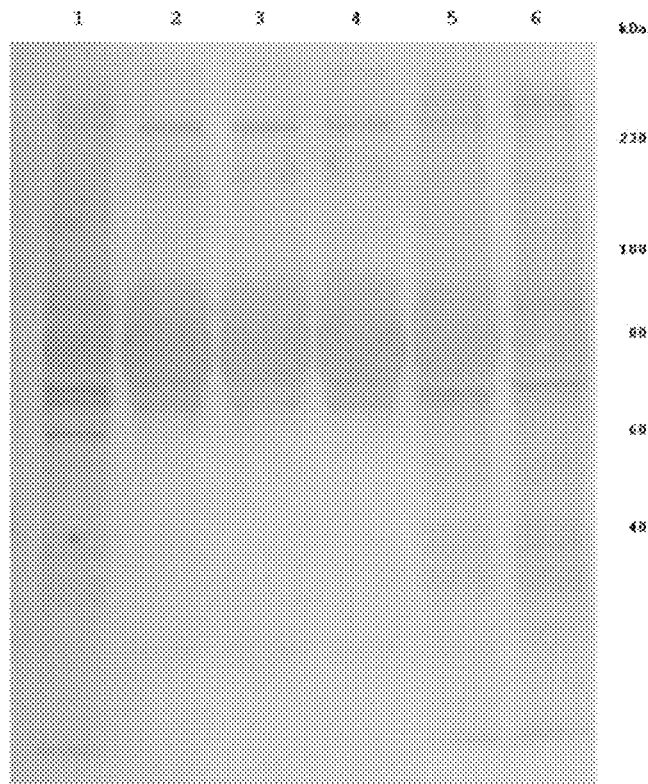

Plasmid pRW56 was constructed by insertion of the 1Kb XhoI-SpeI fragment from pK1L, containing the K1L expression cassette, between the XhoI and SpeI sites of pRW55. The synthetic DNA sequence and its position are illustrated in FIGS. 2A, 2B.

Generation of Recombinant Virus

In vivo recombination (IVR) was performed by transfection of donor plasmid (8 ug) with Lipofectamine 2000 as per manufacturer specification (Invitrogen, Carlsbad, Calif.) into 1E6 poxvirus infected Vero cells using a multiplicity of infection (MOI) of 0.1. Donor plasmid pRW55 was used in an IVR with NYVAC-PF7 to generate the recombinant NYVAC-PF7.1 containing AMA1 repairs plus FliC. Donor plasmid pRW56 was used in an IVR with NYVAC-PF7.1 to generate NYVAC-PF7.2 containing AMA1 repairs, FliC plus K1L.

Recombinants were identified by polymerase chain reaction (PCR). Briefly, one PCR primer was located within newly inserted sequences not present in NYVAC-Pf7. The second primer, directed toward the first, was located in sequences outside of the donor plasmid. Location of the primer outside of the donor plasmid ensured no amplification of the donor plasmid.

After the IVR, virus was serially diluted in 96 well plates. Between 1-10% of each single well was used in PCR analysis. Wells identified as positive by PCR were repeatedly serially diluted for several rounds of infection and further tested by PCR.

After several rounds of PCR analysis, a second set of PCR primers were used to assess purity. The second primer set contained sequences present in the original NYVAC-Pf7 that flanked the insertion site; input NYVAC-Pf7 control virus would yield a PCR fragment smaller than a NYVAC-Pf7.1 recombinant containing an insertion. Following detection of a high level of purity by PCR using the 96 well format, virus was further purified by plaquing under agarose (Perkus M. et al., 1993). Well isolated plaques were picked from agarose, amplified and screened by PCR with both sets of PCR primers. Purification sometimes requires more than one round of plaque purification under agarose.

Once a pure recombinant was identified, the virus stock was amplified. All insertions were assessed for correct size by PCR fragment analysis on agarose gels, and finally nucleotide sequence of all insertions and flanking sequences were confirmed. Expression analysis was confirmed by Western blotting. FIGS. 3A, 3B, 3C, 3D demonstrate expression by inventive recombinants. Compared with NYVAC-Pf7, construction of NYVAC-Pf7.1 did not involve modifications of Pfs25 or CSP; it is important to note increased expression levels demonstrated in the FIGS. that may be due to FliC survival signals expressed by the novel vaccine candidate NYVAC-Pf7.1 or by removal of potentially deleterious effects of RRIKS (SEQ ID NO: 5) from AMA 1.

FIG. 3A shows expression of *P. falciparum* CSP from cell lysates two days post infection: Lysates were separated by 10% SDS-PAGE for western blotting with colorimetric detection. Rabbit antibody (Alpha Diagnostics, San Antonio, Tex.) directed to *P. falciparum* CSP repeat sequence $(NANP)_5$. Lanes: 1 & 4, NYVAC; 2 & 5, NYVAC Pf7.1; 3 & 6, NYVAC Pf7. Compared with lanes 1-3, 20% of lysates were loaded on lanes 4-6.

FIG. 3B shows expression of secreted *P. falciparum* CSP from infected cell media two days post infection: Cell media was separated by 10% SDS-PAGE for western blotting with colorimetric detection. Rabbit antibody (Alpha Diagnostics, San Antonio, Tex.) directed to *P. falciparum* CSP repeat sequence (NANP)5. Lanes: 1, NYVAC Pf7; 2, NYVAC; 3, NYVAC Pf7.1.

FIG. 3C shows expression of *P. falciparum* Pfs25 two days post infection: Lysates were separated by 10% SDS-PAGE for western blotting and colorimetric detection: Rabbit anti-Pfs25 antiserum (ATCC, Manassas, Va.). Lanes: 1, NYVAC Pf7 supernatant; 2, NYVAC Pf7 cell pellet; 3, NYVAC supernatant; 4, NYVAC Pf7.1 supernatant; 5, NYVAC Pf7.1 cell pellet; 6, NYVAC cell pellet; 7, uninfected cell pellet; 8, molecular weight marker.

FIG. 3D shows FliC expression two days post infection: 10% SDS-PAGE analyzed by western blotting and colorimetric detection. Mouse anti-FliC (BioLegend, San Diego, Calif.). Lane 1, NYVAC Pf7.1 cells; 2, NYVAC Pf7.1 supernatant; 3, NYVAC supernatant; 4, NYVAC Pf7 supernatant; 5 NYVAC Pf7 cells; 6 NYVAC cells.

REFERENCES

1. Abe T, Kaname Y, Hamamoto I, Tsuda Y, Wen X, Taguwa S, Moriishi K, Takeuchi O, Kawai T, Kanto T, Hayashi N, Akira S, Matsuura Y. Hepatitis C virus nonstructural protein 5A modulates the toll-like receptor-MyD88-dependent signaling pathway in macrophage cell lines. J Virol. 2007 September; 81(17):8953-66. Epub 2007 Jun. 13. PubMed PMID: 17567694; PubMed Central PMCID: PMC 1951400.

2. Adams S. Toll-like receptor agonists in cancer therapy. Immunotherapy. 2009 November; 1(6):949-64. doi: 10.2217/imt.09.70. Review. PubMed PMID: 20563267; PubMed Central PMCID: PMC2886992.

3. Agnandji S T, Lell B, Soulanoudjingar S S, Fernandes J F, Abossolo B P, Conzelmann C, Methogo B G, Doucka Y, Flamen A, Mordmüller B, Issifou S, Kremsner P G, Sacarlal J, Aide P, Lanaspa M, Aponte J J, Nhamuave A, Quelhas D, Bassat Q, Mandjate S, Macete E, Alonso P, Abdulla S, Salim N, Juma O, Shomari M, Shubis K, Machera F, Hamad A S, Minja R, Mtoro A, Sykes A, Ahmed S, Urassa A M, Ali A M, Mwangoka G, Tanner M, Tinto H, D'Alessandro U, Sorgho H, Valea I, Tahita M C, Kaboré W, Ouédraogo S, Sandrine Y, Guiguemdé R T, Ouédraogo J B, Hamel M J, Kariuki S, Odero C, Oneko M, Otieno K, Awino N, Omoto J, Williamson J, Muturi-Kioi V, Laserson K F, Slutsker L, Otieno W, Otieno L, Nekoye O, Gondi S, Otieno A, Ogutu B, Wasuna R, Owira V, Jones D, Onyango A A, Njuguna P, Chilengi R, Akoo P, Kerubo C, Gitaka J, Maingi C, Lang T, Olotu A, Tsofa B, Bejon P, Peshu N, Marsh K, Owusu-Agyei S, Asante K P, Osei-Kwakye K, Boahen O, Ayamba S, Kayan K, Owusu-Ofori R, Dosoo D, Asante I, Adjei G, Adjei G, Chandramohan D, Greenwood B, Lusingu J, Gesase S, Malabeja A, Abdul O, Kilavo H, Mahende C, Liheluka E, Lemnge M, Theander T, Drakeley C, Ansong D, Agbenyega T, Adjei S, Boateng H O, Rettig T, Bawa J, Sylverken J, Sambian D, Agyekum A, Owusu L, Martinson F, Hoffman I, Mvalo T, Kamthunzi P, Nkomo R, Msika A, Jumbe A, Chome N, Nyakuipa D, Chintedza J, Ballou W R, Bruls M, Cohen J, Guerra Y, Jongert E, Lapierre D, Leach A, Lievens M, Ofori-Anyinam O, Vekemans J, Carter T, Leboulleux D, Loucq C, Radford A, Savarese B, Schellenberg D, Sillman M, Vansadia P; RTS,S Clinical Trials Partnership. First results of phase 3 trial of RTS,S/AS01 malaria vaccine in African children. N Engl J Med. 2011 November 17; 365(20): 1863-75. doi: 10.1056/NEJMoa1102287. Epub 2011 Oct. 18. PubMed PMID: 22007715.

4. Aide P, Bassat Q, Alonso P L. Towards an effective malaria vaccine. Arch Dis Child. 2007 June; 92(6):476-9. Review. PubMed PMID: 17515617; PubMed Central PMCID: PMC2066178.

5. Akira S. Innate immunity and adjuvants. Philos Trans R Soc Lond B Biol Sci. 2011 Oct. 12; 366(1579):2748-55. doi: 10.1098/rstb.2011.0106. Review. PubMed PMID: 21893536; PubMed Central PMCID: PMC3146784.

6. Akira S, Uematsu S, Takeuchi O. Pathogen recognition and innate immunity. Cell. 2006 Feb. 24; 124(4):783-801. Review. PubMed PMID: 16497588.

7. Akira S, Takeda K. Toll-like receptor signalling. Nat Rev Immunol. 2004 July; 4(7):499-511. Review. PubMed PMID: 15229469.

8. Akira S, Takeda K, Kaisho T. Toll-like receptors: critical proteins linking innate and acquired immunity. Nat Immunol. 2001 August; 2(8):675-80. Review. PubMed PMID: 11477402.

9. Alexopoulou L, Holt A C, Medzhitov R, Flavell R A. Recognition of double-stranded RNA and activation of NF-kappaB by Toll-like receptor 3. Nature. 2001 October 18; 413(6857):732-8. PubMed PMID: 11607032.

10. Alonso P L, Sacarlal J, Aponte J J, Leach A, Macete E, Aide P, Sigauque B, Milman J, Mandomando I, Bassat Q, Guinovart C, Espasa M, Corachan S, Lievens M, Navia M M, Dubois M C, Menendez C, Dubovsky F, Cohen J, Thompson R, Ballou W R. Duration of protection with RTS,S/AS02A malaria vaccine in prevention of *Plasmodium falciparum* disease in Mozambican children: single-blind extended follow-up of a randomised controlled trial. Lancet. 2005 December 10; 366(9502):2012-8. PubMed PMID: 16338450.

11. Alonso P L, Sacarlal J, Aponte J J, Leach A, Macete E, Milman J, Mandomando I, Spiessens B, Guinovart C, Espasa M, Bassat Q, Aide P, Ofori-Anyinam O, Navia M M, Corachan S, Ceuppens M, Dubois M C, Demoitié M A, Dubovsky F, Menéndez C, Tornieporth N, Ballou W R, Thompson R, Cohen J. Efficacy of the RTS,S/AS02A vaccine against *Plasmodium falciparum* infection and disease in young African children: randomised controlled trial. Lancet. 2004 Oct. 16-22; 364(9443): 1411-20. PubMed PMID: 15488216.

12. Amara R R, Villinger F, Altman J D, Lydy S L, O'Neil S P, Staprans S I, Montefiori D C, Xu Y, Herndon J G, Wyatt L S, Candido M A, Kozyr N L, Earl P L, Smith J M, Ma H L, Grimm B D, Hulsey M L, Miller J, McClure H M, McNicholl J M, Moss B, Robinson H L. Control of a mucosal challenge and prevention of AIDS by a multiprotein DNA/MVA vaccine. Science. 2001 Apr. 6; 292(5514):69-74. PubMed PMID: 11393868.

13. Amato R J, Shingler W, Naylor S, Jac J, Willis J, Saxena S, Hernandez-McClain J, Harrop R. Vaccination of renal cell cancer patients with modified vaccinia ankara delivering tumor antigen 5T4 (TroVax) administered with interleukin 2: a phase II trial. Clin Cancer Res. 2008 Nov. 15; 14(22):7504-10. doi: 10.1158/1078-0432.CCR-08-0668. PubMed PMID: 19010868.

14. Andersen-Nissen E, Smith K D, Strobe K L, Barrett S L, Cookson B T, Logan S M, Aderem A. Evasion of Toll-like receptor 5 by flagellated bacteria. Proc Natl Acad Sci USA. 2005 Jun. 28; 102(26):9247-52. Epub 2005 Jun. 13. PubMed PMID: 15956202; PubMed Central PMCID: PMC 1166605.

15. Antoine G, Scheiflinger F, Dorner F, Falkner F G. The complete genomic sequence of the modified vaccinia Ankara strain: comparison with other orthopoxviruses. Virology. 1998 May 10; 244(2):365-96. Review. Erratum in: Virology. 2006 Jul. 5; 350(2):501-2. PubMed PMID: 9601507.

16. Antonis A F, van der Most R G, Suezer Y, Stockhofe-Zurwieden N, Daus F, Sutter G, Schrijver R S. Vaccination with recombinant modified vaccinia virus Ankara expressing bovine respiratory syncytial virus (bRSV) proteins protects calves against RSV challenge. Vaccine. 2007 Jun. 15; 25(25):4818-27. Epub 2007 Apr. 20. PubMed PMID: 17499893.

17. Aponte J J, Schellenberg D, Egan A, Breckenridge A, Carneiro I, Critchley J, Danquah I, Dodoo A, Kobbe R, Lell B, May J, Premji Z, Sanz S, Sevene E, Soulaymani-Becheikh R, Winstanley P, Adjei S, Anemana S, Chandramohan D, Issifou S, Mockenhaupt F, Owusu-Agyei S, Greenwood B, Grobusch M P, Kremsner P G, Macete E, Mshinda H, Newman R D, Slutsker L, Tanner M, Alonso P, Menendez C. Efficacy and safety of intermittent preventive treatment with sulfadoxine-pyrimethamine for malaria in African infants: a pooled analysis of six randomised, placebo-controlled trials. Lancet. 2009 Oct. 31; 374(9700): 1533-42. doi: 10.1016/S0140-6736(09)61258-7. Epub 2009 Sep. 16. Review. PubMed PMID: 19765816.

18. Arlen P M, Skarupa L, Pazdur M, Seetharam M, Tsang K Y, Grosenbach D W, Feldman J, Poole D J, Litzinger M, Steinberg S M, Jones E, Chen C, Marte J, Parnes H, Wright J, Dahut W, Schlom J, Gulley J L. Clinical safety of a viral vector based prostate cancer vaccine strategy. J Urol. 2007 October; 178(4 Pt 1): 1515-20. Epub 2007 Aug. 16. PubMed PMID: 17707059.

19. Arlen P M, Gulley J L, Todd N, Lieberman R, Steinberg S M, Morin S, Bastian A, Marte J, Tsang K Y, Beetham P, Grosenbach D W, Schlom J, Dahut W. Antiandrogen, vaccine and combination therapy in patients with nonmetastatic hormone refractory prostate cancer. J Urol. 2005 August; 174(2):539-46. PubMed PMID: 16006888.

20. Arévalo-Herrera M, Solarte Y, Marin C, Santos M, Castellanos J, Beier J C, Valencia S H. Malaria transmission blocking immunity and sexual stage vaccines for interrupting malaria transmission in Latin America. Mem Inst Oswaldo Cruz. 2011 August; 106 Suppl 1:202-11. Review. PubMed PMID: 21881775.

21. Backes S, Sperling K M, Zwilling J, Gasteiger G, Ludwig H, Kremmer E, Schwantes A, Staib C, Sutter G. Viral host-range factor C7 or K1 is essential for modified vaccinia virus Ankara late gene expression in human and murine cells, irrespective of their capacity to inhibit protein kinase R-mediated phosphorylation of eukaryotic translation initiation factor 2alpha. J Gen Virol. 2010 February; 91(Pt 2):470-82. doi: 10.1099/vir.0.015347-0. Epub 2009 Oct. 21. PubMed PMID: 19846675.

22. Bauernfeind F, Hornung V. TLR2 joins the interferon gang. Nat Immunol. 2009 November; 10(11):1139-41. doi: 10.1038/ni 1109-1139. PubMed PMID: 19841644.

23. Bejon P, Lusingu J, Olotu A, Leach A, Lievens M, Vekemans J, Mshamu S, Lang T, Gould J, Dubois M C, Demoitie M A, Stallaert J F, Vansadia P, Carter T, Njuguna P, Awuondo K O, Malabeja A, Abdul O, Gesase S, Mturi N, Drakeley C J, Savarese B, Villafana T, Ballou W R, Cohen J, Riley E M, Lemnge M M, Marsh K, von Seidlein L. Efficacy of RTS,S/AS01E vaccine against malaria in children 5 to 17 months of age. N Engl J Med. 2008 Dec. 11; 359(24):2521-32. doi: 10.1056/NEJMoa0807381. Epub 2008 Dec. 8. PubMed PMID: 19064627; PubMed Central PMCID: PMC2655100.

24. Belyakov I M, Ahlers J D. What role does the route of immunization play in the generation of protective immunity against mucosal pathogens? J Immunol. 2009 Dec. 1; 183 (11):6883-92. doi: 10.4049/jimmunol.0901466. Review. PubMed PMID: 19923474.

25. Belyakov I M, Ahlers J D, Brandwein B Y, Earl P, Kelsall B L, Moss B, Strober W, Berzofsky J A. The importance of local mucosal HIV-specific CD8(+) cytotoxic T lymphocytes for resistance to mucosal viral transmission in mice and enhancement of resistance by local administration of IL-12. J Clin Invest. 1998 Dec. 15; 102(12):2072-81. PubMed PMID: 9854042; PubMed Central PMCID: PMC509161.

26. Ben-Yedidia T, Arnon R. Effect of pre-existing carrier immunity on the efficacy of synthetic influenza vaccine. Immunol Lett. 1998 November; 64(1):9-15. PubMed PMID: 9865596.

27. Benson J, Chougnet C, Robert-Guroff M, Montefiori D, Markham P, Shearer G, Gallo R C, Cranage M, Paoletti E, Limbach K, Venzon D, Tartaglia J, Franchini G. Recombinant vaccine-induced protection against the highly pathogenic simian immunodeficiency virus SIV(mac251): dependence on route of challenge exposure. J Virol. 1998 May; 72(5):4170-82. PubMed PMID: 9557706; PubMed Central PMCID: PMC 109646.

28. Bernasconi N L, Onai N, Lanzavecchia A. A role for Toll-like receptors in acquired immunity: up-regulation of TLR9 by BCR triggering in naive B cells and constitutive expression in memory B cells. Blood. 2003 Jun. 1; 101 (11):4500-4. Epub 2003 Jan. 30. PubMed PMID: 12560217.

29. Beutler B. Inferences, questions and possibilities in Toll-like receptor signalling. Nature. 2004 Jul. 8; 430(6996): 257-63. Review. PubMed PMID: 15241424.

30. Birrell M A, Eltom S. The role of the NLRP3 inflammasome in the pathogenesis of airway disease. Pharmacol Ther. 2011 June; 130(3):364-70. doi: 10.1016/j.pharmthera.2011.03.007. Epub 2011 Mar. 21. Review. PubMed PMID: 21421008.

31. Bisht H, Roberts A, Vogel L, Bukreyev A, Collins P L, Murphy B R, Subbarao K, Moss B. Severe acute respiratory syndrome coronavirus spike protein expressed by attenuated vaccinia virus protectively immunizes mice. Proc Natl Acad Sci USA. 2004 Apr. 27; 101(17):6641-6. Epub 2004 Apr. 19. PubMed PMID: 15096611; PubMedCentral PMCID: PMC404098.

32. Biswas S, Spencer A J, Forbes E K, Gilbert S C, Holder A A, Hill A V, Draper S J. Recombinant viral-vectored vaccines expressing *Plasmodium* chabaudi AS apical membrane antigen 1: mechanisms of vaccine-induced blood-stage protection. J Immunol. 2012 May 15; 188(10): 5041-53. doi: 10.4049/jimmunol. 1101106. Epub 2012 Apr. 13. PubMed PMID: 22504652; PubMed Central PMCID: PMC3378655.

33. Blagborough A M, Sinden R E. *Plasmodium berghei* HAP2 induces strong malaria transmission-blocking immunity in vivo and in vitro. Vaccine. 2009 Aug. 20; 27(38): 5187-94. doi: 10.1016/j.vaccine.2009.06.069. Epub 2009 Jul. 9. Review. PubMed PMID: 19596419.

34. Blanchard T J, Alcami A, Andrea P, Smith G L. Modified vaccinia virus Ankara undergoes limited replication in human cells and lacks several immunomodulatory proteins: implications for use as a human vaccine. J Gen Virol. 1998 May; 79 (Pt 5): 1159-67. PubMed PMID: 9603331.

35. Bojang K A, Olodude F, Pinder M, Ofori-Anyinam O, Vigneron L, Fitzpatrick S, Njie F, Kassanga A, Leach A, Milman J, Rabinovich R, McAdam K P, Kester K E, Heppner D G, Cohen J D, Tornieporth N, Milligan P J. Safety and immunogenicty of RTS,S/AS02A candidate malaria vaccine in Gambian children. Vaccine. 2005 Jul. 14; 23(32):4148-57. Epub 2005 Apr. 15. PubMed PMID: 15964483.

36. Bradley R R, Terajima M. Vaccinia virus K1L protein mediates host-range function in RK-13 cells via ankyrin repeat and may interact with a cellular GTPase-activating protein. Virus Res. 2005 December; 114(1-2):104-12. Epub 2005 Jul. 20. PubMed PMID: 16039000.

37. Bratke K A, McLysaght A, Rothenburg S. A survey of host range genes in poxvirus genomes. Infect Genet Evol. 2013 March; 14:406-25. doi: 10.1016/j.meegid. 2012.12.002. Epub 2012 Dec. 23. PubMed PMID: 23268114.

38. Bray M. Pathogenesis and potential antiviral therapy of complications of smallpox vaccination. Antiviral Res. 2003 April; 58(2):101-14. Review. PubMed PMID: 12742570.

39. Brochier B, Kieny M P, Costy F, Coppens P, Bauduin B, Lecocq J P, Languet B, Chappuis G, Desmettre P, Afiademanyo K, et al. Large-scale eradication of rabies using recombinant vaccinia-rabies vaccine. Nature. 1991 Dec. 19-26; 354(6354):520-2. PubMed PMID: 1758494.

40. Brown S A, Surman S L, Sealy R, Jones B G, Slobod K S, Branum K, Lockey T D, Howlett N, Freiden P, Flynn P, Hurwitz J L. Heterologous Prime-Boost HIV-1 Vaccination Regimens in Pre-Clinical and Clinical Trials. Viruses. 2010 Feb. 1; 2(2):435-467. PubMed PMID: 20407589; PubMed Central PMCID: PMC2855973.

41. Bråve A, Boberg A, Gudmundsdotter L, Rollman E, Hallermalm K, Ljungberg K, Blomberg P, Stout R, Paulie S, Sandström E, Biberfeld G, Earl P, Moss B, Cox J H, Wahren B. A new multi-clade DNA prime/recombinant MVA boost vaccine induces broad and high levels of HIV-1-specific CD8(+) T-cell and humoral responses in mice. Mol Ther. 2007 September; 15(9): 1724-33. Epub 2007 Jun. 19. PubMed PMID: 17579577.

42. Buller R M, Chakrabarti S, Cooper J A, Twardzik D R, Moss B. Deletion of the vaccinia virus growth factor gene reduces virus virulence. J Virol. 1988 March; 62(3):866-74. PubMed PMID: 3339716; PubMed Central PMCID: PMC253644.

43. Buller R M, Smith G L, Cremer K, Notkins A L, Moss B. Decreased virulence of recombinant vaccinia virus expression vectors is associated with a thymidine kinase-negative phenotype. Nature. 1985 Oct. 31-November 6; 317(6040):813-5. PubMed PMID: 4058585.

44. Carrington M, O'Brien S J. The influence of HLA genotype on AIDS. Annu Rev Med. 2003;54:535-51. Epub 2001 Dec. 3. Review. PubMed PMID: 12525683.

45. Carty M, Bowie A G. Recent insights into the role of Toll-like receptors in viral infection. Clin Exp Immunol. 2010 September; 161(3):397-406. doi: 10.1111/j. 1365-2249.2010.04196.x. Review. PubMed PMID: 20560984; PubMed Central PMCID: PMC2962956.

46. Casey C G, Iskander J K, Roper M H, Mast E E, Wen X J, Török T J, Chapman L E, Swerdlow D L, Morgan J, Heffelfinger J D, Vitek C, Reef S E, Hasbrouck L M, Damon I, Neff L, Vellozzi C, McCauley M, Strikas R A, Mootrey G. Adverse events associated with smallpox vaccination in the United States, January-October 2003. JAMA. 2005 Dec. 7; 294(21):2734-43. PubMed PMID: 16333009.

47. Chen Z, Zhang L, Qin C, Ba L, Yi C E, Zhang F, Wei Q, He T, Yu W, Yu J, Gao H, Tu X, Gettie A, Farzan M, Yuen K Y, Ho D D. Recombinant modified vaccinia virus Ankara expressing the spike glycoprotein of severe acute respiratory syndrome coronavirus induces protective neutralizing antibodies primarily targeting the receptor binding region. J Virol. 2005 March; 79(5):2678-88. PubMed PMID: 15708987; PubMed Central PMCID: PMC548443.

48. Child S J, Palumbo G J, Buller R M, Hruby D E. Insertional inactivation of the large subunit of ribonucleotide reductase encoded by vaccinia virus is associated with reduced virulence in vivo. Virology. 1990 February; 174(2): 625-9. PubMed PMID: 2154895.

49. Corbett M, Bogers W M, Heeney J L, Gerber S, Genin C, Didierlaurent A, Oostermeijer H, Dubbes R, Braskamp G, Lerondel S, Gomez C E, Esteban M, Wagner R, Kondova I, Mooij P, Balla-Jhagjhoorsingh S, Beenhakker N, Koopman G, van der Burg S, Kraehenbuhl J P, Le Pape A. Aerosol immunization with NYVAC and MVA vectored vaccines is safe, simple, and immunogenic. Proc Natl Acad Sci USA. 2008 Feb. 12; 105(6):2046-51. doi: 10.1073/pnas.0705191105. Epub 2008 Feb. 11. PubMed PMID: 18270165; PubMed Central PMCID: PMC2538878.

50. Cox W I, Tartaglia J, Paoletti E. Induction of cytotoxic T lymphocytes by recombinant canarypox (ALVAC) and attenuated vaccinia (NYVAC) viruses expressing the HIV-1 envelope glycoprotein. Virology. 1993 August; 195(2):845-50. PubMed PMID: 8337851.

51. Cromwell M A, Veazey R S, Altman J D, Mansfield K G, Glickman R, Allen T M, Watkins D I, Lackner A A, Johnson R P. Induction of mucosal homing virus-specific CD8(+) T lymphocytes by attenuated simian immunodeficiency virus. J Virol. 2000 September; 74(18):8762-6. PubMed PMID: 10954580; PubMed Central PMCID: PMC116390.

52. Dai K, Liu Y, Liu M, Xu J, Huang W, Huang X, Liu L, Wan Y, Hao Y, Shao Y. Pathogenicity and immunogenicity of recombinant Tiantan Vaccinia Virus with deleted C12L and A53R genes. Vaccine. 2008 Sep. 15; 26(39):5062-71. doi: 10.1016/j.vaccine.2008.06.011. Epub 2008 Jun. 23. PubMed PMID: 18573290.

53. Damle N K, Klussman K, Linsley P S, Aruffo A. Differential costimulatory effects of adhesion molecules B7, ICAM-1, LFA-3, and VCAM-1 on resting and antigen-primed CD4+ T lymphocytes. J Immunol. 1992 Apr. 1; 148(7): 1985-92. PubMed PMID: 1372018.

54. Davis I D, Chen Q, Morris L, Quirk J, Stanley M, Tavarnesi M L, Parente P, Cavicchiolo T, Hopkins W, Jackson H, Dimopoulos N, Tai T Y, MacGregor D, Browning J, Svobodova S, Caron D, Maraskovsky E, Old L J, Chen W, Cebon J. Blood dendritic cells generated with Flt3 ligand and CD40 ligand prime CD8+ T cells efficiently in cancer patients. J Immunother. 2006 September-October; 29(5): 499-511. PubMed PMID: 16971806.

55. Day S L, Ramshaw I A, Ramsay A J, Ranasinghe C. Differential effects of the type I interferons alpha4, beta, and epsilon on antiviral activity and vaccine efficacy. J Immunol. 2008 Jun. 1; 180(11):7158-66. PubMed PMID: 18490714.

56. De Filette M, Min Jou W, Birkett A, Lyons K, Schultz B, Tonkyro A, Resch S, Fiers W. Universal influenza A vaccine: optimization of M2-based constructs. Virology. 2005 Jun. 20; 337(1): 149-61. PubMed PMID: 15914228.

57. Demberg T, Robert-Guroff M. Mucosal immunity and protection against HIV/SIV infection: strategies and challenges for vaccine design. Int Rev Immunol. 2009;28(1)20-48. doi: 10.1080/08830180802684331. Review. PubMed PMID: 19241252; PubMed Central PMCID: PMC3466469.

58. Didierlaurent A, Ramirez J C, Gherardi M, Zimmerli S C, Graf M, Orbea H A, Pantaleo G, Wagner R, Esteban M, Kraehenbuhl J P, Sirard J C. Attenuated poxviruses expressing a synthetic HIV protein stimulate HLA-A2-restricted cytotoxic T-cell responses. Vaccine. 2004 Sep. 3; 22(25-26): 3395-403. PubMed PMID: 15308364.

59. Diebold S S, Kaisho T, Hemmi H, Akira S, Reis e Sousa C. Innate antiviral responses by means of TLR7-mediated recognition of single-stranded RNA. Science. 2004 Mar. 5; 303(5663): 1529-31. Epub 2004 Feb. 19. PubMed PMID: 14976261.

60. Dinglasan R R, Jacobs-Lorena M. Flipping the paradigm on malaria transmission-blocking vaccines. Trends Parasitol. 2008 August; 24(8):364-70. doi: 10.1016/j.pt.2008.05.002. Epub 2008 Jul. 1. Review. PubMed PMID: 18599352.

61. Dinglasan R R, Kalume D E, Kanzok S M, Ghosh A K, Muratova O, Pandey A, Jacobs-Lorena M. Disruption of *Plasmodium falciparum* development by antibodies against a conserved mosquito midgut antigen. Proc Natl Acad Sci USA. 2007 Aug. 14; 104(33): 13461-6. Epub 2007 Aug. 2. PubMed PMID: 17673553; PubMed Central PMCID: PMC1948931.

62. Dorrell L, Williams P, Suttill A, Brown D, Roberts J, Conlon C, Hanke T, McMichael A. Safety and tolerability of recombinant modified vaccinia virus Ankara expressing an HIV-1 gag/multiepitope immunogen (MVA.HIVA) in HIV-1-infected persons receiving combination antiretroviral therapy. Vaccine. 2007 Apr. 30; 25(17):3277-83. Epub 2007 Jan. 11. PubMed PMID: 17257714.

63. Dorrell L, Yang H, Ondondo B, Dong T, di Gleria K, Suttill A, Conlon C, Brown D, Williams P, Bowness P, Goonetilleke N, Rostron T, Rowland-Jones S, Hanke T, McMichael A. Expansion and diversification of virus-specific T cells following immunization of human immunodeficiency virus type 1 (HIV-1)-infected individuals with a recombinant modified vaccinia virus Ankara/HIV-1 Gag vaccine. J Virol. 2006 May; 80(10):4705-16. PubMed PMID: 16641264; PubMed Central PMCID: PMC 1472080.

64. Dorrell L. Therapeutic immunization strategies for the control of HIV-1. Expert Rev Vaccines. 2005 August; 4(4): 513-20. Review. PubMed PMID: 16117708.

65. Draper S J, Goodman A L, Biswas S, Forbes E K, Moore A C, Gilbert S C, Hill A V. Recombinant viral vaccines expressing merozoite surface protein-1 induce antibody- and T cell-mediated multistage protection against malaria. Cell Host Microbe. 2009 Jan. 22; 5(1):95-105. doi: 10.1016/j.chom.2008.12.004. PubMed PMID: 19154991; PubMed Central PMCID: PMC2663714.

66. Draper S J, Moore A C, Goodman A L, Long C A, Holder A A, Gilbert S C, Hill F, Hill A V. Effective induction of high-titer antibodies by viral vector vaccines. Nat Med. 2008 August; 14(8):819-21. doi: 10.1038/nm. 1850. Epub 2008 Jul. 27. PubMed PMID: 18660818.

67. Dreicer R, Stadler W M, Ahmann F R, Whiteside T, Bizouarne N, Acres B, Limacher J M, Squiban P, Pantuck A. MVA-MUC1-IL2 vaccine immunotherapy (TG4010) improves PSA doubling time in patients with prostate cancer with biochemical failure. Invest New Drugs. 2009 August; 27(4):379-86. doi: 10.1007/s10637-008-9187-3. Epub 2008 Oct. 18. PubMed PMID: 18931824.

68. Dénes B, Gridley D S, Fodor N, Takátsy Z, Timiryasova T M, Fodor I. Attenuation of a vaccine strain of vaccinia virus via inactivation of interferon viroceptor. J Gene Med. 2006 July; 8(7):814-23. PubMed PMID: 16634110.

69. Earl P L, Americo J L, Wyatt L S, Eller L A, Whitbeck J C, Cohen G H, Eisenberg R J, Hartmann C J, Jackson D L, Kulesh D A, Martinez M J, Miller D M, Mucker E M, Shamblin J D, Zwiers S H, Huggins J W, Jahrling P B, Moss B. Immunogenicity of a highly attenuated MVA smallpox vaccine and protection against monkeypox. Nature. 2004 Mar. 11; 428(6979): 182-5. PubMed PMID: 15014500.

70. Ellis R D, Sagara I, Doumbo O, Wu Y. Blood stage vaccines for *Plasmodium falciparum*: current status and the way forward. Hum Vaccin. 2010 August; 6(8):627-34. Review. PubMed PMID: 20519960; PubMed Central PMCID: PMC3056062.

71. Ember S W, Ren H, Ferguson B J, Smith G L. Vaccinia virus protein C4 inhibits NF-KB activation and promotes virus virulence. J Gen Virol. 2012 October; 93(Pt 10):2098-108. doi: 10.1099/vir.0.045070-0. Epub 2012 Jul. 12. PubMed PMID: 22791606; PubMed Central PMCID: PMC3541790.

72. Engler R J, Kenner J, Leung D Y. Smallpox vaccination: Risk considerations for patients with atopic dermatitis. J Allergy Clin Immunol. 2002 September; 110(3):357-65. PubMed PMID: 12209080.

73. Estcourt M J, Ramsay A J, Brooks A, Thomson S A, Medveckzy C J, Ramshaw I A. Prime-boost immunization generates a high frequency, high-avidity CD8(+) cytotoxic T lymphocyte population. Int Immunol. 2002 January; 14(1): 31-7. PubMed PMID: 11751749.

74. Esteban M. Attenuated poxvirus vectors MVA and NYVAC as promising vaccine candidates against HIV/AIDS. Hum Vaccin. 2009 December; 5(12):867-71. Epub 2009 Dec. 3. Review. PubMed PMID: 19786840.

75. Ferrier-Rembert A, Drillien R, Tournier J N, Garin D, Crance J M. Short- and long-term immunogenicity and protection induced by non-replicating smallpox vaccine candidates in mice and comparison with the traditional 1st generation vaccine. Vaccine. 2008 Mar. 25; 26(14): 1794-804. doi: 10.1016/j.vaccine.2007.12.059. Epub 2008 Feb. 12. PubMed PMID: 18336966.

76. Flexner C, Hügin A, Moss B. Prevention of vaccinia virus infection in immunodeficient mice by vector-directed IL-2 expression. Nature. 1987 November 19-25; 330(6145): 259-62. PubMed PMID: 3118219.

77. Frahm N, Kiepiela P, Adams S, Linde C H, Hewitt H S, Sango K, Feeney M E, Addo M M, Lichterfeld M, Lahaie M P, Pae E, Wurcel A G, Roach T, St John M A, Altfeld M, Marincola F M, Moore C, Mallal S, Carrington M, Heckerman D, Allen T M, Mullins J I, Korber B T, Goulder P J, Walker B D, Brander C. Control of human immunodeficiency virus replication by cytotoxic T lymphocytes targeting subdominant epitopes. Nat Immunol. 2006 February; 7(2): 173-8. Epub 2005 Dec. 20. PubMed PMID: 16369537.

78. Frahm N, Adams S, Kiepiela P, Linde C H, Hewitt H S, Lichterfeld M, Sango K, Brown N V, Pae E, Wurcel A G, Altfeld M, Feeney M E, Allen T M, Roach T, St John M A, Daar E S, Rosenberg E, Korber B, Marincola F, Walker B D, Goulder P J, Brander C. HLA-B63 presents HLA-B57/B58-restricted cytotoxic T-lymphocyte epitopes and is associated with low human immunodeficiency virus load. J Virol. 2005 August; 79(16):10218-25. PubMed PMID: 16051815; PubMed Central PMCID: PMC 1182636.

79. Franchi L, Muñoz-Planillo R, Núñez G. Sensing and reacting to microbes through the inflammasomes. Nat Immunol. 2012 Mar. 19; 13(4):325-32. doi: 10.1038/ni.2231. Review. PubMed PMID: 22430785; PubMed Central PMCID: PMC3449002.

80. Franchi L, Stoolman J, Kanneganti T D, Verma A, Ramphal R, Núñez G, Critical role for Ipaf in Pseudomonas aeruginosa-induced caspase-1 activation. Eur J Immunol. 2007 November; 37(11):3030-9. PubMed PMID: 17935074.

81. Franchi L, Amer A, Body-Malapel M, Kanneganti T D, Ozören N, Jagirdar R, Inohara N, Vandenabeele P, Bertin J, Coyle A, Grant E P, Núñez G. Cytosolic flagellin requires Ipaf for activation of caspase-1 and interleukin lbeta in salmonella-infected macrophages. Nat Immunol. 2006 June; 7(6):576-82. Epub 2006 Apr. 30. PubMed PMID: 16648852.

82. Gallego-Gómez J C, Risco C, Rodriguez D, Cabezas P, Guerra S, Carrascosa J L, Esteban M. Differences in virus-induced cell morphology and in virus maturation between MVA and other strains (WR, Ankara, and NYCBH) of vaccinia virus in infected human cells. J Virol. 2003 October; 77(19): 10606-22. PubMed PMID: 12970445; PubMed Central PMCID: PMC228399.

83. Genton B, Betuela I, Felger I, Al-Yaman F, Anders R F, Saul A, Rare L, Baisor M, Lorry K, Brown G V, Pye D, Irving D O, Smith T A, Beck H P, Alpers M P. A recombinant blood-stage malaria vaccine reduces *Plasmodium falciparum* density and exerts selective pressure on parasite populations in a phase 1-2b trial in Papua New Guinea. J Infect Dis. 2002 Mar. 15; 185(6):820-7. Epub 2002 Feb. 14. PubMed PMID: 11920300.

84. Gherardi M M, Esteban M. Recombinant poxviruses as mucosal vaccine vectors. J Gen Virol. 2005 November; 86(Pt 11):2925-36. Review. PubMed PMID: 16227213.

85. Gherardi M M, Nájera J L, Pérez-Jiménez E, Guerra S, Garcia-Sastre A, Esteban M. Prime-boost immunization schedules based on influenza virus and vaccinia virus vectors potentiate cellular immune responses against human immunodeficiency virus Env protein systemically and in the genitorectal draining lymph nodes. J Virol. 2003 June; 77(12):7048-57. PubMed PMID: 12768024; PubMed Central PMCID: PMC 156204.

86. Gillard S, Spehner D, Drillien R, Kirn A. Localization and sequence of a vaccinia virus gene required for multiplication in human cells. Proc Natl Acad Sci USA. 1986 August; 83(15):5573-7. PubMed PMID: 3461450; PubMed Central PMCID: PMC386330.

87. Gilliet M, Cao W, Liu Y J. Plasmacytoid dendritic cells: sensing nucleic acids in viral infection and autoimmune diseases. Nat Rev Immunol. 2008 August; 8(8):594-606. doi: 10.1038/nri2358. Review. PubMed PMID: 18641647.

88. Goebel S J, Johnson G P, Perkus M E, Davis S W, Winslow J P, Paoletti E. The complete DNA sequence of vaccinia virus. Virology. 1990 November; 179(1):247-66, 517-63. PubMed PMID: 2219722.

89. Goodman A L, Forbes E K, Williams A R, Douglas A D, de Cassan S C, Bauza K, Biswas S, Dicks M D, Llewellyn D, Moore A C, Janse C J, Franke-Fayard B M, Gilbert S C, Hill A V, Pleass R J, Draper S J. The utility of *Plasmodium berghei* as a rodent model for anti-merozoite malaria vaccine assessment. Sci Rep. 2013; 3:1706. doi: 10.1038/srep01706. PubMed PMID: 23609325; PubMed Central PMCID: PMC3632886.

90. Goodman A L, Draper S J. Blood-stage malaria vaccines—recent progress and future challenges. Ann Trop Med Parasitol. 2010 April; 104(3): 189-211. doi: 10.1179/136485910X12647085215534. Review. PubMed PMID: 20507694.

91. Gudmundsdotter L, Nilsson C, Brave A, Hejdeman B, Earl P, Moss B, Robb M, Cox J, Michael N, Marovich M, Biberfeld G, Sandström E, Wahren B. Recombinant Modified Vaccinia Ankara (MVA) effectively boosts DNA-primed HIV-specific immune responses in humans despite pre-existing vaccinia immunity. Vaccine. 2009 July 16; 27(33): 4468-74. doi: 10.1016/j.vaccine.2009.05.018. Epub 2009 May 29. PubMed PMID: 19450644.

92. Guillot L, Le Goffic R, Bloch S, Escriou N, Akira S, Chignard M, Si-Tahar M. Involvement of toll-like receptor 3 in the immune response of lung epithelial cells to double-stranded RNA and influenza A virus. J Biol Chem. 2005 Feb. 18; 280(7):5571-80. Epub 2004 Dec. 3. PubMed PMID: 15579900.

93. Gulley J L, Arlen P M, Madan R A, Tsang K Y, Pazdur M P, Skarupa L, Jones J L, Poole D J, Higgins J P, Hodge J W, Cereda V, Vergati M, Steinberg S M, Halabi S, Jones E, Chen C, Parnes H, Wright J J, Dahut W L, Schlom J. Immunologic and prognostic factors associated with overall survival employing a poxviral-based PSA vaccine in metastatic castrate-resistant prostate cancer. Cancer Immunol Immunother. 2010 May; 59(5):663-74. doi: 10.1007/s00262-009-0782-8. Epub 2009 Nov. 5. PubMed PMID: 19890632; PubMed Central PMCID: PMC2832083.

94. Gulley J L, Arlen P M, Bastian A, Morin S, Marte J, Beetham P, Tsang K Y, Yokokawa J, Hodge J W, Ménard C, Camphausen K, Coleman C N, Sullivan F, Steinberg S M, Schlom J, Dahut W. Combining a recombinant cancer vaccine with standard definitive radiotherapy in patients with localized prostate cancer. Clin Cancer Res. 2005 May 1; 11(9):3353-62. Erratum in: Clin Cancer Res. 2006 Jan. 1; 12(1):322. PubMed PMID: 15867235.

95. Gómez C E, Perdiguero B, Nájera J L, Sorzano C O, Jiménez V, González-Sanz R, Esteban M. Removal of vaccinia virus genes that block interferon type I and II pathways improves adaptive and memory responses of the HIV/AIDS vaccine candidate NYVAC-C in mice. J Virol. 2012 May; 86(9):5026-38. doi: 10.1128/JVI.06684-11. Epub 2012 Mar. 14. PubMed PMID: 22419805; PubMed Central PMCID: PMC3347383.

96. Gómez C E, Nájera J L, Krupa M, Esteban M. The poxvirus vectors MVA and NYVAC as gene delivery systems for vaccination against infectious diseases and cancer. Curr Gene Ther. 2008 April; 8(2):97-120. Review. PubMed PMID: 18393831.

97. Gómez C E, Nájera J L, Domingo-Gil E, Ochoa-Callejero L, González-Aseguinolaza G, Esteban M. Virus distribution of the attenuated MVA and NYVAC poxvirus strains in mice. J Gen Virol. 2007 September; 88(Pt 9):2473-8. PubMed PMID: 17698656.

98. Gómez C E, Nájera J L, Jiménez V, Bieler K, Wild J, Kostic L, Heidari S, Chen M, Frachette M J, Pantaleo G, Wolf H, Liljestrom P, Wagner R, Esteban M. Generation and immunogenicity of novel HIV/AIDS vaccine candidates targeting HIV-1 Env/Gag-Pol-Nef antigens of clade C. Vaccine. 2007 Mar. 1; 25(11): 1969-92. Epub 2006 Dec. 6. PubMed PMID: 17224219.

99. Gómez C E, Nájera J L, Jiménez E P, Jiménez V, Wagner R, Graf M, Frachette M J, Liljestrom P, Pantaleo G, Esteban M. Head-to-head comparison on the immunogenicity of two HIV/AIDS vaccine candidates based on the attenuated poxvirus strains MVA and NYVAC co-expressing in a single locus the HIV-1BX08 gp120 and HIV-1(IIIB) Gag-Pol-Nef proteins of clade B. Vaccine. 2007 Apr. 12; 25(15):2863-85. Epub 2006 Oct. 16. PubMed PMID: 17113200.

100. Gómez C E, Abaitua F, Rodriguez D, Esteban M. Efficient CD8+ T cell response to the HIV-env V3 loop epitope from multiple virus isolates by a DNA prime/vaccinia virus boost (rWR and rMVA strains) immunization regime and enhancement by the cytokine IFN-gamma. Virus Res. 2004 Sep. 15; 105(1): 11-22. PubMed PMID: 15325077.

101. Halsell J S, Riddle J R, Atwood J E, Gardner P, Shope R, Poland G A, Gray G C, Ostroff S, Eckart R E, Hospenthal D R, Gibson R L, Grabenstein J D, Arness M K, Tornberg D N; Department of Defense Smallpox Vaccination Clinical Evaluation Team. Myopericarditis following smallpox vaccination among vaccinia-naive US military personnel. JAMA. 2003 Jun. 25; 289(24):3283-9. PubMed PMID: 12824210.

102. Hanke T, Goonetilleke N, McMichael A J, Dorrell L. Clinical experience with plasmid DNA—and modified vaccinia virus Ankara-vectored human immunodeficiency virus type 1 clade A vaccine focusing on T-cell induction. J Gen Virol. 2007 January; 88(Pt 1): 1-12. Review. Erratum in: J Gen Virol. 2008 February; 89(Pt 2):609. Goonetilleke, Nilu [added]. PubMed PMID: 17170430.

103. Harari A, Bart P A, Stohr W, Tapia G, Garcia M, Medjitna-Rais E, Burnet S, Cellerai C, Erlwein O, Barber T, Moog C, Liljestrom P, Wagner R, Wolf H, Kraehenbuhl J P, Esteban M, Heeney J, Frachette M J, Tartaglia J, McCormack S, Babiker A, Weber J, Pantaleo G. An HIV-1 clade C DNA prime, NYVAC boost vaccine regimen induces reliable, polyfunctional, and long-lasting T cell responses. J Exp Med. 2008 Jan. 21; 205(1):63-77. doi: 10.1084/jem.20071331. Epub 2008 Jan. 14. PubMed PMID: 18195071; PubMed Central PMCID: PMC2234371.

104. Hasan U, Chaffois C, Gaillard C, Saulnier V, Merck E, Tancredi S, Guiet C, Brière F, Vlach J, Lebecque S, Trinchieri G, Bates E E. Human TLR10 is a functional receptor, expressed by B cells and plasmacytoid dendritic cells, which activates gene transcription through MyD88. J Immunol. 2005 Mar. 1; 174(5):2942-50. PubMed PMID: 15728506.

105. Hayashi F, Means T K, Luster A D. Toll-like receptors stimulate human neutrophil function. Blood. 2003 Oct. 1; 102(7):2660-9. Epub 2003 Jun. 26. PubMed PMID: 12829592.

106. Hayashi F, Smith K D, Ozinsky A, Hawn T R, Yi E C, Goodlett D R, Eng J K, Akira S, Underhill D M, Aderem A. The innate immune response to bacterial flagellin is mediated by Toll-like receptor 5. Nature. 2001 Apr. 26; 410(6832): 1099-103. PubMed PMID: 11323673.

107. Heil F, Hemmi H, Hochrein H, Ampenberger F, Kirschning C, Akira S, Lipford G, Wagner H, Bauer S. Species-specific recognition of single-stranded RNA via toll-like receptor 7 and 8. Science. 2004 Mar. 5; 303(5663): 1526-9. Epub 2004 Feb. 19. PubMed PMID: 14976262.

108. Hel Z, Tsai W P, Thornton A, Nacsa J, Giuliani L, Tryniszewska E, Poudyal M, Venzon D, Wang X, Altman J, Watkins D I, Lu W, von Gegerfelt A, Felber B K, Tartaglia J, Pavlakis G N, Franchini G. Potentiation of simian immunodeficiency virus (SIV)-specific CD4(+) and CD8(+) T cell responses by a DNA-SIV and NYVAC-SIV prime/boost regimen. J Immunol. 2001 Dec. 15; 167(12):7180-91. PubMed PMID: 11739541.

109. Hemmi H, Kaisho T, Takeuchi O, Sato S, Sanjo H, Hoshino K, Horiuchi T, Tomizawa H, Takeda K, Akira S. Small anti-viral compounds activate immune cells via the TLR7 MyD88-dependent signaling pathway. Nat Immunol. 2002 February; 3(2): 196-200. Epub 2002 Jan. 22. PubMed PMID: 11812998.

110. Hemmi H, Takeuchi O, Kawai T, Kaisho T, Sato S, Sanjo H, Matsumoto M, Hoshino K, Wagner H, Takeda K, Akira S. A Toll-like receptor recognizes bacterial DNA. Nature. 2000 Dec. 7; 408(6813):740-5. Erratum in: Nature 2001 Feb. 1; 409(6820):646. PubMed PMID: 11130078.

111. Henderson D A. Lessons from the eradication campaigns. Vaccine. 1999 Oct. 29; 17 Suppl 3:S53-5. PubMed PMID: 10559535.

112. Henderson D A. The eradication of smallpox. Sci Am. 1976 October; 235(4):25-33. PubMed PMID: 788150.

113. Heppner D G Jr, Kester K E, Ockenhouse C F, Tornieporth N, Ofori O, Lyon J A, Stewart V A, Dubois P, Lanar D E, Krzych U, Moris P, Angov E, Cummings J F, Leach A, Hall B T, Dutta S, Schwenk R, Hillier C, Barbosa A, Ware L A, Nair L, Darko C A, Withers M R, Ogutu B, Polhemus M E, Fukuda M, Pichyangkul S, Gettyacamin M, Diggs C, Soisson L, Milman J, Dubois M C, Garcon N, Tucker K, Wittes J, Plowe C V, Thera M A, Duombo O K, Pau M G, Goudsmit J, Ballou W R, Cohen J. Towards an RTS,S-based, multi-stage, multi-antigen vaccine against falciparum malaria: progress at the Walter Reed Army Institute of Research. Vaccine. 2005 Mar. 18; 23(17-18):2243-50. Review. PubMed PMID: 15755604.

114. Hill A V. Vaccines against malaria. Philos Trans R Soc Lond B Biol Sci. 2011 Oct. 12; 366(1579):2806-14. doi: 10.1098/rstb.2011.0091. Review. PubMed PMID: 21893544; PubMed Central PMCID: PMC3146776.

115. Hodge J W, Chakraborty M, Kudo-Saito C, Garnett C T, Schlom J. Multiple costimulatory modalities enhance CTL avidity. J Immunol. 2005 May 15; 174(10):5994-6004. Erratum in: J Immunol. 2005 Jun. 15; 174(12):8220. PubMed PMID: 15879092; PubMed Central PMCID: PMC 1924685.

116. Hodge J W, Poole D J, Aarts W M, Gómez Yafal A, Gritz L, Schlom J. Modified vaccinia virus ankara recombinants are as potent as vaccinia recombinants in diversified prime and boost vaccine regimens to elicit therapeutic antitumor responses. Cancer Res. 2003 Nov. 15; 63(22): 7942-9. PubMed PMID: 14633725.

117. Hodge J W, Sabzevari H, Yafal A G, Gritz L, Lorenz M G, Schlom J. A triad of costimulatory molecules synergize to amplify T-cell activation. Cancer Res. 1999 Nov. 15; 59(22):5800-7. PubMed PMID: 10582702.

118. Hoebe K, Janssen E, Beutler B. The interface between innate and adaptive immunity. Nat Immunol. 2004 October; 5(10):971-4. Review. PubMed PMID: 15454919.

119. Hoffman S L, Billingsley P F, James E, Richman A, Loyevsky M, Li T, Chakravarty S, Gunasekera A, Chattopadhyay R, Li M, Stafford R, Ahumada A, Epstein J E, Sedegah M, Reyes S, Richie T L, Lyke K E, Edelman R, Laurens M B, Plowe C V, Sim B K. Development of a metabolically active, non-replicating sporozoite vaccine to prevent Plasmodium falciparum malaria. Hum Vaccin. 2010 January; 6(1):97-106. Epub 2010 Jan. 21. Review. PubMed PMID: 19946222.

120. Hoffman S L, Goh L M, Luke T C, Schneider I, Le T P, Doolan D L, Sacci J, de la Vega P, Dowler M, Paul C, Gordon D M, Stoute J A, Church L W, Sedegah M, Heppner D G, Ballou W R, Richie T L. Protection of humans against malaria by immunization with radiation-attenuated *Plasmodium falciparum* sporozoites. J Infect Dis. 2002 Apr. 15; 185(8): 1155-64. Epub 2002 Apr. 1. PubMed PMID: 11930326.

121. Hoshino K, Takeuchi O, Kawai T, Sanjo H, Ogawa T, Takeda Y, Takeda K, Akira S. Cutting edge: Toll-like receptor 4 (TLR4)-deficient mice are hyporesponsive to lipopolysaccharide: evidence for TLR4 as the Lps gene product. J Immunol. 1999 Apr. 1; 162(7):3749-52. PubMed PMID: 10201887.

122. Howell M D, Gallo R L, Boguniewicz M, Jones J F, Wong C, Streib J E, Leung D Y. Cytokine milieu of atopic dermatitis skin subverts the innate immune response to vaccinia virus. Immunity. 2006 March; 24(3):341-8. PubMed PMID: 16546102.

123. Hu S L, Abrams K, Barber G N, Moran P, Zarling J M, Langlois A J, Kuller L, Morton W R, Benveniste R E. Protection of macaques against SIV infection by subunit vaccines of SIV envelope glycoprotein gp160. Science. 1992 Jan. 24; 255(5043):456-9. PubMed PMID: 1531159.

124. Huang X, Lu B, Yu W, Fang Q, Liu L, Zhuang K, Shen T, Wang H, Tian P, Zhang L, Chen Z. A novel replication-competent vaccinia vector MVTT is superior to MVA for inducing high levels of neutralizing antibody via mucosal vaccination. PLoS One. 2009; 4(1):e4180. doi: 10.1371/journal.pone.0004180. Epub 2009 Jan. 13. PubMed PMID: 19159014; PubMed Central PMCID: PMC2613559.

125. Huang X, Liu L, Ren L, Qiu C, Wan Y, Xu J. Mucosal priming with replicative Tiantan vaccinia and systemic boosting with DNA vaccine raised strong mucosal and systemic HIV-specific immune responses. Vaccine. 2007 Dec. 17; 25(52):8874-84. Epub 2007 Sep. 24. PubMed PMID: 18061316.

126. Huleatt J W, Nakaar V, Desai P, Huang Y, Hewitt D, Jacobs A, Tang J, McDonald W, Song L, Evans R K, Umlauf S, Tussey L, Powell T J. Potent immunogenicity and efficacy of a universal influenza vaccine candidate comprising a recombinant fusion protein linking influenza M2e to the TLR5 ligand flagellin. Vaccine. 2008 Jan. 10; 26(2):201-14. Epub 2007 Nov. 20. PubMed PMID: 18063235.

127. Ishizaki H, Song G Y, Srivastava T, Carroll K D, Shahabi V, Manuel E R, Diamond D J, Ellenhorn J D. Heterologous prime/boost immunization with p53-based vaccines combined with toll-like receptor stimulation enhances tumor regression. J Immunother. 2010 July-August; 33(6):609-17. doi: 10.1097/CJI.0b013e3181 e032c6. PubMed PMID: 20551836; PubMed Central PMCID: PMC3523364.

128. Iwasaki A, Medzhitov R. Toll-like receptor control of the adaptive immune responses. Nat Immunol. 2004 October; 5(10):987-95. Review. PubMed PMID: 15454922.

129. Jacobs B L, Langland J O, Kibler K V, Denzler K L, White S D, Holechek S A, Wong S, Huynh T, Baskin C R. Vaccinia virus vaccines: past, present and future. Antiviral Res. 2009 October; 84(1): 1-13. doi: 10.1016/j.antiviral.2009.06.006. Epub 2009 Jun. 26. Review. PubMed PMID: 19563829; PubMed Central PMCID: PMC2742674.

130. Jordan J A, Guo R F, Yun E C, Sarma V, Warner R L, Crouch L D, Senaldi G, Ulich T R, Ward P A. Role of IL-18 in acute lung inflammation. J Immunol. 2001 Dec. 15; 167(12):7060-8. PubMed PMID: 11739527.

131. Kaba S A, Brando C, Guo Q, Mittelholzer C, Raman S, Tropel D, Aebi U, Burkhard P, Lanar D E. A nonadjuvanted polypeptide nanoparticle vaccine confers long-lasting protection against rodent malaria. J Immunol. 2009 Dec. 1; 183(11):7268-77. doi: 10.4049/jimmunol.0901957. Epub 2009 Nov. 13. PubMed PMID: 19915055A 132. Kadowaki N, Ho S, Antonenko S, Malefyt R W, Kastelein R A, Bazan F, Liu Y J. Subsets of human dendritic cell precursors express different toll-like receptors and respond to different microbial antigens. J Exp Med. 2001 Sep. 17; 194(6):863-9. PubMed PMID: 11561001; PubMed Central PMCID: PMC2195968.

133. Kantoff P W, Schuetz T J, Blumenstein B A, Glode L M, Bilhartz D L, Wyand M, Manson K, Panicali D L, Laus R, Schlom J, Dahut W L, Arlen P M, Gulley J L, Godfrey W R. Overall survival analysis of a phase II randomized controlled trial of a Poxviral-based PSA-targeted immunotherapy in metastatic castration-resistant prostate cancer. J Clin Oncol. 2010 Mar. 1; 28(7): 1099-105. doi: 10.1200/JCO.2009.25.0597. Epub 2010 Jan. 25. PubMed PMID: 20100959; PubMed Central PMCID: PMC2834462.

134. Kantoff P W, Higano C S, Shore N D, Berger E R, Small E J, Penson D F, Redfern C H, Ferrari A C, Dreicer R, Sims R B, Xu Y, Frohlich M W, Schellhammer P F; IMPACT Study Investigators. Sipuleucel-T immunotherapy for castration-resistant prostate cancer. N Engl J Med. 2010 Jul. 29; 363(5):411-22. doi: 10.1056/NEJMoa1001294. PubMed PMID: 20818862.

135. Karkhanis L U, Ross T M. Mucosal vaccine vectors: replication-competent versus replication-deficient poxviruses. Curr Pharm Des. 2007; 13(19):2015-23. Review. PubMed PMID: 17627535.

136. Kass E, Panicali D L, Mazzara G, Schlom J, Greiner J W. Granulocyte/macrophage-colony stimulating factor produced by recombinant avian poxviruses enriches the regional lymph nodes with antigen-presenting cells and acts as an immunoadjuvant. Cancer Res. 2001 Jan. 1; 61(1):206-14. PubMed PMID: 11196163.

137. Kaufman H L, Wang W, Manola J, DiPaola R S, Ko Y J, Sweeney C, Whiteside T L, Schlom J, Wilding G, Weiner L M. Phase II randomized study of vaccine treatment of advanced prostate cancer (E7897): a trial of the Eastern Cooperative Oncology Group. J Clin Oncol. 2004 Jun. 1; 22(11):2122-32. PubMed PMID: 15169798.

138. Kawai T, Akira S. TLR signaling. Semin Immunol. 2007 February; 19(1):24-32. Epub 2007 Feb. 1. Review. PubMed PMID: 17275323.

139. Kibler K V, Gomez C E, Perdiguero B, Wong S, Huynh T, Holechek S, Arndt W, Jimenez V, Gonzalez-Sanz R, Denzler K, Haddad E K, Wagner R, Sékaly R P, Tartaglia J, Pantaleo G, Jacobs B L, Esteban M. Improved NYVAC-based vaccine vectors. PLoS One. 2011; 6(11):e25674. doi: 10.1371/journal.pone.0025674. Epub 2011 Nov. 9. PubMed PMID: 22096477; PubMed Central PMCID: PMC3212513.

140. Kim D W, Krishnamurthy V, Bines S D, Kaufman H L. TroVax, a recombinant modified vaccinia Ankara virus encoding 5T4: lessons learned and future development. Hum Vaccin. 2010 October; 6(10):784-91. Epub 2010 Oct. 1. Review. PubMed PMID: 20975327.

141. Kotwal G J, Moss B. Vaccinia virus encodes two proteins that are structurally related to members of the plasma serine protease inhibitor superfamily. J Virol. 1989 February; 63(2):600-6. Erratum in: J Virol 1990 February; 64(2):966. PubMed PMID: 2783466; PubMed Central PMCID: PMC247729.

142. Kotwal G J, Moss B. Analysis of a large cluster of nonessential genes deleted from a vaccinia virus terminal transposition mutant. Virology. 1988 December; 167(2):524-37. PubMed PMID: 2849238.

143. Krieg A M. CpG motifs in bacterial DNA and their immune effects. Annu Rev Immunol. 2002; 20:709-60. Epub 2001 Oct. 4. Review. PubMed PMID: 11861616.

144. Krupa M, Canamero M, Gomez C E, Najera J L, Gil J, Esteban M. Immunization with recombinant DNA and modified vaccinia virus Ankara (MVA) vectors delivering PSCA and STEAP1 antigens inhibits prostate cancer progression. Vaccine. 2011 Feb. 4; 29(7): 1504-13. doi: 10.1016/j.vaccine.2010.12.016. Epub 2010 Dec. 21. PubMed PMID: 21182993.

145. Kumar H, Kawai T, Akira S. Toll-like receptors and innate immunity. Biochem Biophys Res Commun. 2009 Oct. 30; 388(4):621-5. doi: 10.1016/j.bbrc.2009.08.062. Epub 2009 Aug. 15. Review. PubMed PMID: 19686699.

146. Kuroda M J, Schmitz J E, Charini W A, Nickerson C E, Lifton M A, Lord C I, Forman M A, Letvin N L. Emergence of CTL coincides with clearance of virus during primary simian immunodeficiency virus infection in rhesus monkeys. J Immunol. 1999 May 1; 162(9):5127-33. PubMed PMID: 10227983.

147. Lanar D E, Tine J A, de Taisne C, Seguin M C, Cox W I, Winslow J P, Ware L A, Kauffman E B, Gordon D, Ballou W R, Paoletti E, Sadoff J C. Attenuated vaccinia virus-circumsporozoite protein recombinants confer protection against rodent malaria. Infect Immun. 1996 May; 64(5):1666-71. PubMed PMID: 8613376; PubMed Central PMCID: PMC173977.

148. Langhorne J, Ndungu F M, Sponaas A M, Marsh K. Immunity to malaria: more questions than answers. Nat Immunol. 2008 July; 9(7):725-32. doi: 10.1038/ni.f205. Review. PubMed PMID: 18563083.

149. Langhorne J, Quin S J, Sanni L A. Mouse models of blood-stage malaria infections: immune responses and cytokines involved in protection and pathology. Chem Immunol. 2002; 80:204-28. Review. PubMed PMID: 12058640.

150. Langland J O, Kash J C, Carter V, Thomas M J, Katze M G, Jacobs B L. Suppression of proinflammatory signal transduction and gene expression by the dual nucleic acid binding domains of the vaccinia virus E3L proteins. J Virol. 2006 October; 80(20): 10083-95. PubMed PMID: 17005686; PubMed Central PMCID: PMC 1617298.

151. Langland J O, Jacobs B L. Inhibition of PKR by vaccinia virus: role of the N- and C-terminal domains of E3L. Virology. 2004 Jul. 1; 324(2):419-29. PubMed PMID: 15207627.

152. Langland J O, Jacobs B L. The role of the PKR-inhibitory genes, E3L and K3L, in determining vaccinia virus host range. Virology. 2002 Jul. 20; 299(1): 133-41. PubMed PMID: 12167348.

153. Le Moigne V, Robreau G, Mahana W. Flagellin as a good carrier and potent adjuvant for Th1 response: study of mice immune response to the p27 (Rv2108) Mycobacterium tuberculosis antigen. Mol Immunol. 2008 May; 45(9):2499-507. doi: 10.1016/j.molimm.2008.01.005. Epub 2008 Mar. 4. PubMed PMID: 18289677.

154. Lechleider R J, Arlen P M, Tsang K Y, Steinberg S M, Yokokawa J, Cereda V, Camphausen K, Schlom J, Dahut W L, Gulley J L. Safety and immunologic response of a viral vaccine to prostate-specific antigen in combination with radiation therapy when metronomic-dose interleukin 2 is used as an adjuvant. Clin Cancer Res. 2008 Aug. 15; 14(16):5284-91. doi: 10.1158/1078-0432.CCR-07-5162. PubMed PMID: 18698048; PubMed Central PMCID: PMC2639763.

155. Legrand F A, Verardi P H, Chan K S, Peng Y, Jones L A, Yilma T D. Vaccinia viruses with a serpin gene deletion and expressing IFN-gamma induce potent immune responses without detectable replication in vivo. Proc Natl Acad Sci USA. 2005 Feb. 22; 102(8):2940-5. Epub 2005 Feb. 10. PubMed PMID: 15705716; PubMed Central PMCID: PMC548597.

156. Lemaitre B, Nicolas E, Michaut L, Reichhart J M, Hoffmann J A. The dorsoventral regulatory gene cassette spätzle/Toll/cactus controls the potent antifungal response in Drosophila adults. Cell. 1996 Sep. 20; 86(6):973-83. PubMed PMID: 8808632.

157. Li K, Foy E, Ferreon J C, Nakamura M, Ferreon A C, Ikeda M, Ray S C, Gale M Jr, Lemon S M. Immune evasion by hepatitis C virus NS3/4A protease-mediated cleavage of the Toll-like receptor 3 adaptor protein TRIF. Proc Natl Acad Sci USA. 2005 Feb. 22; 102(8):2992-7. Epub 2005 Feb. 14. PubMed PMID: 15710891; PubMed Central PMCID: PMC548795.

158. Liang B, Hyland L, Hou S. Nasal-associated lymphoid tissue is a site of long-term virus-specific antibody production following respiratory virus infection of mice. J Virol. 2001 June; 75(11):5416-20. PubMed PMID: 11333927; PubMed Central PMCID: PMC 114951.

159. Liu M, Acres B, Balloul J M, Bizouarne N, Paul S, Slos P, Squiban P. Gene-based vaccines and immunotherapeutics. Proc Natl Acad Sci USA. 2004 Oct. 5; 101 Suppl 2:14567-71. Epub 2004 Aug. 27. Review. PubMed PMID: 15333750; PubMed Central PMCID: PMC521989.

160. Liu M A. Immunologic basis of vaccine vectors. Immunity. 2010 Oct. 29; 33(4):504-15. doi: 10.1016/j.immuni.2010.10.004. Review. PubMed PMID: 21029961.

161. Lutz E, Yeo C J, Lillemoe K D, Biedrzycki B, Kobrin B, Herman J, Sugar E, Piantadosi S, Cameron J L, Solt S, Onners B, Tartakovsky I, Choi M, Sharma R, Illei P B, Hruban R H, Abrams R A, Le D, Jaffee E, Laheru D. A lethally irradiated allogeneic granulocyte-macrophage colony stimulating factor-secreting tumor vaccine for pancreatic adenocarcinoma. A Phase II trial of safety, efficacy, and immune activation. Ann Surg. 2011 February; 253(2): 328-35. doi: 10.1097/SLA.0b013e3181 fd271 c. PubMed PMID: 21217520; PubMed Central PMCID: PMC3085934.

162. Macete E, Aponte J J, Guinovart C, Sacarlal J, Ofori-Anyinam O, Mandomando I, Espasa M, Bevilacqua C, Leach A, Dubois M C, Heppner D G, Tello L, Milman J, Cohen J, Dubovsky F, Tornieporth N, Thompson R, Alonso P L. Safety and immunogenicity of the RTS,S/AS02A candidate malaria vaccine in children aged 1-4 in Mozambique. Trop Med Int Health. 2007 January; 12(1):37-46. PubMed PMID: 17207146.

163. Mackett M, Smith G L, Moss B. Vaccinia virus: a selectable eukaryotic cloning and expression vector. Proc Natl Acad Sci USA. 1982 December; 79(23):7415-9. PubMed PMID: 6296831; PubMed Central PMCID: PMC347350.

164. Madan R A, Arlen P M, Mohebtash M, Hodge J W, Gulley J L. Prostvac-VF: a vector-based vaccine targeting PSA in prostate cancer. Expert Opin Investig Drugs. 2009 July; 18(7): 1001-11. doi: 10.1517/13543780902997928. Review. PubMed PMID: 19548854; PubMed Central PMCID: PMC3449276.

165. malERA Consultative Group on Monitoring, Evaluation, and Surveillance. A research agenda for malaria eradication: monitoring, evaluation, and surveillance. PLoS Med. 2011 Jan. 25; 8(1):e1000400. doi: 10.1371/journal.pmed.1000400. Review. PubMed PMID: 21311581; PubMed Central PMCID: PMC3026689.

166. malERA Consultative Group on Vaccines. A research agenda for malaria eradication: vaccines. PLoS Med. 2011 Jan. 25; 8(1):e1000398. doi: 10.1371/journal.pmed.1000398. Review. PubMed PMID: 21311586; PubMed Central PMCID: PMC3026701.

167. Maloney G, Schröder M, Bowie A G. Vaccinia virus protein A52R activates p38 mitogen-activated protein kinase and potentiates lipopolysaccharide-induced interleukin-10. J Biol Chem. 2005 Sep. 2;280(35):30838-44. Epub 2005 Jul. 5. PubMed PMID: 15998638.

168. Martinez J, Huang X, Yang Y. Toll-like receptor 8-mediated activation of murine plasmacytoid dendritic cells by vaccinia viral DNA. Proc Natl Acad Sci USA. 2010 Apr. 6;107(14):6442-7. doi: 10.1073/pnas.0913291107. Epub 2010 Mar. 22. PubMed PMID: 20308556; PubMed Central PMCID: PMC2851984.

169. Mayr A, Stickl H, Müllner H K, Danner K, Singer H. [The smallpox vaccination strain MVA: marker, genetic structure, experience gained with the parenteral vaccination and behavior in organisms with a debilitated defence mechanism (author's transl)]. Zentralbl Bakteriol B. 1978 December; 167(5-6):375-90. German. PubMed PMID: 219640.

170. McCormack S, Stohr W, Barber T, Bart P A, Harari A, Moog C, Ciuffreda D, Cellerai C, Cowen M, Gamboni R, Burnet S, Legg K, Brodnicki E, Wolf H, Wagner R, Heeney J, Frachette M J, Tartaglia J, Babiker A, Pantaleo G, Weber J. EV02: a Phase I trial to compare the safety and immunogenicity of HIV DNA-C prime-NYVAC-C boost to NYVAC-C alone. Vaccine. 2008 Jun. 13; 26(25):3162-74. doi: 10.1016/j.vaccine.2008.02.072. Epub 2008 May 6. PubMed PMID: 18502003.

171. McCurdy L H, Larkin B D, Martin J E, Graham B S. Modified vaccinia Ankara: potential as an alternative smallpox vaccine. Clin Infect Dis. 2004 Jun. 15; 38(12): 1749-53. Epub 2004 May 19. PubMed PMID: 15227622.

172. McFadden G. Poxvirus tropism. Nat Rev Microbiol. 2005 March; 3(3):201-13. Review. PubMed PMID: 15738948.

173. Medzhitov R. Recognition of microorganisms and activation of the immune response. Nature. 2007 Oct. 18; 449(7164):819-26. Review. PubMed PMID: 17943118.

174. Medzhitov R, Janeway C A Jr. Decoding the patterns of self and nonself by the innate immune system. Science. 2002 Apr. 12; 296(5566):298-300. PubMed PMID: 11951031.

175. Medzhitov R, Preston-Hurlburt P, Janeway C A Jr. A human homologue of the Drosophila Toll protein signals activation of adaptive immunity. Nature. 1997 Jul. 24; 388(6640):394-7. PubMed PMID: 9237759.

176. Melief C J. Cancer immunotherapy by dendritic cells. Immunity. 2008 Sep. 19; 29(3):372-83. doi: 10.1016/j.immuni.2008.08.004. Review. PubMed PMID: 18799145.

177. Menéndez C, D'Alessandro U, ter Kuile F O. Reducing the burden of malaria in pregnancy by preventive strategies. Lancet Infect Dis. 2007 February; 7(2): 126-35. Review. PubMed PMID: 17251083.

178. Miao E A, Mao D P, Yudkovsky N, Bonneau R, Lorang C G, Warren S E, Leaf I A, Aderem A. Innate immune detection of the type III secretion apparatus through the NLRC4 inflammasome. Proc Natl Acad Sci USA. 2010 Feb. 16; 107(7):3076-80. doi: 10.1073/pnas.0913087107. Epub 2010 Feb. 1. PubMed PMID: 20133635; PubMed Central PMCID: PMC2840275.

179. Midgley C M, Putz M M, Weber J N, Smith G L. Vaccinia virus strain NYVAC induces substantially lower and qualitatively different human antibody responses compared with strains Lister and Dryvax. J Gen Virol. 2008 December; 89(Pt 12):2992-7. doi: 10.1099/vir.0.2008/004440-0. PubMed PMID: 19008384; PubMed Central PMCID: PMC2885029.

180. Milstein C. Monoclonal antibodies. Sci Am. 1980 October; 243(4):66-74. PubMed PMID: 6158758.

181. Mizel S B, Graff A H, Sriranganathan N, Ervin S, Lees C J, Lively M O, Hantgan R R, Thomas M J, Wood J, Bell B. Flagellin-F1-V fusion protein is an effective plague vaccine in mice and two species of nonhuman primates. Clin Vaccine Immunol. 2009 January; 16(1):21-8. doi: 10.1128/CVI.00333-08. Epub 2008 Nov. 5. PubMed PMID: 18987167; PubMed Central PMCID: PMC2620661.

182. Mlambo G, Kumar N. Transgenic rodent *Plasmodium berghei* parasites as tools for assessment of functional immunogenicity and optimization of human malaria vaccines. Eukaryot Cell. 2008 November; 7(11): 1875-9. doi: 10.1128/EC.00242-08. Epub 2008 Sep. 19. Review. PubMed PMID: 18806208; PubMed Central PMCID: PMC2583535.

183. Mooij P, Balla-Jhagjhoorsingh S S, Koopman G, Beenhakker N, van Haaften P, Baak I, Nieuwenhuis I G, Kondova I, Wagner R, Wolf H, Gómez C E, Nájera J L, Jiménez V, Esteban M, Heeney J L. Differential CD4+ versus CD8+ T-cell responses elicited by different poxvirus-based human immunodeficiency virus type 1 vaccine candidates provide comparable efficacies in primates. J Virol. 2008 March; 82(6):2975-88. doi: 10.1128/JVI.02216-07.

184. Muzio M, Bosisio D, Polentarutti N, D'amico G, Stoppacciaro A, Mancinelli R, van't Veer C, Penton-Rol G, Ruco L P, Allavena P, Mantovani A. Differential expression and regulation of toll-like receptors (TLR) in human leukocytes: selective expression of TLR3 in dendritic cells. J Immunol. 2000 Jun. 1; 164(11):5998-6004. PubMed PMID: 10820283.

185. Naito T, Kaneko Y, Kozbor D. Oral vaccination with modified vaccinia virus Ankara attached covalently to TMPEG-modified cationic liposomes overcomes pre-existing poxvirus immunity from recombinant vaccinia immunization. J Gen Virol. 2007 January; 88(Pt 1):61-70. PubMed PMID: 17170437; PubMed Central PMCID: PMC2501116.

186. 186: NAM J H, BANG H S, CHO H W, CHUNG Y H. Different contribution of co-stimulatory molecules B7.1 and B7.2 to the immune response to recombinant modified vaccinia virus ankara vaccine expressing prM/E proteins of Japanese encephalitis virus and two hepatitis B virus vaccines. Acta Virol. 2007; 51(2): 125-30. PubMed PMID: 17900219.

187. Nempont C, Cayet D, Rumbo M, Bompard C, Villeret V, Sirard J C. Deletion of flagellin's hypervariable region abrogates antibody-mediated neutralization and systemic activation of TLR5-dependent immunity. J Immunol. 2008 Aug. 1; 181(3):2036-43. PubMed PMID: 18641341.

188. Neutra M R, Kozlowski P A. Mucosal vaccines: the promise and the challenge. Nat Rev Immunol. 2006 February; 6(2): 148-58. Review. PubMed PMID: 16491139.

189. Nussenzweig R S, Vanderberg J, Most H, Orton C. Protective immunity produced by the injection of x-irradiated sporozoites of plasmodium *berghei*. Nature. 1967 Oct. 14; 216(5111): 160-2. PubMed PMID: 6057225.

190. Nájera J L, Gómez C E, Garcia-Arriaza J, Sorzano C O, Esteban M. Insertion of vaccinia virus C7L host range gene into NYVAC-B genome potentiates immune responses against HIV-1 antigens. PLoS One. 2010 Jun. 30; 5(6): e11406. doi: 10.1371/journal.pone.0011406. PubMed PMID: 20613977; PubMed Central PMCID: PMC2894869.

191. Nájera J L, Gómez C E, Domingo-Gil E, Gherardi M M, Esteban M. Cellular and biochemical differences between two attenuated poxvirus vaccine candidates (MVA and NYVAC) and role of the C7L gene. J Virol. 2006 June; 80(12):6033-47. PubMed PMID: 16731942; PubMed Central PMCID: PMC1472566.

192. O'Neill L A, Bowie A G. The family of five: TIR-domain-containing adaptors in Toll-like receptor signalling. Nat Rev Immunol. 2007 May; 7(5):353-64. Review. PubMed PMID: 17457343.

193. Ockenhouse C F, Sun P F, Lanar D E, Wellde B T, Hall B T, Kester K, Stoute J A, Magill A, Krzych U, Farley L, Wirtz R A, Sadoff J C, Kaslow D C, Kumar S, Church L W, Crutcher J M, Wizel B, Hoffman S, Lalvani A, Hill A V, Tine J A, Guito K P, de Taisne C, Anders R, Ballou W R, et al. Phase I/IIa safety, immunogenicity, and efficacy trial of NYVAC-Pf7, a pox-vectored, multiantigen, multistage vaccine candidate for *Plasmodium falciparum* malaria. J Infect Dis. 1998 June; 177(6): 1664-73. PubMed PMID: 9607847.

194. Ogutu B R, Apollo O J, McKinney D, Okoth W, Siangla J, Dubovsky F, Tucker K, Waitumbi J N, Diggs C, Wittes J, Malkin E, Leach A, Soisson L A, Milman J B, Otieno L, Holland C A, Polhemus M, Remich S A, Ockenhouse C F, Cohen J, Ballou W R, Martin S K, Angov E, Stewart V A, Lyon J A, Heppner D G, Withers M R; MSP-1 Malaria Vaccine Working Group. Blood stage malaria vaccine eliciting high antigen-specific antibody concentrations confers no protection to young children in Western Kenya. PLoS One. 2009; 4(3):e4708. doi: 10.1371/journal.pone.0004708. Epub 2009 Mar. 5. PubMed PMID: 19262754; PubMed Central PMCID: PMC2650803.

195. Oh S, Hodge J W, Ahlers J D, Burke D S, Schlom J, Berzofsky J A. Selective induction of high avidity CTL by altering the balance of signals from APC. J Immunol. 2003 Mar. 1; 170(5):2523-30. PubMed PMID: 12594278.

196. Oudard S, Rixe O, Beuselinck B, Linassier C, Banu E, Machiels J P, Baudard M, Ringeisen F, Velu T, Lefrere-Belda M A, Limacher J M, Fridman W H, Azizi M, Acres B, Tartour E. A phase II study of the cancer vaccine TG4010 alone and in combination with cytokines in patients with metastatic renal clear-cell carcinoma: clinical and immunological findings. Cancer Immunol Immunother. 2011 February; 60(2):261-71. doi: 10.1007/s00262-010-0935-9. Epub 2010 Nov. 11. PubMed PMID: 21069322.

197. Panicali D, Davis S W, Weinberg R L, Paoletti E. Construction of live vaccines by using genetically engineered poxviruses: biological activity of recombinant vaccinia virus expressing influenza virus hemagglutinin. Proc Natl Acad Sci USA. 1983 September; 80(17):5364-8. PubMed PMID: 6310573; PubMed Central PMCID: PMC384256.

198. Panicali D, Paoletti E. Construction of poxviruses as cloning vectors: insertion of the thymidine kinase gene from herpes simplex virus into the DNA of infectious vaccinia virus. Proc Natl Acad Sci USA. 1982 August; 79(16):4927-31. PubMed PMID: 6289324; PubMed Central PMCID: PMC346798.

199. Pantaleo G, Esteban M, Jacobs B, Tartaglia J. Poxvirus vector-based HIV vaccines. Curr Opin HIV AIDS. 2010 September; 5(5):391-6. doi: 10.1097/COH.0b013e32833d1e87. Review. PubMed PMID: 20978379.

200. Parrino J, Graham B S. Smallpox vaccines: Past, present, and future. J Allergy Clin Immunol. 2006 December; 118(6): 1320-6. Review. PubMed PMID: 17157663.

201. Peng G, Guo Z, Kiniwa Y, Voo K S, Peng W, Fu T, Wang D Y, Li Y, Wang H Y, Wang R F. Toll-like receptor 8-mediated reversal of CD4+ regulatory T cell function. Science. 2005 Aug. 26; 309(5739): 1380-4. PubMed PMID: 16123302.

202. Perkus M E, Tartaglia J, Paoletti E. Poxvirus-based vaccine candidates for cancer, AIDS, and other infectious diseases. J Leukoc Biol. 1995 July; 58(1): 1-13. Review. PubMed PMID: 7616101.

203. Perkus M E, Goebel S J, Davis S W, Johnson G P, Limbach K, Norton E K, Paoletti E. Vaccinia virus host range genes. Virology. 1990 November; 179(1):276-86. PubMed PMID: 2171207.

204. Perkus M E, Limbach K, Paoletti E. Cloning and expression of foreign genes in vaccinia virus, using a host range selection system. J Virol. 1989 September; 63(9): 3829-36. PubMed PMID: 2547999; PubMed Central PMCID: PMC250976.

205. Perkus M E, Kauffman E B, Taylor J, Mercer S, Smith D, Vanderhoven J, Paoletti E. Methodology of using vaccinia virus to express foreign genes in tissue culture. Journal of tissue culture methods. 1983; 15:72-81.

206. Perreau M, Welles H C, Harari A, Hall O, Martin R, Maillard M, Dorta G, Bart P A, Kremer E J, Tartaglia J, Wagner R, Esteban M, Levy Y, Pantaleo G. DNA/NYVAC vaccine regimen induces HIV-specific CD4 and CD8 T-cell responses in intestinal mucosa. J Virol. 2011 October;

207. Poltorak A, He X, Smirnova I, Liu M Y, Van Huffel C, Du X, Birdwell D, Alejos E, Silva M, Galanos C, Freudenberg M, Ricciardi-Castagnoli P, Layton B, Beutler B. Defective LPS signaling in C3H/HeJ and C57BL/10ScCr mice: mutations in Tlr4 gene. Science. 1998 Dec. 11; 282(5396):2085-8. PubMed PMID: 9851930.

208. Poulet H, Minke J, Pardo M C, Juillard V, Nordgren B, Audonnet J C. Development and registration of recombinant veterinary vaccines. The example of the canarypox vector platform. Vaccine. 2007 Jul. 26; 25(30):5606-12. Epub 2006 Dec. 8. Review. PubMed PMID: 17227690.

209. Quakkelaar E D, Redeker A, Haddad E K, Harari A, McCaughey S M, Duhen T, Filali-Mouhim A, Goulet J P, Loof N M, Ossendorp F, Perdiguero B, Heinen P, Gomez C E, Kibler K V, Koelle D M, Sekaly R P, Sallusto F, Lanzavecchia A, Pantaleo G, Esteban M, Tartaglia J, Jacobs B L, Melief C J. Improved innate and adaptive immunostimulation by genetically modified HIV-1 protein expressing NYVAC vectors. PLoS One. 2011 Feb. 15; 6(2):e16819. doi: 10.1371/journal.pone.0016819. PubMed PMID: 21347234; PubMed Central PMCID: PMC3039654.

210. Qureshi S T, Lariviere L, Leveque G, Clermont S, Moore K J, Gros P, Malo D. Endotoxin-tolerant mice have mutations in Toll-like receptor 4 (Tlr4). J Exp Med. 1999 Feb. 15; 189(4):615-25. Erratum in: J Exp Med 1999 May 3; 189(9):following 1518. PubMed PMID: 9989976; PubMed Central PMCID: PMC2192941.

211. Ramsay A J, Leong K H, Ramshaw I A. DNA vaccination against virus infection and enhancement of antiviral immunity following consecutive immunization with DNA and viral vectors. Immunol Cell Biol. 1997 August; 75(4):382-8. Review. PubMed PMID: 9315482.

212. Ramshaw I A, Ramsay A J. The prime-boost strategy: exciting prospects for improved vaccination. Immunol Today. 2000 April; 21(4):163-5. Review. PubMed PMID: 10740236.

213. Rerks-Ngarm S, Pitisuttithum P, Nitayaphan S, Kaewkungwal J, Chiu J, Paris R, Premsri N, Namwat C, de Souza M, Adams E, Benenson M, Gurunathan S, Tartaglia J, McNeil J G, Francis D P, Stablein D, Birx D L, Chunsuttiwat S, Khamboonruang C, Thongcharoen P, Robb M L, Michael N L, Kunasol P, Kim J H; MOPH-TAVEG Investigators. Vaccination with ALVAC and AIDSVAX to prevent HIV-1 infection in Thailand. N Engl. J Med. 2009 Dec. 3; 361(23):2209-20. doi: 10.1056/NEJMoa0908492. Epub 2009 Oct. 20. PubMed PMID: 19843557.

214. Richie T L, Saul A. Progress and challenges for malaria vaccines. Nature. 2002 Feb. 7; 415(6872):694-701. Review. PubMed PMID: 11832958.

215. Richmond J F, Mustafa F, Lu S, Santoro J C, Weng J, O'Connell M, FenyöE M, Hurwitz J L, Montefiori D C, Robinson H L. Screening of HIV-1 Env glycoproteins for the ability to raise neutralizing antibody using DNA immunization and recombinant vaccinia virus boosting. Virology. 1997 Apr. 14; 230(2):265-74. PubMed PMID: 9143282.

216. Rieckmann K H, Beaudoin R L, Cassells J S, Sell K W. Use of attenuated sporozoites in the immunization of human volunteers against falciparum malaria. Bull World Health Organ. 1979; 57 Suppl 1:261-5. PubMed PMID: 120773; PubMed Central PMCID: PMC2395727.

217. Robinson H L. Working towards an HIV/AIDS vaccine. Hum Vaccin. 2009 July; 5(7):436-8. PubMed PMID: 19662687.

218. Roestenberg M, Teirlinck A C, McCall M B, Teelen K, Makamdop K N, Wiersma J, Arens T, Beckers P, van Gemert G, van de Vegte-Bolmer M, van der Ven A J, Luty A J, Hermsen C C, Sauerwein R W. Long-term protection against malaria after experimental sporozoite inoculation: an open-label follow-up study. Lancet. 2011 May 21; 377 (9779): 1770-6. doi: 10.1016/S0140-6736(11)60360-7. Epub 2011 Apr. 22. PubMed PMID: 21514658.

219. Rollier C S, Reyes-Sandoval A, Cottingham M G, Ewer K, Hill A V. Viral vectors as vaccine platforms: deployment in sight. Curr Opin Immunol. 2011 June; 23(3): 377-82. doi: 10.1016/j.coi.2011.03.006. Epub 2011 Apr. 20. Review. PubMed PMID: 21514130.

220. Rupprecht C E, Wiktor T J, Johnston D H, Hamir A N, Dietzschold B, Wunner W H, Glickman L T, Koprowski H. Oral immunization and protection of raccoons (Procyon lotor) with a vaccinia-rabies glycoprotein recombinant virus vaccine. Proc Natl Acad Sci USA. 1986 October; 83(20): 7947-50. PubMed PMID: 3464010; PubMed Central PMCID: PMC386841.

221. Sancho M C, Schleich S, Griffiths G, Krijnse-Locker J. The block in assembly of modified vaccinia virus Ankara in HeLa cells reveals new insights into vaccinia virus morphogenesis. J Virol. 2002 August; 76(16):8318-34. PubMed PMID: 12134037; PubMed Central PMCID: PMC155139.

222. Sandström E, Nilsson C, Hejdeman B, Brave A, Bratt G, Robb M, Cox J, Vancott T, Marovich M, Stout R, Aboud S, Bakari M, Pallangyo K, Ljungberg K, Moss B, Earl P, Michael N, Birx D, Mhalu F, Wahren B, Biberfeld G; HIV Immunogenicity Study 01/02 Team. Broad immunogenicity of a multigene, multiclade HIV-1 DNA vaccine boosted with heterologous HIV-1 recombinant modified vaccinia virus Ankara. J Infect Dis. 2008 Nov. 15; 198(10):1482-90. doi: 10.1086/592507. PubMed PMID: 18808335.

223. Scriba T J, Tameris M, Mansoor N, Smit E, van der Merwe L, Isaacs F, Keyser A, Moyo S, Brittain N, Lawrie A, Gelderbloem S, Veldsman A, Hatherill M, Hawkridge A, Hill A V, Hussey G D, Mahomed H, McShane H, Hanekom W A. Modified vaccinia Ankara-expressing Ag85A, a novel tuberculosis vaccine, is safe in adolescents and children, and induces polyfunctional CD4+ T cells. Eur J Immunol. 2010 January; 40(1):279-90. doi: 10.1002/eji.200939754. Erratum in: Eur J Immunol. 2011 May; 41(5):1501. PubMed PMID: 20017188; PubMed Central PMCID: PMC3044835.

224. Sekaly R P. The failed HIV Merck vaccine study: a step back or a launching point for future vaccine development? J Exp Med. 2008 Jan. 21; 205(1):7-12. doi: 10.1084/jem.20072681. Epub 2008 Jan. 14. PubMed PMID: 18195078; PubMed Central PMCID: PMC2234358.

225. Sheehy S H, Duncan C J, Elias S C, Choudhary P, Biswas S, Halstead F D, Collins K A, Edwards N J, Douglas A D, Anagnostou N A, Ewer K J, Havelock T, Mahungu T, Bliss C M, Miura K, Poulton I D, Lillie P J, Antrobus R D, Berrie E, Moyle S, Gantlett K, Colloca S, Cortese R, Long C A, Sinden R E, Gilbert S C, Lawrie A M, Doherty T, Faust S N, Nicosia A, Hill A V, Draper S J. ChAd63-MVA-vectored blood-stage malaria vaccines targeting MSP1 and AMA1: assessment of efficacy against mosquito bite challenge in humans. Mol Ther. 2012 December; 20(12):2355-68. doi: 10.1038/mt.2012.223. Epub 2012 Oct. 23. PubMed PMID: 23089736; PubMed Central PMCID: PMC3519995.

226. Shen X, Wong S B, Buck C B, Zhang J, Siciliano R F. Direct priming and cross-priming contribute differentially to the induction of CD8+ CTL following exposure to vaccinia virus via different routes. J Immunol. 2002 Oct. 15; 169(8):4222-9. PubMed PMID: 12370352.

227. Shida H, Hinuma Y, Hatanaka M, Morita M, Kidokoro M, Suzuki K, Maruyama T, Takahashi-Nishimaki F, Sugimoto M, Kitamura R, et al. Effects and virulences of recombinant vaccinia viruses derived from attenuated strains that express the human T-cell leukemia virus type I envelope gene. J Virol. 1988 December; 62(12):4474-80. PubMed PMID: 3184271; PubMed Central PMCID: PMC253556.

228. Shisler J L, Jin X L. The vaccinia virus K1L gene product inhibits host NF-kappaB activation by preventing IkappaBalpha degradation. J Virol. 2004 April; 78(7):3553-60. PubMed PMID: 15016878; PubMed Central PMCID: PMC371086.

229. Smith G L, Murphy B R, Moss B. Construction and characterization of an infectious vaccinia virus recombinant that expresses the influenza hemagglutinin gene and induces resistance to influenza virus infection in hamsters. Proc Natl Acad Sci USA. 1983 December; 80(23):7155-9. PubMed PMID: 6580632; PubMed Central PMCID: PMC390012.

230. Smith G L, Mackett M, Moss B. Infectious vaccinia virus recombinants that express hepatitis B virus surface antigen. Nature. 1983 Apr. 7;302(5908):490-5. PubMed PMID: 6835382.

231. Smith J M, Amara R R, Campbell D, Xu Y, Patel M, Sharma S, Butera S T, Ellenberger D L, Yi H, Chennareddi L, Herndon J G, Wyatt L S, Montefiori D, Moss B, McClure H M, Robinson H L. DNA/MVA vaccine for HIV type 1: effects of codon-optimization and the expression of aggregates or virus-like particles on the immunogenicity of the DNA prime. AIDS Res Hum Retroviruses. 2004 December; 20(12): 1335-47. PubMed PMID: 15650426.

232. Sridhar S, Reyes-Sandoval A, Draper S J, Moore A C, Gilbert S C, Gao G P, Wilson J M, Hill A V. Single-dose protection against *Plasmodium berghei* by a simian adenovirus vector using a human cytomegalovirus promoter containing intron A. J Virol. 2008 April; 82(8):3822-33. doi: 10.1128/JVI.02568-07. Epub 2008 Feb. 6. PubMed PMID: 18256155; PubMed Central PMCID: PMC2293012.

233. Stack J, Haga I R, Schröder M, Bartlett N W, Maloney G, Reading P C, Fitzgerald K A, Smith G L, Bowie A G. Vaccinia virus protein A46R targets multiple Toll-like-interleukin-1 receptor adaptors and contributes to virulence. J Exp Med. 2005 Mar. 21; 201 (6): 1007-18. Epub 2005 Mar. 14. PubMed PMID: 15767367; PubMed Central PMCID: PMC2213104.

234. Stevceva L, Alvarez X, Lackner A A, Tryniszewska E, Kelsall B, Nacsa J, Tartaglia J, Strober W, Franchini G. Both mucosal and systemic routes of immunization with the live, attenuated NYVAC/simian immunodeficiency virus SIV(gpe) recombinant vaccine result in gag-specific CD8(+) T-cell responses in mucosal tissues of macaques. J Virol. 2002 November; 76(22): 11659-76. PubMed PMID: 12388726; PubMed Central PMCID: PMC 136754.

235. Stevceva L, Abimiku A G, Franchini G. Targeting the mucosa: genetically engineered vaccines and mucosal immune responses. Genes Immun. 2000 June; 1(5):308-15. Review. PubMed PMID: 11196691.

236. Stittelaar K J, Kuiken T, de Swart R L, van Amerongen G, Vos H W, Niesters H G, van Schalkwijk P, van der Kwast T, Wyatt L S, Moss B, Osterhaus A D. Safety of modified vaccinia virus Ankara (MVA) in immune-suppressed macaques. Vaccine. 2001 Jun. 14; 19(27):3700-9. PubMed PMID: 11395204.

237. Sullivan V, Smith G L. Expression and characterization of herpes simplex virus type 1 (HSV-1) glycoprotein G (gG) by recombinant vaccinia virus: neutralization of HSV-1 infectivity with anti-gG antibody. J Gen Virol. 1987 October; 68 (Pt 10):2587-98. PubMed PMID: 2822841.

238. Sutterwala F S, Mijares L A, Li L, Ogura Y, Kazmierczak B I, Flavell R A. Immune recognition of *Pseudomonas aeruginosa* mediated by the IPAF/NLRC4 inflammasome. J Exp Med. 2007 Dec. 24; 204(13):3235-45. Epub 2007 Dec. 10. PubMed PMID: 18070936; PubMed Central PMCID: PMC2150987.

239. Tartaglia J, Perkus M E, Taylor J, Norton E K, Audonnet J C, Cox W I, Davis S W, van der Hoeven J, Meignier B, Riviere M, et al. NYVAC: a highly attenuated strain of vaccinia virus. Virology. 1992 May; 188(1):217-32. PubMed PMID: 1566575.

240. Teklehaimanot A, McCord G C, Sachs J D. Scaling up malaria control in Africa: an economic and epidemiological assessment. Am J Trop Med Hyg. 2007 December; 77(6 Suppl): 138-44. Review. PubMed PMID: 18165486.

241. Theofilopoulos A N, Baccala R, Beutler B, Kono D H. Type I interferons (alpha/beta) in immunity and autoimmunity. Annu Rev Immunol. 2005; 23:307-36. Review. PubMed PMID: 15771573.

242. Thera M A, Plowe C V. Vaccines for malaria: how close are we? Annu Rev Med. 2012;63:345-57. doi: 10.1146/annurev-med-022411-192402. Epub 2011 Nov. 10. Review. PubMed PMID: 22077719; PubMed Central PMCID: PMC3338248.

243. Thera M A, Doumbo O K, Coulibaly D, Laurens M B, Ouattara A, Kone A K, Guindo A B, Traore K, Traoré I, Kouriba B, Diallo D A, Diana I, 0 M, Dolo A, Tolo Y, Sissoko M S, Niangaly A, Sissoko M, Takala-Harrison S, Lyke K E, Wu Y, Blackwelder W C, Godeaux O, Vekemans J, Dubois M C, Ballou W R, Cohen J, Thompson D, Dube T, Soisson L, Diggs C L, House B, Lanar D E, Dutta S, Heppner D G Jr, Plowe C V. A field trial to assess a blood-stage malaria vaccine. N Engl J Med. 2011 Sep. 15; 365(11): 1004-13. doi: 10.1056/NEJMoa1008115. PubMed PMID: 21916638; PubMed Central PMCID: PMC3242358.

244. Uematsu S, Jang M H, Chevrier N, Guo Z, Kumagai Y, Yamamoto M, Kato H, Sougawa N, Matsui H, Kuwata H, Hemmi H, Coban C, Kawai T, Ishii K J, Takeuchi O, Miyasaka M, Takeda K, Akira S. Detection of pathogenic intestinal bacteria by Toll-like receptor 5 on intestinal CD11c+ lamina propria cells. Nat Immunol. 2006 August; 7(8):868-74. Epub 2006 Jul. 9. PubMed PMID: 16829963.

245. van Montfoort N, Camps M G, Khan S, Filippov D V, Weterings J J, Griffith J M, Geuze H J, van Hall T, Verbeek J S, Melief C J, Ossendorp F. Antigen storage compartments in mature dendritic cells facilitate prolonged cytotoxic T lymphocyte cross-priming capacity. Proc Natl Acad Sci USA. 2009 Apr. 21; 106(16):6730-5. doi: 10.1073/pnas.0900969106. Epub 2009 Apr. 3. PubMed PMID: 19346487; PubMed Central PMCID: PMC2672553.

246. Verardi P H, Jones L A, Aziz F H, Ahmad S, Yilma T D. Vaccinia virus vectors with an inactivated gamma interferon receptor homolog gene (B8R) are attenuated In vivo without a concomitant reduction in immunogenicity. J Virol. 2001 January; 75(1):1 1-8. PubMed PMID: 11119568; PubMed Central PMCID: PMC 113892.

247. Vijaysri S, Jentarra G, Heck M C, Mercer A A, McInnes C J, Jacobs B L. Vaccinia viruses with mutations in the E3L gene as potential replication-competent, attenuated vaccines: intra-nasal vaccination. Vaccine. 2008 Jan. 30; 26(5):664-76. Epub 2007 Dec. 4. PubMed PMID: 18096276; PubMed Central PMCID: PMC2576474.

248. von Krempelhuber A, Vollmar J, Pokorny R, Rapp P, Wulff N, Petzold B, Handley A, Mateo L, Siersbol H, Kollaritsch H, Chaplin P. A randomized, double-blind, dose- 248. [continued] finding Phase II study to evaluate immunogenicity and safety of the third generation smallpox vaccine candidate IMVAMUNE. Vaccine. 2010 Feb. 3; 28(5): 1209-16. doi: 10.1016/j.vaccine.2009.11.030. Epub 2009 Nov. 25. PubMed PMID: 19944151; PubMed Central PMCID: PMC2814951.

249. von Mehren M, Arlen P, Tsang K Y, Rogatko A, Meropol N, Cooper H S, Davey M, McLaughlin S, Schlom J, Weiner L M. Pilot study of a dual gene recombinant avipox vaccine containing both carcinoembryonic antigen (CEA) and B7.1 transgenes in patients with recurrent CEA-expressing adenocarcinomas. Clin Cancer Res. 2000 June; 6(6):2219-28. PubMed PMID: 10873071.

250. Vora P, Youdim A, Thomas L S, Fukata M, Tesfay S Y, Lukasek K, Michelsen K S, Wada A, Hirayama T, Arditi M, Abreu M T. Beta-defensin-2 expression is regulated by TLR signaling in intestinal epithelial cells. J Immunol. 2004 Nov. 1; 173(9):5398-405. PubMed PMID: 15494486.

251. Walker B D, Burton D R. Toward an AIDS vaccine. Science. 2008 May 9; 320(5877):760-4. doi: 10.1126/science.1152622. Review. PubMed PMID: 18467582.

252. Wang B Z, Gill H S, Kang S M, Wang L, Wang Y C, Vassilieva E V, Compans R W. Enhanced influenza virus-like particle vaccines containing the extracellular domain of matrix protein 2 and a Toll-like receptor ligand. Clin Vaccine Immunol. 2012 August; 19(8):1119-25. doi: 10.1128/CVI.00153-12. Epub 2012 May 30. PubMed PMID: 22647270; PubMed Central PMCID: PMC3416094.

253. Wang B Z, Quan F S, Kang S M, Bozja J, Skountzou I, Compans R W. Incorporation of membrane-anchored flagellin into influenza virus-like particles enhances the breadth of immune responses. J Virol. 2008 December; 82(23):11813-23. doi: 10.1128/JVI.01076-08. Epub 2008 Sep. 10. PubMed PMID: 18786995; PubMed Central PMCID: PMC2583664.

254. Webster D P, Dunachie S, Vuola J M, Berthoud T, Keating S, Laidlaw S M, McConkey S J, Poulton I, Andrews L, Andersen R F, Bejon P, Butcher G, Sinden R, Skinner M A, Gilbert S C, Hill A V. Enhanced T cell-mediated protection against malaria in human challenges by using the recombinant poxviruses FP9 and modified vaccinia virus Ankara. Proc Natl Acad Sci USA. 2005 Mar. 29; 102(13): 4836-41. Epub 2005 Mar. 21. PubMed PMID: 15781866; PubMed Central PMCID: PMC555695.

255. Weiss R, Gabler M, Jacobs T, Gilberger T W, Thalhamer J, Scheiblhofer S. Differential effects of C3d on the immunogenicity of gene gun vaccines encoding *Plasmodium falciparum* and *Plasmodium berghei* MSP1(42). Vaccine. 2010 Jun. 17; 28(28):4515-22. doi: 10.1016/j.vaccine.2010.04.054. Epub 2010 May 15. PubMed PMID: 20438877.

256. Werden S J, Rahman M M, McFadden G. Poxvirus host range genes. Adv Virus Res. 2008;71:135-71. doi: 10.1016/S0065-3527(08)00003-1. Review. PubMed PMID: 18585528.

257. Weyer J, Rupprecht C E, Nel L H. Poxvirus-vectored vaccines for rabies—a review. Vaccine. 2009 Nov. 27; 27(51):7198-201. doi: 10.1016/j.vaccine.2009.09.033. Review. PubMed PMID: 19925953.

258. Weyer J, Rupprecht C E, Mans J, Viljoen G J, Nel L H. Generation and evaluation of a recombinant modified vaccinia virus Ankara vaccine for rabies. Vaccine. 2007 May 22; 25(21):4213-22. Epub 2007 Mar. 22. PubMed PMID: 17434244.

259. Whelan K T, Pathan A A, Sander C R, Fletcher H A, Poulton I, Alder N C, Hill A V, McShane H. Safety and immunogenicity of boosting BCG vaccinated subjects with BCG: comparison with boosting with a new TB vaccine, MVA85A. PLoS One. 2009 Jun. 16; 4(6):e5934. doi: 10.1371/journal.pone.0005934. Erratum in: PLoS One. 2011;6(2). doi:10.1371/annotation/ec8cc565-bf24-4898-b7ba-6e0423d5809f. PubMed PMID: 19529780; PubMed Central PMCID: PMC2694271.

260. Wiktor T J, Macfarlan R I, Reagan K J, Dietzschold B, Curtis P J, Wunner W H, Kieny M P, Lathe R, Lecocq J P, Mackett M, et al. Protection from rabies by a vaccinia virus recombinant containing the rabies virus glycoprotein gene. Proc Natl Acad Sci USA. 1984 November; 81(22): 7194-8. PubMed PMID: 6095272; PubMed Central PMCID: PMC392104.

261. Willis K L, Patel S, Xiang Y, Shisler J L. The effect of the vaccinia K1 protein on the PKR-eIF2alpha pathway in RK13 and HeLa cells. Virology. 2009 Nov. 10; 394(1):73-81. doi: 10.1016/j.virol.2009.08.020. Epub 2009 Sep. 9. PubMed PMID: 19744687; PubMed Central PMCID: PMC2767412.

262. Wilson N A, Reed J, Napoe G S, Piaskowski S, Szymanski A, Furlott J, Gonzalez E J, Yant L J, Maness N J, May G E, Soma T, Reynolds M R, Rakasz E, Rudersdorf R, McDermott A B, O'Connor D H, Friedrich T C, Allison D B, Patki A, Picker L J, Burton D R, Lin J, Huang L, Patel D, Heindecker G, Fan J, Citron M, Horton M, Wang F, Liang X, Shiver J W, Casimiro D R, Watkins D I. Vaccine-induced cellular immune responses reduce plasma viral concentrations after repeated low-dose challenge with pathogenic simian immunodeficiency virus SIVmac239. J Virol. 2006 June; 80(12):5875-85. PubMed PMID: 16731926; PubMed Central PMCID: PMC1472612.

263. Woodland D L. Jump-starting the immune system: prime-boosting comes of age. Trends Immunol. 2004 February; 25(2):98-104. Review. PubMed PMID: 15102369.

264. Wyatt L S, Earl P L, Liu J Y, Smith J M, Montefiori D C, Robinson H L, Moss B. Multiprotein HIV type 1 clade B DNA and MVA vaccines: construction, expression, and immunogenicity in rodents of the MVA component. AIDS Res Hum Retroviruses. 2004 June; 20(6):645-53. PubMed PMID: 15242542.

265. Wyatt L S, Carroll M W, Czerny C P, Merchlinsky M, Sisler J R, Moss B. Marker rescue of the host range restriction defects of modified vaccinia virus Ankara. Virology. 1998 Nov. 25; 251(2):334-42. PubMed PMID: 9837798.

266. Yamamoto M, Sato S, Hemmi H, Hoshino K, Kaisho T, Sanjo H, Takeuchi O, Sugiyama M, Okabe M, Takeda K, Akira S. Role of adaptor TRIF in the MyD88-independent toll-like receptor signaling pathway. Science. 2003 Aug. 1; 301(5633):640-3. Epub 2003 Jul. 10. PubMed PMID: 12855817.

267. Yanisch-Perron C, Vieira J, Messing J. Improved M13 phage cloning vectors and host strains: nucleotide sequences of the M13mp18 and pUC19 vectors. Gene. 1985; 33(1):103-19. Erratum in: Gene. 1992 May 1; 114(1):81-3. PubMed PMID: 2985470.

268. Yilma T D. Prospects for the total eradication of rinderpest. Vaccine. 1989 December; 7(6):484-5. PubMed PMID: 2609722.

269. Yoshida S, Nagumo H, Yokomine T, Araki H, Suzuki A, Matsuoka H. *Plasmodium berghei* circumvents immune responses induced by merozoite surface protein 1-and apical membrane antigen 1-based vaccines. PLoS One. 2010 Oct. 28; 5(10):e 13727. doi: 10.1371/journal.pone.0013727. PubMed PMID: 21060850; PubMed Central PMCID: PMC2965677.

270. Zhao Y, Yang J, Shi J, Gong Y N, Lu Q, Xu H, Liu L, Shao F. The NLRC4 inflammasome receptors for bacterial flagellin and type III secretion apparatus. Nature. 2011 Sep. 14; 477(7366):596-600. doi: 10.1038/nature10510. PubMed PMID: 21918512.

271. Zieg J, Silverman M, Hilmen M, Simon M. Recombinational switch for gene expression. Science. 1977 Apr. 8; 196(4286): 170-2. PubMed PMID: 322276.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A recombinant or engineered poxvirus that contains DNA encoding, for expression of each of:
   *Plasmodium* circumsporozoite protein (CSP),
   *Plasmodium* sporozoite surface protein 2 (PfSSP2),
   *Plasmodium* liver stage antigen 1 (LSA-1)-repeatless,
   *Plasmodium* merozoite surface antigen 1 (MSA-1),
   *Plasmodium* serine repeat antigen (SERA),
   *Plasmodium* apical membrane antigen 1 (AMA-1),
   *Plasmodium* 25-kDa sexual-stage antigen (Pfs25), and
   Flagellin,
   wherein:
   the *Plasmodium* antigen AMA-1 is coded for by a nucleotide sequence comprising the AMA-1 coding sequence contained in SEQ ID NO:19;
   the Flagellin is expressed as a peptide and not as a fusion; and
   the poxvirus is a NYVAC virus, an ALVAC virus, a TROVAC virus, a MVA virus, a MVA-BN virus, an avipox virus, a canarypox virus, or a fowlpox virus.

2. The recombinant or engineered poxvirus of claim 1, further comprising DNA encoding, for expression of vaccinia host range gene K1L.

3. The recombinant or engineered poxvirus of claim 1 or 2, wherein the poxvirus comprises a NYVAC virus.

4. The recombinant or engineered poxvirus of claim 1 or 2, wherein the poxvirus comprises a MVA virus, or MVA-BN virus.

5. The recombinant or engineered poxvirus of claim 1 or 2, wherein the poxvirus comprises a fowlpox virus.

6. A method of inducing an immunological response against malaria, *Plasmodium* or a *Plasmodium* antigens in a mammal comprising administering to the mammal the recombinant or engineered poxvirus of claim 1 or 2, or an immunological or immunogenic composition containing the recombinant or engineered poxvirus.

7. An immunological or immunogenic composition containing the recombinant or engineered poxvirus of claim 1 or 2.

8. The recombinant or engineered poxvirus of claim 1 or 2, wherein the poxvirus comprises an ALVAC virus.

9. The recombinant or engineered poxvirus of claim 1 or 2, wherein the poxvirus comprises an avipox virus.

10. The recombinant or engineered poxvirus of claim 1 or 2, wherein the poxvirus comprises a TROVAC virus.

11. The recombinant or engineered poxvirus of claim 1 or 2, wherein the poxvirus comprises a canarypox virus.

12. The recombinant or engineered poxvirus of claim 1 or 2, wherein the Flagellin is coded for by a nucleotide sequence comprising the Flagellin coding sequence contained in SEQ ID NO:19.

13. An anti-malarial immunogenic or immunological composition comprising a recombinant or engineered poxvirus of claim 1 or 2.

14. An immunogenic or immunological composition comprising a poxvirus of claim 3.

15. An immunogenic or immunological composition comprising a poxvirus of claim 4.

16. The recombinant or engineered poxvirus of claim 12, wherein the poxvirus comprises a NYVAC virus.

17. A method for inducing an immunogenic or immunological response against malaria or *Plasmodium* or a *Plasmodium* antigen in a mammal comprising administering to the mammal the recombinant or engineered poxvirus of claim 16 or an immunological or immunogenic composition containing the recombinant or engineered poxvirus.

18. A method for inducing an immunogenic or immunological response against malaria or *Plasmodium* or a *Plasmodium* antigen in a mammal comprising administering to the mammal the recombinant or engineered poxvirus of claim 3 or an immunological or immunogenic composition containing the recombinant or engineered poxvirus.

19. A method for inducing an immunogenic or immunological response against malaria or *Plasmodium* or a *Plasmodium* antigen in a mammal comprising administering to the mammal the recombinant or engineered poxvirus of claim 4 or an immunological or immunogenic composition containing the recombinant or engineered poxvirus.

* * * * *